United States Patent [19]
Hosoi et al.

[11] Patent Number: 6,048,064
[45] Date of Patent: Apr. 11, 2000

[54] OPTOMETRIC APPARATUS

[75] Inventors: Yoshinobu Hosoi; Taeko Horino, both of Aichi, Japan

[73] Assignee: Nidek Co., Ltd., Aichi, Japan

[21] Appl. No.: 09/107,284

[22] Filed: Jun. 30, 1998

[30] Foreign Application Priority Data

Jun. 30, 1997  [JP]  Japan ................................ 9-190691

[51] Int. Cl.[7] ............................................. A61B 3/10
[52] U.S. Cl. .................................................. 351/212
[58] Field of Search ................................. 351/205, 209, 351/210, 211, 212, 216, 217, 237, 245, 246, 221; 359/209, 211; 382/117

[56] References Cited

U.S. PATENT DOCUMENTS

| | | | |
|---|---|---|---|
| 3,891,311 | 6/1975 | Fletcher et al. .......................... 351/245 |
| 4,105,302 | 8/1978 | Tate, Jr. .................................... 351/210 |
| 5,444,504 | 8/1995 | Kobayashi et al. ..................... 351/237 |

*Primary Examiner*—George Manuel
*Attorney, Agent, or Firm*—Sughrue, Mion, Zinn, Macpeak & Seas, PLLC

[57] ABSTRACT

An optometric apparatus for correcting the refraction of an eye to be examined, which allows even a person who is inexperienced and unfamiliar with optometry to easily obtain appropriate prescription values, and conduct analysis of the visual function. The optometric apparatus has a rotary prism for imparting a prism power to the eye to be examined. An appropriate examination is conducted by using the rotary prism in accordance with a program stored in a memory to obtain the prism power of an expected state, and a result of examination is displayed.

10 Claims, 42 Drawing Sheets

UNAIDED (UNAIDED VISUAL ACUITY)
LM (LENSMETRY DATA) SPECTACLE
AR (AUTO REFRACTOMETER AUTO REF / KERATOMETER) OBJECTIVE
SUBJ (SUBJECTIVE)
FINAL (FINAL DATA) PRESCRIPTION

FIG. 16

TABLE A (POWER ADJUSTMENT FOR MYOPIA [INITIAL WEARING])

| PERFECT CORRECTION $S_1$ | CORRECTION AMOUNT $\Delta S_1$ |
|---|---|
| −0.25 | |
| −0.50 | |
| −0.75 | |
| −1.00 | |
| −1.25 | |
| −1.50 | |
| −1.75 | |
| −2.00 | $S_1/2$ (HOWEVER, ROUNDED UP IN 0.25D STEPS) |
| −2.25 | |
| −2.50 | |
| −2.75 | |
| −3.00 | |
| −3.25 | |
| −3.50 | |
| −3.75 | |
| −4.00 | |
| −4.25 | |
| −4.50 | |
| −4.75 | |
| −5.00 | |
| ⋮ | |

TABLE B (POWER ADJUSTMENT FOR MYOPIA [2ND TIME OR MORE])

| DIFFERENCE BETWEEN FORMER SPECTACLES AND PERFECT CORRECTION $S_2$ | CORRECTION AMOUNT $\Delta S_2$ |
|---|---|
| ⋮ | |
| +0.50 | |
| +0.25 | 0 |
| 0 | |
| −0.25 | |
| −0.50 | |
| −0.75 | |
| −1.00 | $S_2/2$ (HOWEVER, ROUNDED UP IN 0.25D STEPS) |
| −1.25 | |
| −1.50 | |
| −1.75 | |
| −2.00 | |
| −2.25 | |
| −2.50 | |
| −2.75 | $S_2+0.75$ |
| −3.00 | |
| ⋮ | |

TABLE C (POWER ADJUSTMENT FOR ASTIGMATISM [INITIAL WEARING])

| PERFECT CORRECTION $C_1$ | CORRECTION AMOUNT $\Delta C_1$ |
|---|---|
| −0.25 | |
| −0.50 | |
| −0.75 | |
| −1.00 | |
| −1.25 | |
| −1.50 | |
| −1.75 | $C_1/2$ (HOWEVER, ROUNDED UP IN 0.25D STEPS) |
| −2.00 | |
| −2.25 | |
| −2.50 | |
| −2.75 | |
| −3.00 | |
| −3.25 | |
| −3.50 | |
| −3.75 | |
| ⋮ | |

TABLE D (POWER ADJUSTMENT FOR ASTIGMATISM [2ND TIME OR MORE])

| DIFFERENCE BETWEEN FORMER SPECTACLES AND PERFECT CORRECTION $C_2$ | CORRECTION AMOUNT $\Delta C_2$ |
|---|---|
| ⋮ | |
| +0.50 | |
| +0.25 | 0 |
| 0 | |
| −0.25 | |
| −0.50 | |
| −0.75 | $C_2/2$ (HOWEVER, ROUNDED UP IN 0.25D STEPS) |
| −1.00 | |
| −1.25 | |
| −1.50 | |
| −1.75 | |
| −2.00 | |
| −2.25 | |
| −2.50 | |
| −2.75 | $C_2+0.75$ |
| −3.00 | |
| −3.25 | |
| ⋮ | |

FIG. 20
FORMER SPECTACLE : C=−0.50, A=20° (RESIDUAL ASTIGMATISM
PERFECT CORRECTION : C=−1.00, A=30°  WITH RESPECT TO
                                     PERFECT CORRECTION)
AUTOMATIC ADJUSTMENT PRESCRIPTION 1 : C=−0.75, A=30° (C=−0.25, A=30°)
1ST INPUT BY "WEAKEN" SWITCH, PRESCRIPTION 2 : C=−0.75, A=20° (C=−0.38, A=148.5°)
2ND INPUT BY "WEAKEN" SWITCH, PRESCRIPTION 3 : C=−0.50, A=30° (C=−0.50, A=30°)
3RD INPUT BY "WEAKEN" SWITCH, PRESCRIPTION 4 : C=−0.50, A=15° (C=−0.64, A=8°)

FIG. 23

```
---<R>----  <LM>  ----<L>---
  -2.00      S     -2.50
  -0.50      C     -0.25
    0        A       0
             VA
   (0.6)    (0.6)   (0.5)
---<R>----  <OBJ> ----<L>---
  -3.00      S     -3.50
  -1.25      C     -1.00
   176       A       0
             PD
    32       64      32
---<R>----  <SUBJ>----<L>---
  -2.50      S     -3.00
  -1.00      C     -1.75
   175       A       5
  +1.25     ADD    +1.25
             VA
   (1.2)    (1.5)   (1.2)
---<R>----  <FINAL>----<L>---
  -2.25      S     -2.75
  -0.75      C     -0.50      ⎫
   175       A       5        ⎬ 101
  +1.00     ADD    +1.00 (35cm)  ← 102
  +0.75     ADD    +0.75 (40cm)  ← 103
             VA
   (1.0)    (1.2)   (1.0)
       ** FAR+ADDITION **
  -1.25      S     -1.75
  -0.75      C     -0.50
   175       A       5
```

100 encompasses the FINAL block; 101 marks the S/C/A lines; 102 marks the +1.00 ADD (35cm) line; 103 marks the +0.75 ADD (40cm) line; 104 marks the FAR+ADDITION block.

FIG. 44

| FAR USE | | S | C | A | ADD (ADDITION) (POWER) | VA (VISUAL ACUITY) (VALUE) | |
|---|---|---|---|---|---|---|---|
| UNAIDED | R | — | — | — | — | 0.1 | 0.15 |
|  | L | — | — | — | — | 0.05 |  |
| LM (SPECTACLED) | R | −1.75 | −0.75 | 0 | +1.00 | 0.4 | 0.6 |
|  | L | −2.25 | −0.25 | 0 | +1.00 | 0.5 |  |
| AR (OBJECTIVE) | R | −3.00 | −1.50 | 176 |  |  |  |
|  | L | −3.50 | −1.00 | 4 |  |  |  |
| SUBJ (SUBJECTIVE) | R | −2.75 | −1.25 | 175 | +2.00 | 1.5 |  |
|  | L | −3.25 | −0.75 | 5 | +2.00 | 1.2 |  |
| FINAL (PRESCRIPTION) | R | −2.25 | −1.00 | 175 | +1.50 | 1.0 | 1.2 |
|  | L | −2.75 | −0.50 | 5 | +1.50 | 0.9 |  |

PD=62.00mm     ID NO.

| FOR FAR | FOR NEAR | SCA | PRISM | NPC.. | GRAPH | END |
| 128 | 129 | 130 | 131 | 132 | 133 | 134 |

FIG. 45

| NEAR USE | | S | C | A | ADD (ADDITION) (POWER) | VA (VISUAL ACUITY) (VALUE) | |
|---|---|---|---|---|---|---|---|
| UNAIDED | R | — | — | — | — | 0.1 | 0.2 |
|  | L | — | — | — | — | 0.1 |  |
| LM (SPECTACLED) | R | −0.75 | −0.75 | 0 |  | 0.5 | 0.7 |
|  | L | −1.25 | −0.25 | 0 |  | 0.6 |  |
| AR (OBJECTIVE) | R |  |  |  |  |  |  |
|  | L |  |  |  |  |  |  |
| SUBJ (SUBJECTIVE) | R | −0.75 | −1.25 | 175 |  | 1.0 |  |
|  | L | −1.25 | −0.75 | 5 |  | 1.0 |  |
| FINAL (PRESCRIPTION) | R |  |  |  |  |  |  |
|  | L |  |  |  |  |  |  |

PD=58.00mm     ID NO.

| FOR FAR | FOR NEAR | SCA | PRISM | NPC.. | GRAPH | END |

FIG. 46

| FAR USE | HORIZONTAL PRISM | VERTICAL PRISM | BLUR | BREAK | RECOVERY |
|---|---|---|---|---|---|
| UNAIDED R / L | — | — | — | — | — |
| LM (SPECTACLED) R / L | | | D / C | | |
| AR (OBJECTIVE) R / L | | | D / C | | |
| SUBJ (SUBJECTIVE) R / L | 0.00 / 11.50 | U 0.50 / 0.00 | D 9.00 / C | 7.00 / 16.00 | 4.00 / 10.00 |
| FINAL (PRESCRIPTION) R / L | | | D / C | | |

PD=62.00mm  ID NO.

[FOR FAR] [FOR NEAR] [SCA] [PRISM] [NPC..] [GRAPH] [END]

FIG. 47

| NEAR USE | HORIZONTAL PRISM | VERTICAL PRISM | BLUR | BREAK | RECOVERY |
|---|---|---|---|---|---|
| UNAIDED R / L | — | — | — | — | — |
| LM (SPECTACLED) R / L | | | D / C | | |
| AR (OBJECTIVE) R / L | | | D / C | | |
| SUBJ (SUBJECTIVE) R / L | 0.00 / 13.50 | U 0.50 / 0.00 | D 13.00 / C 17.00 | 21.00 / 22.00 | 14.00 / 13.00 |
| FINAL (PRESCRIPTION) R / L | | | D / C | | |

PD=62.00mm  ID NO.

[FOR FAR] [FOR NEAR] [SCA] [PRISM] [NPC..] [GRAPH] [END]

| NPC NEAR POINT OF CONVERGENCE | 8cm | 9.5 MA | 59.0 Δ |
|---|---|---|---|
|  | R | BINOCULAR | L |
| NPA NEAR POINT OF ACCOMMODATION |  | 20cm 5.00 D |  |
| NRA NEGATIVE RELATIVE ACCOMMODATIVE POWER |  | +2.00 +1.75 |  |
| PRA POSITIVE RELATIVE ACCOMMODATIVE POWER |  | -2.25 -2.00 |  |

PD=58.00mm  ID NO.

| FOR FAR | FOR NEAR | SCA | PRISM | NPC | GRAPH | END |

FIG. 50
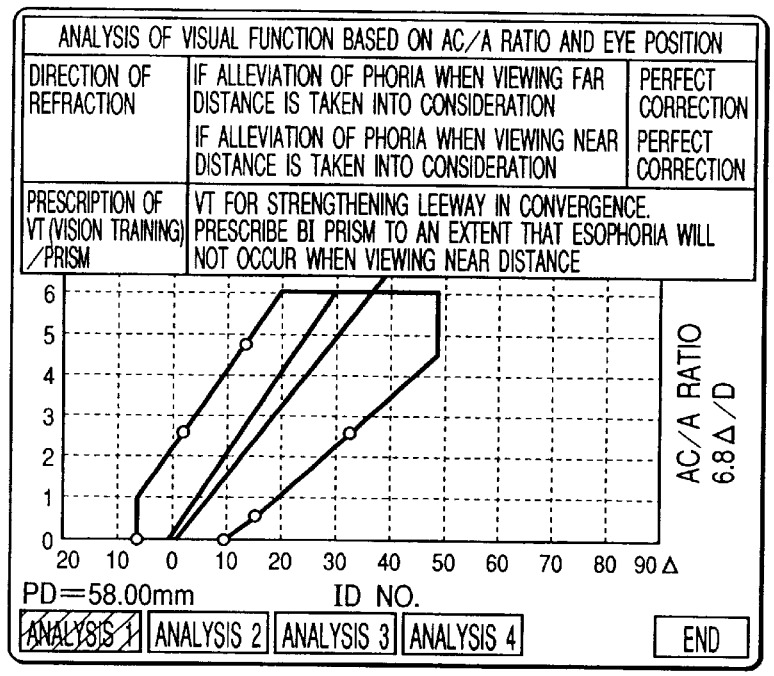
FIG. 51
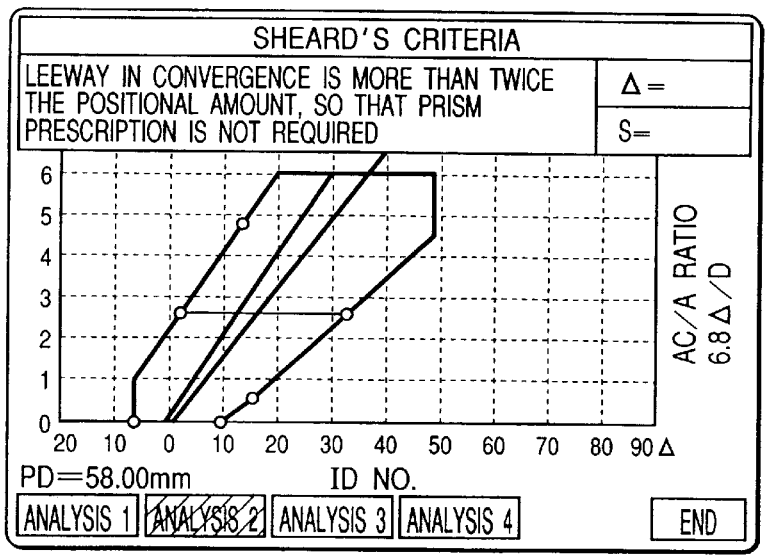
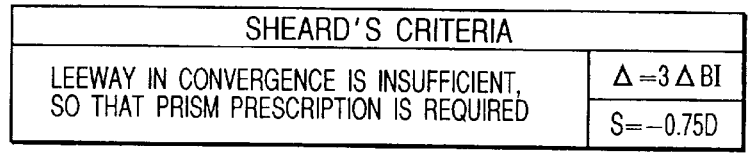
Δ : AMOUNT OF PRISM NECESSARY FOR SATISFYING THE SHEARD'S CRITERIA
R : LEEWAY IN CONVERGENCE
P : PHORIA
S : AMOUNT OF SPHERICAL POWER NECESSARY FOR SATISFYING THE SHEARD'S CRITERIA

FIG. 52
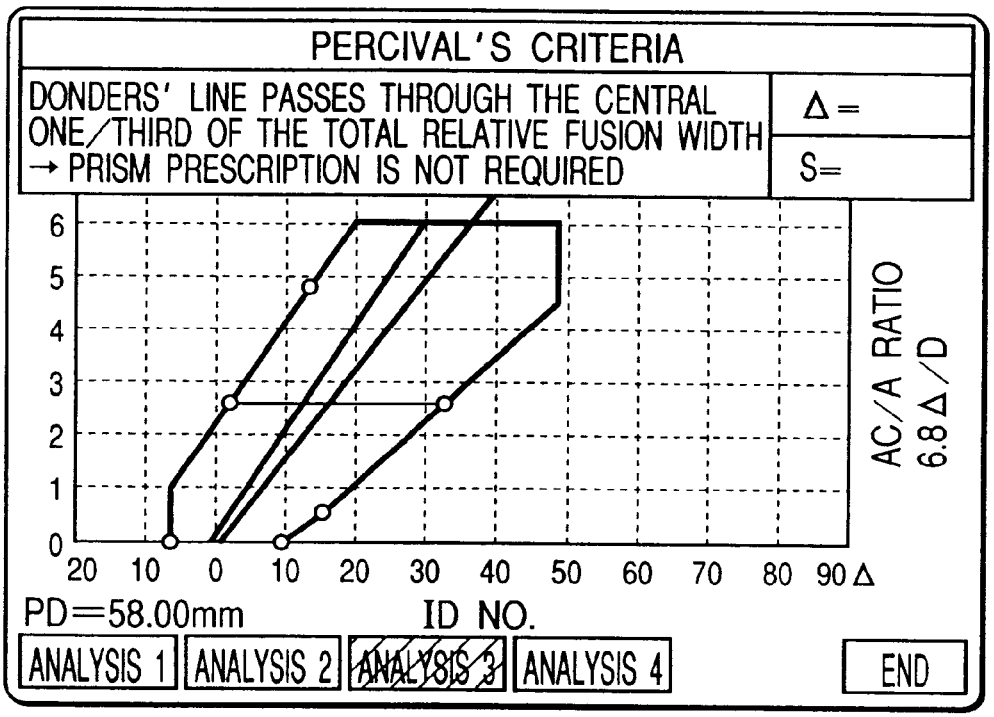
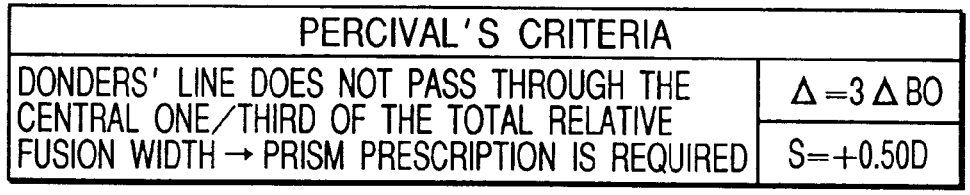
$$\Delta = (L-2+S)/3$$
$$S = \Delta /(AC/A)$$
Δ : AMOUNT OF PRISM NECESSARY FOR SATISFYING THE PERCIVAL'S CRITERIA
L : QUANTITATIVELY LARGER AMOUNT OF RELATIVE FUSION
S : QUANTITATIVELY SMALLER AMOUNT OF RELATIVE FUSION
S : AMOUNT OF SPHERICAL POWER NECESSARY FOR SATISFYING THE PERCIVAL'S CRITERIA FIG. 53
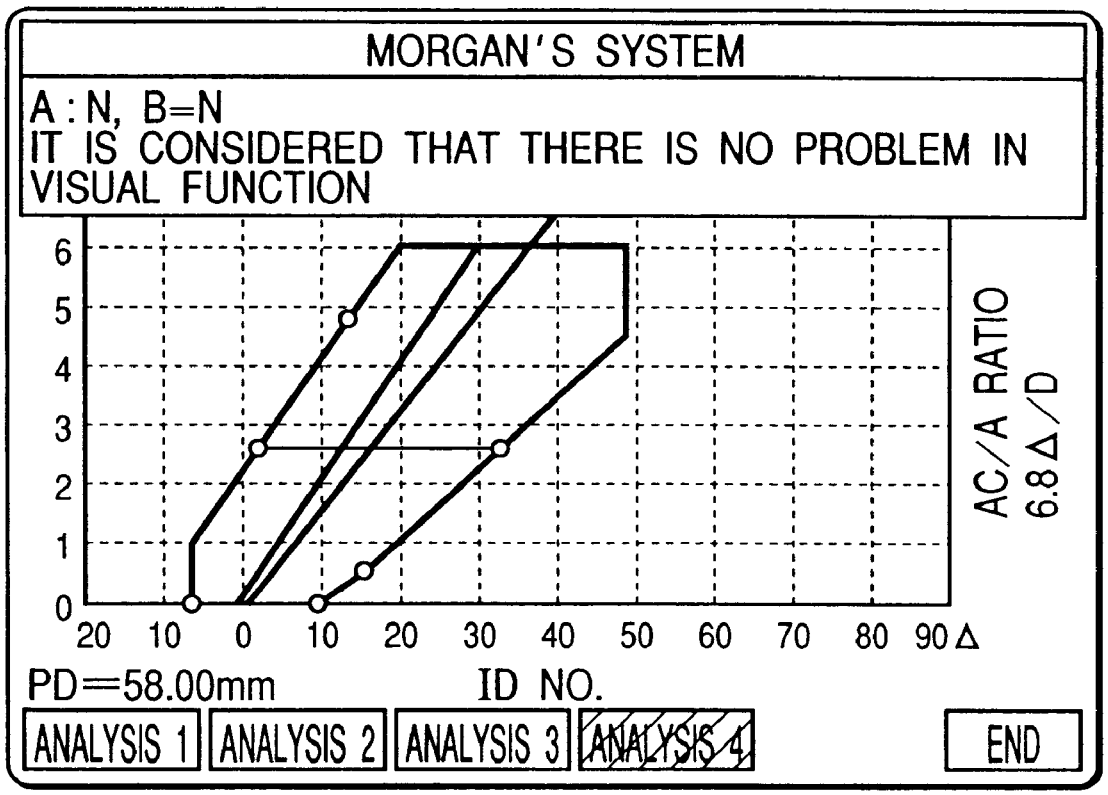
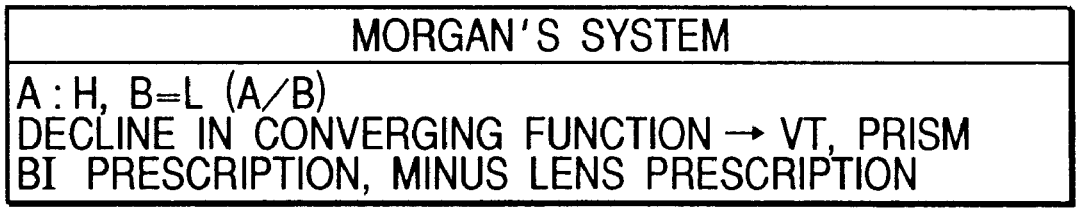
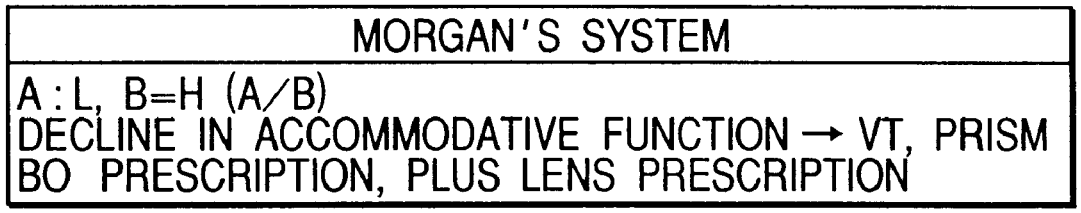

OPTOMETRIC APPARATUS

BACKGROUND OF THE INVENTION

The present invention relates to an optometric apparatus suitable for correction of refraction and visual function analysis of an eye to be examined.

When a refractive error (ametropia) is present in an eye to be examined and is to be corrected, it is important to prescribe such a power that will not impart an uneasy sensation and fatigue to a subject in wearing the spectacles after accurately examining the refractive state of the eye to be examined and by taking into consideration the complaints of the subject and powers of the former spectacles. In addition, if a visual function error such as phoria is present in the eye to be examined, it is necessary to analyze that visual function correctly and correct the same.

When determining a prescription power, a perfectly corrected refractive power test is generally conducted on the basis of data on examination such as an objective examination using a so-called refractometer and the measurement of powers of the former spectacles using a lens meter. In the perfectly corrected refractive power test, a subjective-type refractive-power measuring device in which optical elements having various optical characteristics are selectively disposed in test windows is used, responses on appearances of a presented test target (chart) is obtained from the subject, and a power at which maximum visual acuity can be obtained is determined. After a perfect correction power is obtained in the perfectly corrected refractive power test, the power adjustment is made on the basis of this power and the like, and prescription values are derived.

However, the procedure for deriving appropriate prescription values after obtaining the perfect correction power and adjusting that power largely depends on the knowledge and experience of the examiner, and is not easy for an inexperienced person.

There have been problems in that, particularly in a case where a visual function error such as phoria is present in the eye to be examined, substantial time is generally required in deriving prescription values after making power adjustment, and that there are differences in the derived prescription values among individual examiners.

SUMMARY OF THE INVENTION

A technical object of the present invention is to provide an optometric apparatus which allows even a person who is inexperienced and unfamiliar with optometry to easily obtain appropriate prescription values, and conduct analysis of the visual function.

To attain the above-noted object, the present invention provides the followings:

(1) An optometric apparatus for correcting refraction of an eye to be examined, comprising:
  a rotary prism for imparting a prism power to the eye to be examined;
  program storing means for storing a program for conducting examination by using the rotary prism;
  program advancing means for advancing the program;
  prism-power storing means for storing a prism power of an expected state; and
  display means for displaying a result of examination.

(2) An optometric apparatus according to (1), wherein the program stored in the program storing means includes a program in which an operating method in an examination process is displayed by the display means.

(3) An optometric apparatus according to (1), wherein the program stored in the program storing means includes at least one of a horizontal phoria test, a vertical phoria test, a divergence test, and a convergence test.

(4) An optometric apparatus according to (3), wherein tests for far use and near use are included in each of the tests.

(5) An optometric apparatus according to (1), wherein the program stored in the program storing means includes at least one of a near-point-of-convergence test, a near-point-of-accommodation test, and a near accommodation test.

(6) An optometric apparatus according to (5), further comprising:
  input means for inputting a distance from a root of a nose at the time of the near-point-of-convergence test or the near-point-of-accommodation test; and
  calculating means for effecting a predetermined calculation on the basis of the inputted distance.

(7) An optometric apparatus according to (1), wherein the result of examination displayed by the display means includes a result of analysis in which the result of examination is analyzed.

(8) A controller for operating a subjective-type refractive-power measuring device and a target presenting device in an optometric apparatus, the controller comprising:
  a memory which stores therein a program for a visual function test to be executed after perfect correction values for both eyes are obtained;
  a microcomputer circuit connected to the memory to control the subjective-type refractive-power measuring device and the target presenting device in accordance with the program;
  a switch section through which an examiner can control the subjective-type target presenting device and can instruct whether a current test item of the visual function test should be continued depending on a reply from a subject; and
  a display on which an advice regarding how to control the subjective-type target presenting device is displayed if the examiner instructs, through the switch section, that the current test item should be continued.

(9) A controller according to (8), wherein the memory automatically stores therein a result of the current test item if the examiner instructs that the current test item should not be continued.

(10) A controller designed for an optometric apparatus, comprising:
  a memory which stores therein a program for a visual function test including at least one of horizontal phoria test, a vertical phoria test, a divergence test, a convergence test, a near-point-of-convergence test, a near-point-of-accommodation test, and a near accommodation test;
  a microcomputer circuit connected to the memory;
  a switch section connected to the microcomputer circuit; and
  a display connected to the microcomputer circuit.

The present disclosure relates to the subject matter contained in Japanese patent application No. Hei. 9-190691 (filed on Jun. 30, 1997) which is expressly incorporated herein by reference in its entirety.

BRIEF DESCRIPTION OF THE DRAWINGS

In the accompanying drawings:

FIG. 16 is a diagram illustrating calculation using tables A to table D for obtaining a correction amount for adjusting the correction power;

FIG. 17 is a diagram illustrating an example of the screen of the display after automatic adjustment;

FIG. 20 is a diagram illustrating a specific example of adjustment of astigmatism (cylinder) with respect to an input by a switch when an uneasy sensation is present in manual adjustment E;

FIG. 21 is a diagram illustrating an example of display when manual adjustment has been made with respect to automatically adjusted powers;

FIG. 22 is a diagram illustrating the display of an operational instruction when a necessary near-work distance is inputted;

FIG. 23 is a diagram illustrating an example of a print;

FIG. 44 is a diagram illustrating an example of the screen of the display of a table of data in a visual function test;

FIG. 45 is a diagram illustrating an example of the screen of the display of a table of data in a visual function test;

FIG. 46 is a diagram illustrating an example of the screen of the display of a table of data in a visual function test;

FIG. 47 is a diagram illustrating an example of the screen of the display of a table of data in a visual function test;

FIG. 50 is a diagram illustrating an example of the screen displaying the results of analysis and a method of prescription based on the AC/A ratio and the eye position;

FIG. 51 is a diagram illustrating an example of the screen displaying the results of analysis and a method of prescription based on the Sheard criteria;

FIG. 52 is a diagram illustrating an example of the screen displaying the results of analysis and a method of prescription based on the Percival's criteria; and FIG. 53 is a diagram illustrating an example of the screen displaying the results of analysis and a method of prescription based on the Morgan's system.

DETAILED DESCRIPTION OF THE PREFERRED EMBODIMENT

Figure 1:
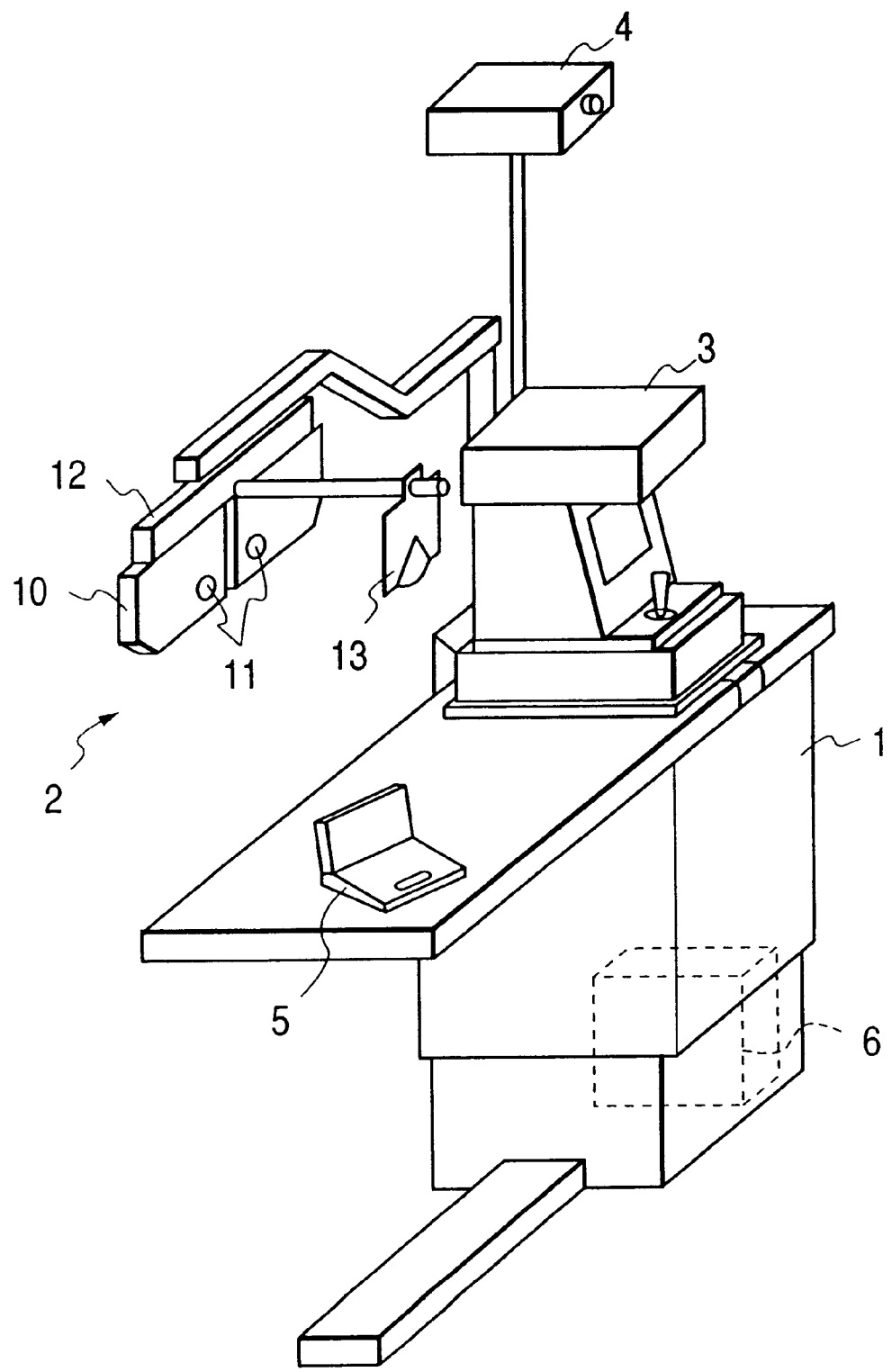
FIG. 1 is an external view illustrating an overall configuration of an optometric apparatus in accordance with an embodiment.

Referring now to the drawings, a description will be given of an embodiment of the present invention. FIG. 1 is an external view illustrating an overall configuration of an optometric apparatus in accordance the embodiment.

Reference numeral 1 denotes an examination table disposed between a subject and an examiner, and reference numeral 2 denotes a subjective-type refractive-power measuring device. The subjective-type refractive-power measuring device 2 is provided with a pair of left and right lens units 10 in which various optical elements are electrically driven so as to be selectively disposed in a pair of test windows 11, as well as a suspending portion 12 for suspending the left and right lens units 10. The suspending portion 12 has a sliding mechanism for correcting the interval between the left and right lens units 10 and a flapping mechanism (which will be described later) for making the optical axes of optical systems parallel with the visual axes in near vision of the subject. Numeral 13 denotes a visual test chart for near use which is held by a near-point rod attached to the suspending portion 12 (this visual test chart 13 is removed from the front of the eyes during an examination for far use).

Numeral 3 denotes an objective-type ocular refractive-power measuring device for measuring the refractive power of the eye by projecting a measuring index onto the eyeground of the subject eye and detecting a projected image of the index on the eyeground by means of a light receiving means. The objective-type ocular refractive-power measuring device 3 has the function-of obtaining the interpupillary distance on the basis of an amount of movement of its measuring section having a measuring optical system when the measuring section is moved from a state of completion of alignment of one eye to a state of completion of alignment of the other eye. The objective-type ocular refractive-power measuring device 3 is placed on a moving tray which is slidable on the examination table 1, and during an objective examination the objective-type ocular refractive-power measuring device 3 is slid to a central position on the examination table 1 to execute measurement.

Numeral 4 denotes a projection-type target (chart) presenting device for presenting test targets (charts). Numeral 5 denotes a controller for operating the subjective-type refractive-power measuring device 2 and the projection-type target (chart) presenting device 4, and numeral 6 denotes a relay unit for relaying communication between the respective devices. A lens meter is also connected to the relay unit 6.

Figure 2:
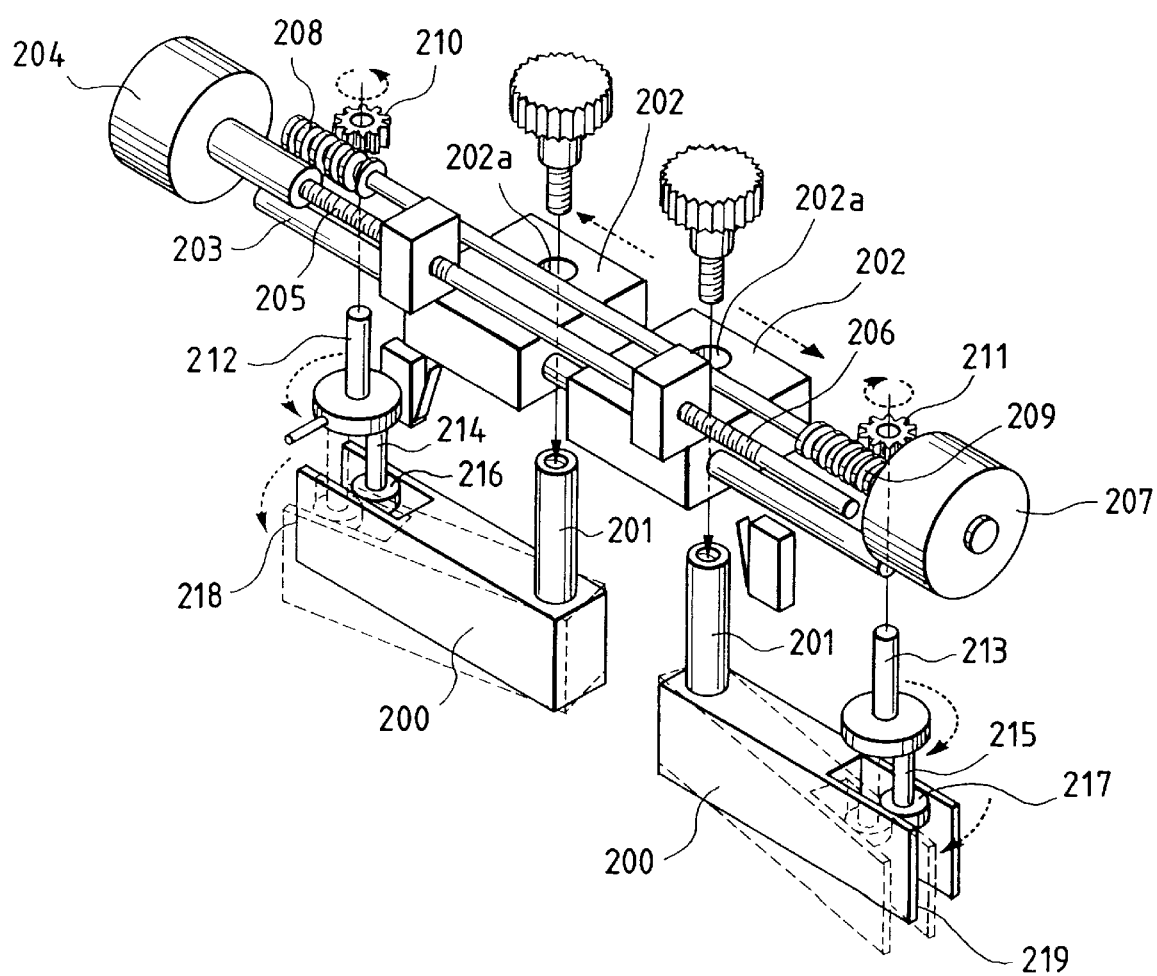
FIG. 2 is a view illustrating a sliding mechanism and a flapping mechanism of lens units.

FIG. 2 is a diagram illustrating the sliding mechanism and the flapping mechanism of the lens units 10. A pair of shafts 201 are respectively fixed to a pair of suspending plates 200 for suspending the respective lens units 10, and each shaft 201 is inserted in a hole 202a formed in each of a pair of slide bases 202 and is rotatable for the flapping operation. The slide bases 202 are slidable in the axial direction of a fixed guide 203, and both a drive motor 204 for sliding and the fixed guide 203 are fixed to an unillustrated fixing bracket. Externally threaded portions 205 and 206 having mutually different threading directions are formed on a shaft which is coupled to the drive motor 204, and the externally threaded portions 205 and 206 mesh with internal threads formed in the slide bases 202. Consequently, as the drive motor 204 is rotated, the two slide bases 202 move in mutually opposite directions. Thus, the interval between the left and right lens units 10 can be adjusted, and the distance between the optical axes of the optical systems disposed in the test windows 11 can be adjusted to the interpupillary distance of the subject.

Numeral 207 denotes a drive motor for flapping, and worms 208 and 209 having mutually different threading directions are fixed to a rotating shaft of the drive motor 207 for flapping. Wheels 210 and 211 which mesh with these worms are respectively fixed to rotatable shafts 212 and 213. Eccentric shafts 214 and 215 and bearings 216 and 217 are respectively disposed at lower ends of the rotatable shafts 212 and 213, and the bearings 216 and 217 are respectively engaged in grooves 218 and 219 formed in the suspending plates 200. Consequently, as the drive motor 207 rotates, the left and right lens units 10 are flapped in mutually opposite directions via the suspending plates 200.

Figure 3:
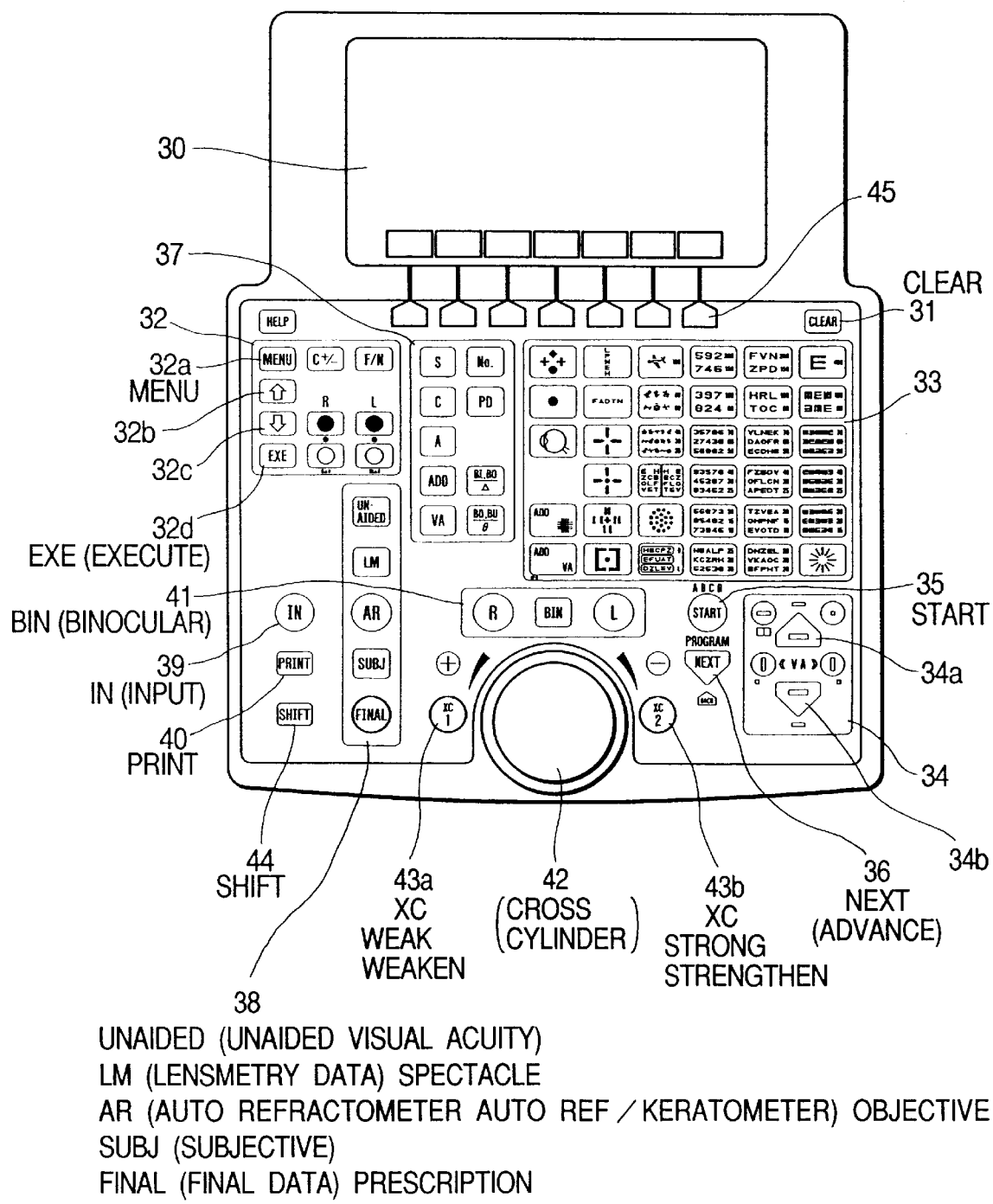
FIG. 3 is a top view of a controller 5.

FIG. 3 is a top view of the controller 5.

Reference numeral 30 denotes a liquid-crystal display which displays optometric information. Numeral 31 denotes a switch section which is provided with the following switches: a group of setting changeover switches 32 having switches which are used when changing over a display screen to a menu screen of the display 30 and effecting such as the setting of parameters; a group of target (chart) switches 33 for changing over a target (chart) to be presented from the target (chart) presenting device 4; a group of mask switches 34 for applying a mask necessary for the presented target (chart); a start switch 35 for executing programmed optometry; an advance switch 36 for advancing the item of programmed optometry to an ensuing item; a group of mode-change designating switches 37 for designating a mode of such as measurement data to be changed; a group of input-data designating switches 38 for designating a mode for entering data or a mode for measurement; a data input switch 39 which is used when data from the objective-type ocular refractive-power measuring device, a lens meter, and the like are inputted; a print switch 40; a measurement-eye designating switch 41; and a dial switch 42 which is used when changing measurement values and inputting numerical values.

Reference numerals 43a and 43b denote changeover switches for changing over a cross-cylinder, and these changeover switches 43a and 43b are also used during adjustment of appearances in the stage of prescription. Numeral 44 denotes a shift switch, and if another switch is pressed while this switch is being pressed, a switch function can be added. Numeral 45 denotes a group of function switches which are used when selecting switches corresponding to switch displays which are displayed at predetermined positions in a lower portion of the screen of the display 30.

Figure 4:
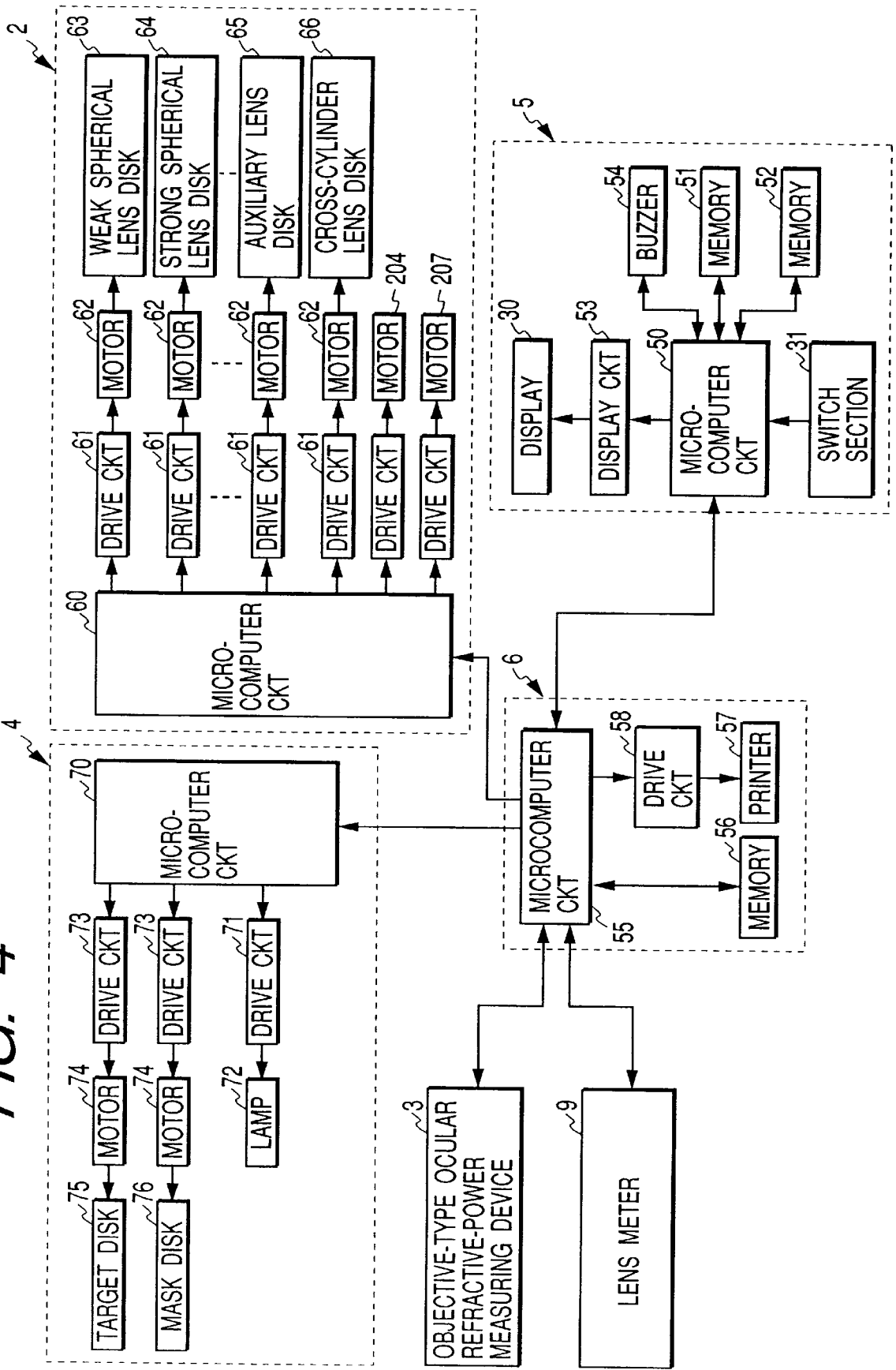
FIG. 4 is a block diagram illustrating the control of the apparatus in accordance with the embodiment.

FIG. 4 is a block diagram for describing the control of the apparatus.

A switch signal from the switch section 31 of the controller 5 is subjected to predetermined processing, and is then inputted to a microcomputer circuit 50. Connected to the microcomputer circuit 50 are a memory 51 for storing a control program such as an optometric program, as well as a memory 52 for storing objective value data and the like. The microcomputer circuit 50 converts the switch signal to various data on the basis of the control program stored in the memory 51, and controls the screen of the display 30 through a display circuit 53. In addition, the converted signal is inputted to a microcomputer circuit 55 of the relay unit 6. The microcomputer circuit 55 supplies data on refractive power and the movement of lens units 10 to the subjective-type refractive-power measuring device 2 and supplies data on the target (chart) to the target (chart) presenting device 4.

A microcomputer circuit 60 of the subjective-type refractive-power measuring device 2 which has received the data on the refractive power drives motors 62 via drive circuits 61 to rotate a weak spherical disk 63, a strong spherical disk 64, an auxiliary lens disk 65, a cross-cylinder disk 66, and the like, thereby disposing predetermined optical systems in the test windows. In addition, the microcomputer circuit 60, upon receiving signals concerning the sliding and flapping of the lens units 10, drives the drive motors 204 and 207.

A microcomputer circuit 70 of the target (chart) presenting device 4 which has received the data on the target (chart) lights up a lamp 72 via a drive circuit 71, drives two motors 74 via two drive circuit 73, and rotates a target (chart) disk 75 with a target (chart) depicted thereon and a mask disk 76, respectively, thereby projecting a predetermined test target (chart) onto an unillustrated screen placed in front of the eye being examined.

The objective-type ocular refractive-power measuring device 3 and a lens meter 9 are connected to the microcomputer circuit 55, and measurement data sent to the microcomputer circuit 55 is stored in a memory 56. When a read command signal is inputted from the microcomputer circuit 50 on the controller 5 side to the microcomputer circuit 55, the microcomputer circuit 55 reads the designated measurement data from the memory 56 and transfers the same to the controller 5.

Numeral 57 denotes a printer for outputting the results of measurement, and 58 denotes a drive circuit thereof.

A description will be given of the operation of the apparatus having the above-described configuration. Here, a description will be given of the operation using an optometric program in which test items and a test procedure have been set in advance (see FIG. 5).

Figure 6:
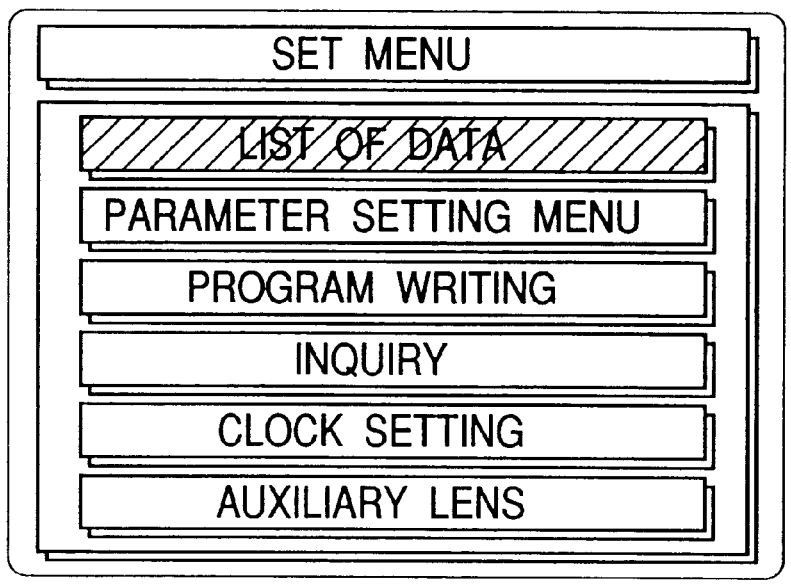
FIG. 6 is a diagram illustrating an example of a menu screen for setting which is displayed on a display.

At the time of examination, when parameters are set and information on an inquiry after the subject is entered, a menu switch 32a of the group of setting changeover switches 32 is pressed. A set menu screen such as the one shown in FIG. 6 is displayed on the display 30. A cursor (the shaded part in FIG. 6) can be moved by move switches 32b and 32c of the group of switches 32, and item of display which the cursor is moved can be selected by an execute switch 32d.

Figure 7:
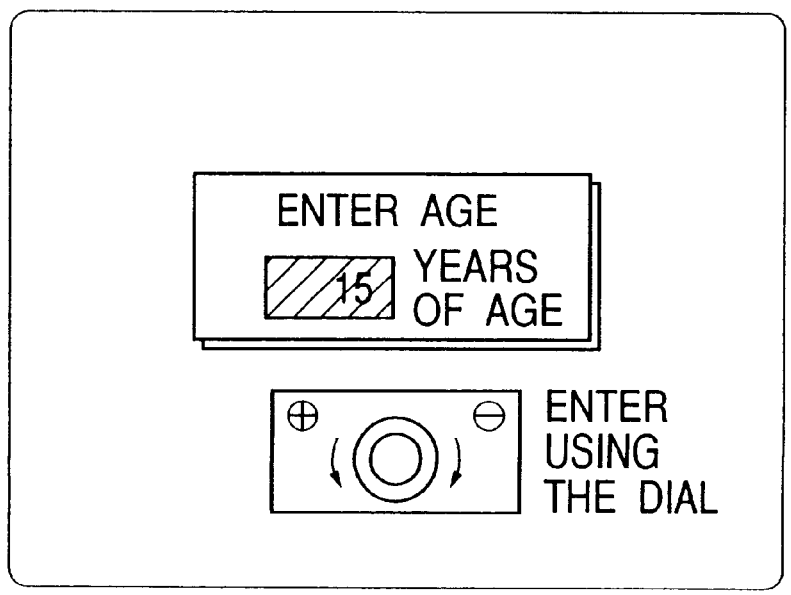
FIG. 7 is a diagram illustrating an example of the screen for inputting age.

If an "inquiry" menu is selected, an inquiry screen is displayed on the display 30. As items of inquiry, those for entering the purpose of making spectacles, age, type of sex, occupation, hobbies, history of spectacles, history of contact lenses, and the like have been prepared. When selecting an item, a cursor is moved by means of the move switches 32b and 32, and an item is selected by the execute switch 32d. When an item for entering age, for example, is selected, the screen is changed over to an age input screen such as the one shown in FIG. 7. The age is entered by making a change by rotating a dial switch.

<Execution of Optometric Program>

Upon completion of the setting of necessary parameters and the entry of inquiry information, the start switch 35 is pressed to execute the optometric program. A message prompting the entry of measurement data by means of the objective-type ocular refractive-power measuring device 3 is displayed on the display 30.

<Input of Objective Value Data>

Various objective value data such as S (SPH: power of the spherical lens (spherical power)), C (CYL: power of astigmatism (cylindrical power)), A (AXIS: angle of astigmatic axis (cylindrical axis)), and the like which are obtained from the objective-type ocular refractive-power measuring device 3 are stored in the memory 56 via the microcomputer circuit 55 of the relay unit 6 by pressing the print switch of the objective-type ocular refractive-power measuring device 3. Subsequently, if the data input switch 39 of the controller 5 is pressed, and the objective switch of the group of input-data designating switches 38 is then pressed, the objective value data stored in the memory 56 are transferred to and stored in an objective value memory area of the memory 52 on the controller 5 side.

It should be noted that the input of the objective value data may be effected manually by the operation of the group of mode-change designating switches 37, the dial switch 42, or the like apart from the data transfer through communication.

Upon completion of the input of the objective value data, the apparatus determines whether or not the case under examination is a hyperopic case. As to whether or not the case is a hyperopic case, the case is determined to be a hyperopic case when, for instance, a spherical equivalent value (SE value) is a plus or a minus of a weak power such as −0.50 D. If the spherical equivalent value in objective measurement is a minus of a weak power in objective measurement, there are cases where measurement is made in a state in which accommodative power is functioning, so that there is a need to hold a doubt that the case may actually be a hyperopic case. In a hyperopic case, a message to the effect that "Exercise caution to intervention by accommodation, particularly in the case of a young subject" is displayed for a number of seconds. The reason for this is that if a hyperopic eye is intervened by the accommodative power, there are cases where it is impossible to obtain accurate test results, so that more caution should be exercised in the prescription of spectacles. The accommodative power is liable to function in the hyperopia of a young subject (about 15 years of age or younger), in which case it is difficult to perform optometry accurately, and there are cases where it is desirable to conduct the test after having a measure, such as the administration of a cycloplegic agent, provided by an ophthalmologist. Such a display makes it possible to prompt even an unskilled examiner to exercise caution, so that the examiner is capable of readily providing measures necessary for future tests (e.g., setting the amount of fogging to a level greater than normal, extending a fogging period, and referral to an ophthomologist).

Incidentally, values for determining whether or not the case is a hyperopic case (in terms of the SE value, −0.25 D, −0.50 D, −0.75 D, etc.) can be set in advance in the setting of parameters.

In addition, the display to the effect of prompting the exercise of caution to the intervention by accommodation may be effected only when the age of the subject which has been entered is a predetermined age or below. In this case, whether to provide a display depending on the inputted age is set in advance in the setting of parameters. Further, an arrangement is also provided that the predetermined age can be set in advance.

<Testing of Unaided Visual Acuity>

Figure 8:
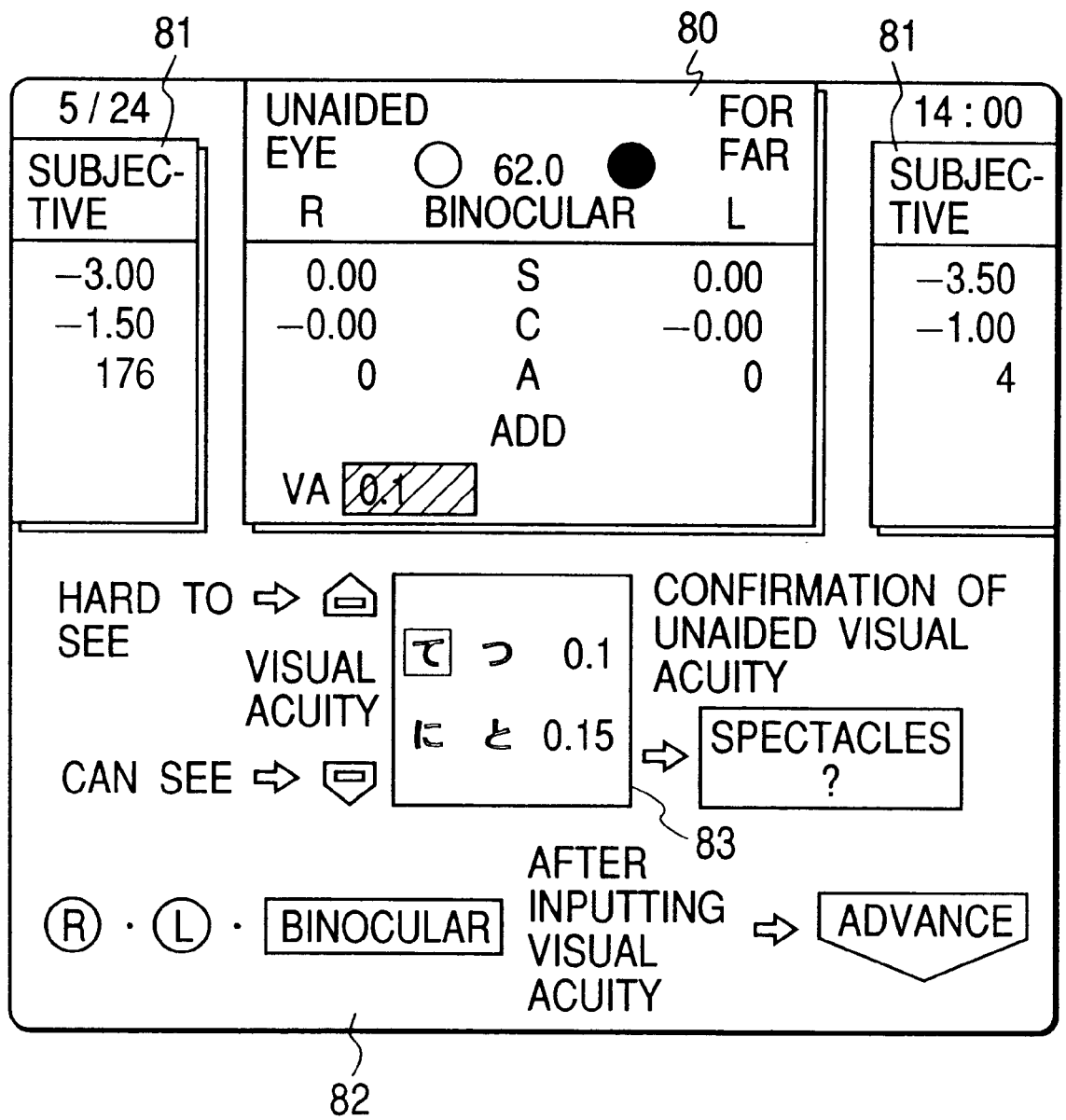
FIG. 8 is a diagram illustrating an example of the screen at the time of starting the unaided visual acuity test.

Upon completion of the input of objective value data, the objective value data is automatically copied to a subjective value memory area, and the last copied data (subjective value data=objective value data) is displayed in left and right display portions 81 in an example of the screen shown in FIG. 8. Subsequently, in terms of the test item, the operation proceeds to the testing of unaided visual acuity. The display screen of the display 30 is set to a mode in which the value of unaided visual acuity of the right eye can be automatically entered, and the subjective value data shifts to the left and right display portions 81. FIG. 8 is an example of display at this time. A present test item is displayed in a central display portion, and entry can be made for a measurement item which is reversely displayed.

This apparatus has the function of calculating a value of unaided visual acuity which is estimated on the basis of the objective value data, and when the testing of unaided visual acuity is started, an operation signal is issued to the target (chart) presenting device 4 to present a test target (chart) having a calculated value of estimated vision. An estimated value of unaided visual acuity is displayed in the VA column of the central display portion 80, and a target (chart) pattern 83 which is being presently presented is displayed in an operation explanation area 82 below the central display portion 80. The examiner applies a mask to the target (chart) by using switches 34*a* and 34*b* of the group of mask switches 34 on the basis of response from the subject, obtains a value of unaided visual acuity of the eye being measured by changing the presented target (chart), and inputs the same. In this case, the test may be conducted by causing the subject to hold an eye cover without disposing the subjective-type refractive-power measuring device 2 in front of the eye being examined, or the test window of the measurement eye side may be opened with the other eye covered.

After the testing of the unaided visual acuity of the right eye is finished, an L switch of the measurement-eye designating switch 41 is pressed so as to test the unaided visual acuity of the left eye in a similar manner. At this time as well, if the objective value data of the left eye is a hyperopic case, a display is given on the screen to that effect. In addition, as a test target (chart) which is presented at this time, one which is different from the one for the right eye is automatically selected.

Subsequently, a binocular switch of the measurement-eye designating switch 41 is designated, and the testing of unaided binocular visual acuity is performed. A highest value of visual acuity between the right and left eye is automatically displayed in the VA column of the central display portion 80, and the testing can be started from that value.

<Input of Spectacle Data>

After the unaided binocular visual acuity has been inputted, the advance switch 36 is pressed to proceed to an ensuing test item. A message to the effect that the presence or absence of spectacles (including contact lenses) should be confirmed is displayed on the display 30, and the designation of switch operation based on the presence or absence of spectacles is displayed below the screen. If the function switch 45 for the presence of spectacles is pressed in compliance with the instruction, the mode is changed over to one in which the spectacle power data can be entered. In the same way as the objective value data, the entered spectacle power data is transferred from the lens meter 9 to the memory 56 and is stored therein, and if the input switch 39 and a spectacle switch of the group of switches 38 are pressed, the spectacle power data is stored in a former-spectacle memory area of the memory 52 (or may be manually entered by operating the dial switch 42 or the like).

It should be noted that in a case where the powers of spectacles have been entered in advance prior to the start of testing, this stage of input of spectacle data is omitted.

<Testing of Spectacled Visual Acuity>

After the spectacle power data has been inputted, the screen of the display 30 is changed over to a mode of testing for confirmation of the spectacled visual acuity of the right eye. Since optical systems corresponding to the spectacle power data are disposed in the test windows of the subjective-type refractive-power measuring device 2, the test may be conducted by disposing the subjective-type refractive-power measuring device 2 in front of the subject's eyes. An estimated visual acuity value based on the residual power due to the difference between the objective value data and the spectacle power data is displayed in the VA column for the right eye in the central display portion 80, and a signal is issued to the target (chart) presenting device 4 to present a test target (chart) having that visual acuity value. A visual acuity value is obtained by changing over the presented target (chart) by means of the switches 34*a* and 34*b* on the basis of the response from the subject, and that value is inputted. If the test is conducted for the left eye and both eyes in a similar manner, visual acuity values are inputted in the same way as in the case of the testing of unaided visual acuity.

<Confirmation of Visual Acuity Based on Objective Value Data>

Then, if the advance switch 36 is pressed, the operation proceeds to the testing for confirmation of objective visual acuity for confirming the appropriateness of the objective value data. Optical systems corresponding to the objective value data are initially set in the test windows of the lens units 10, so that the state is set for allowing the right eye to be examined. The examiner disposes the subjective-type refractive-power measuring device 2 in front of the subject's eyes. From the target (chart) presenting device 4, test targets (charts) provided in a set of targets (charts) with visual acuity values ranging from 0.5 to 0.7 are presented with vertical masks applied thereto. The testing for confirmation of the subjective visual acuity in the prescription of spectacles is carried out primarily for the purpose of confirming the reliability of objective value data and the presence of any abnormality in the visual function, such as amblyopia, in the eye being examined. Therefore, a target (chart) having a minimum visual acuity value of 0.5, which serves as a reference for this confirmation, is initially presented in this apparatus. If the eye being examined is unable to discern the target (chart) with the visual acuity value of 0.5, necessary measures are taken such as the reconducting of objective measurement and close examination.

<Test for Determining Values of Monocular Complete Correction>

Figure 9:
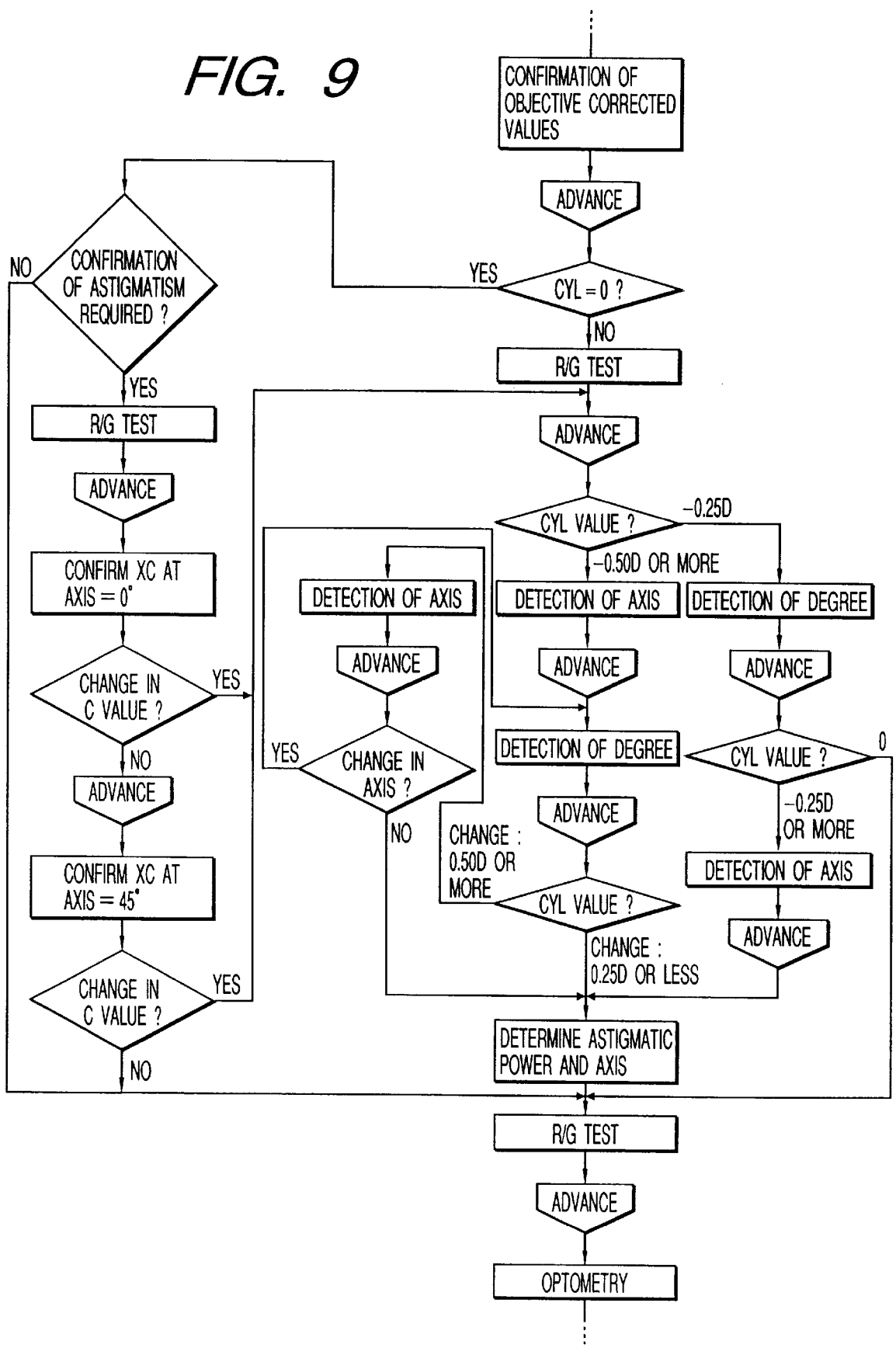
FIG. 9 is a diagram illustrating a test flow in an astigmatism (cylinder) test.
Figure 10:
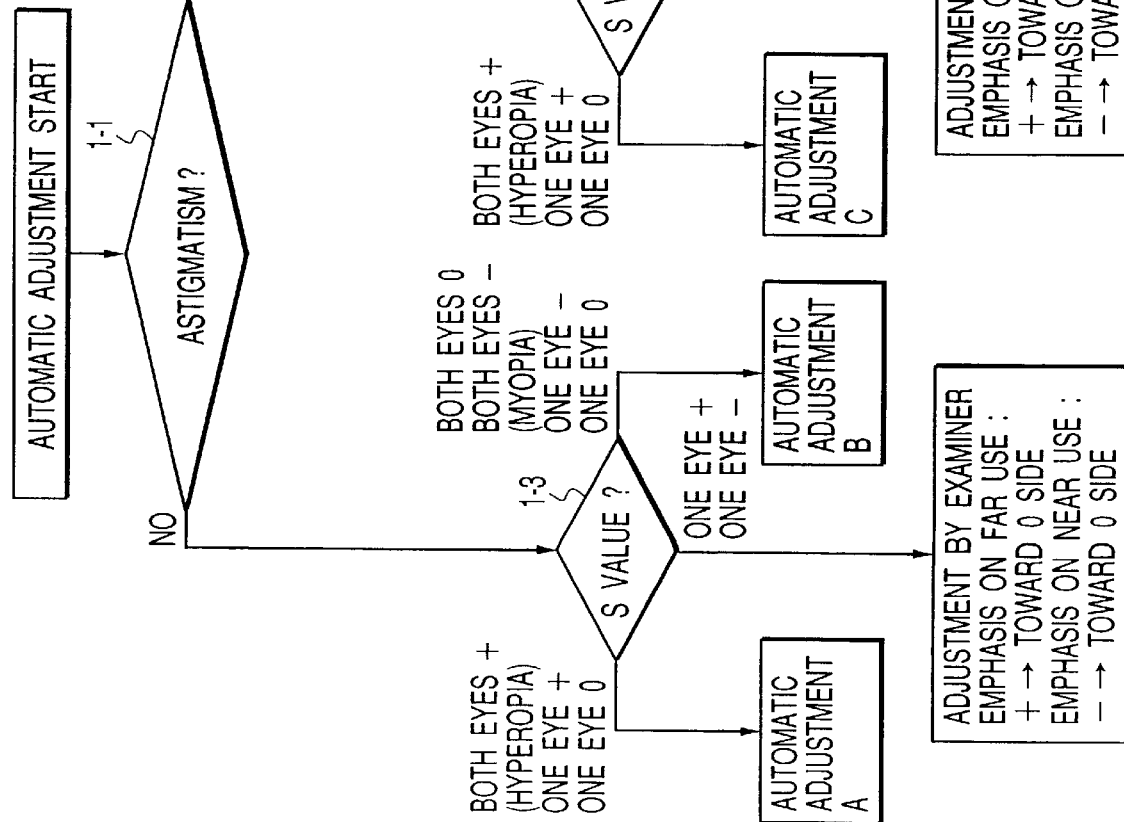
FIG. 10 is a flowchart illustrating a program for automatically adjusting correction power for far use.
Figure 11:
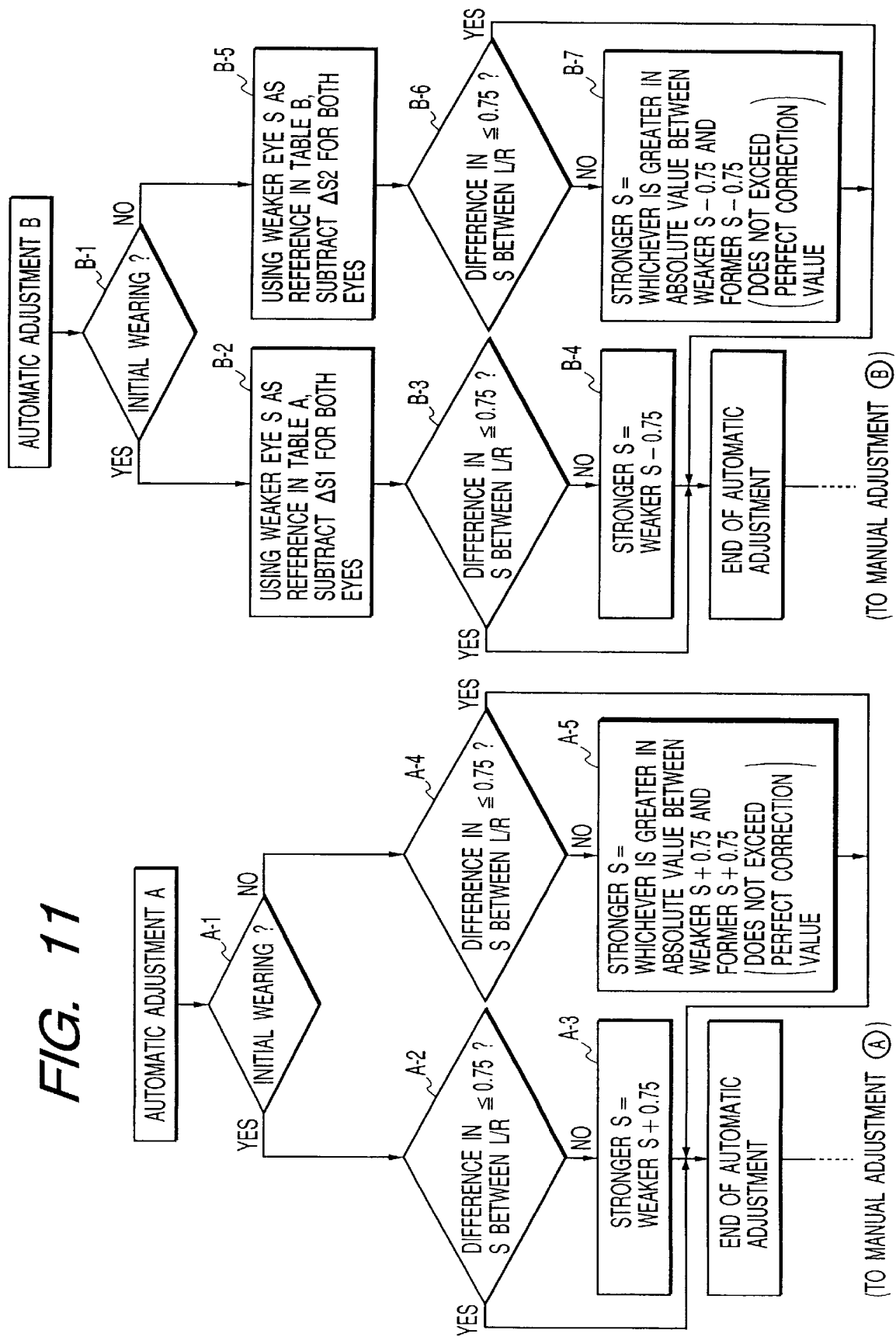
FIG. 11 is a flowchart illustrating the program for automatically adjusting correction power for far use.
Figure 12:
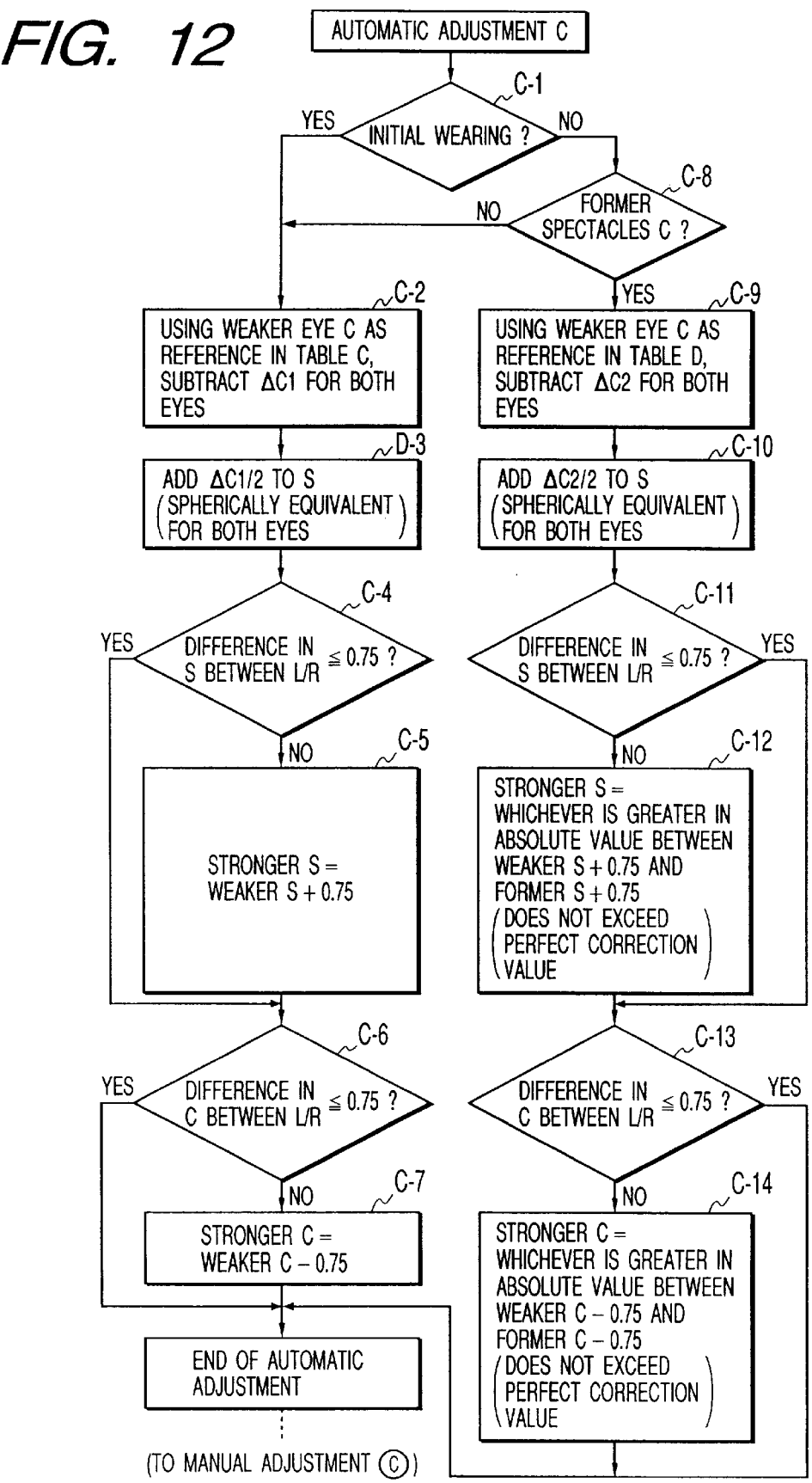
FIG. 12 is a flowchart illustrating the program for automatically adjusting correction power for far use.
Figure 13:
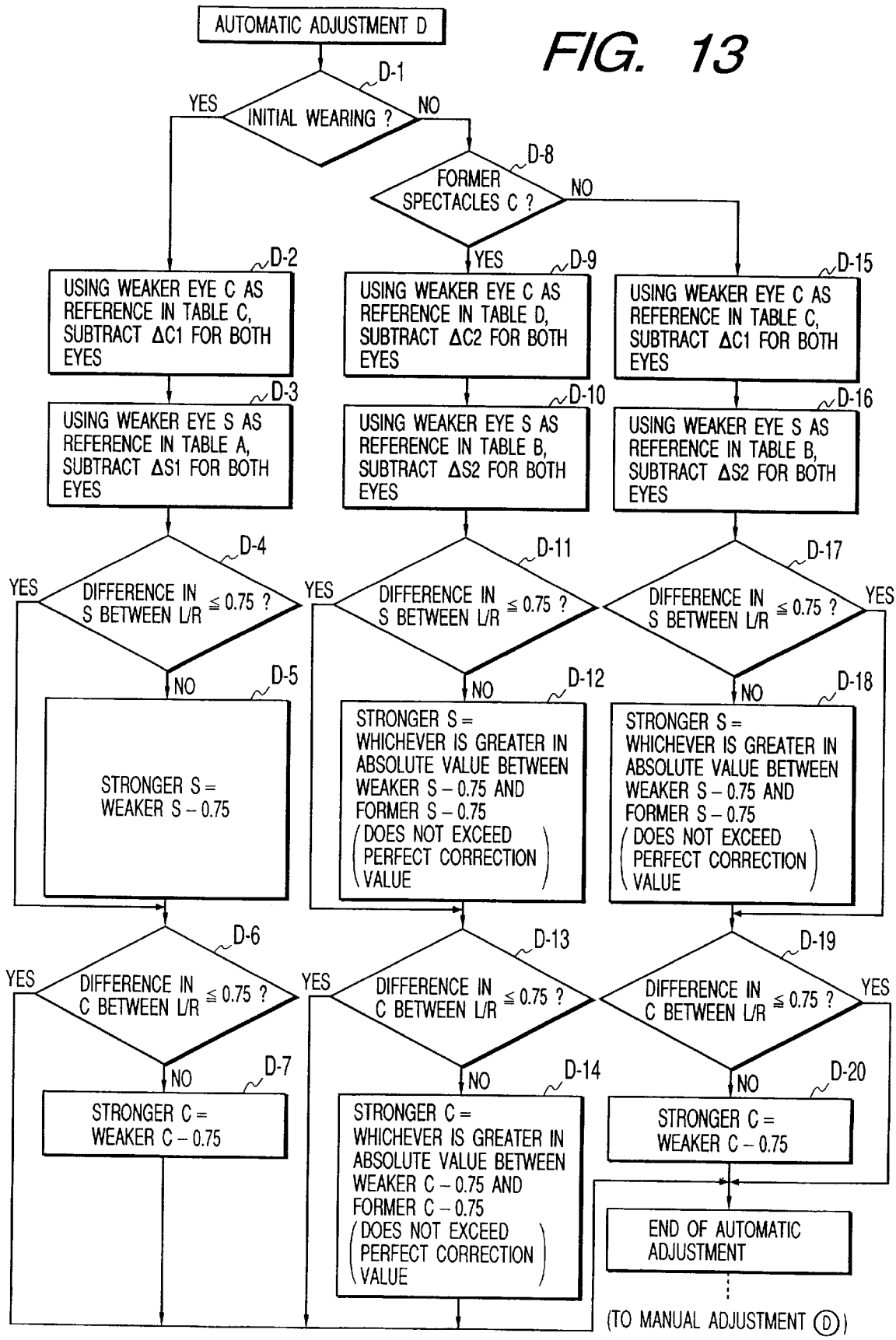
FIG. 13 is a flowchart illustrating the program for automatically adjusting correction power for far use.
Figure 14:
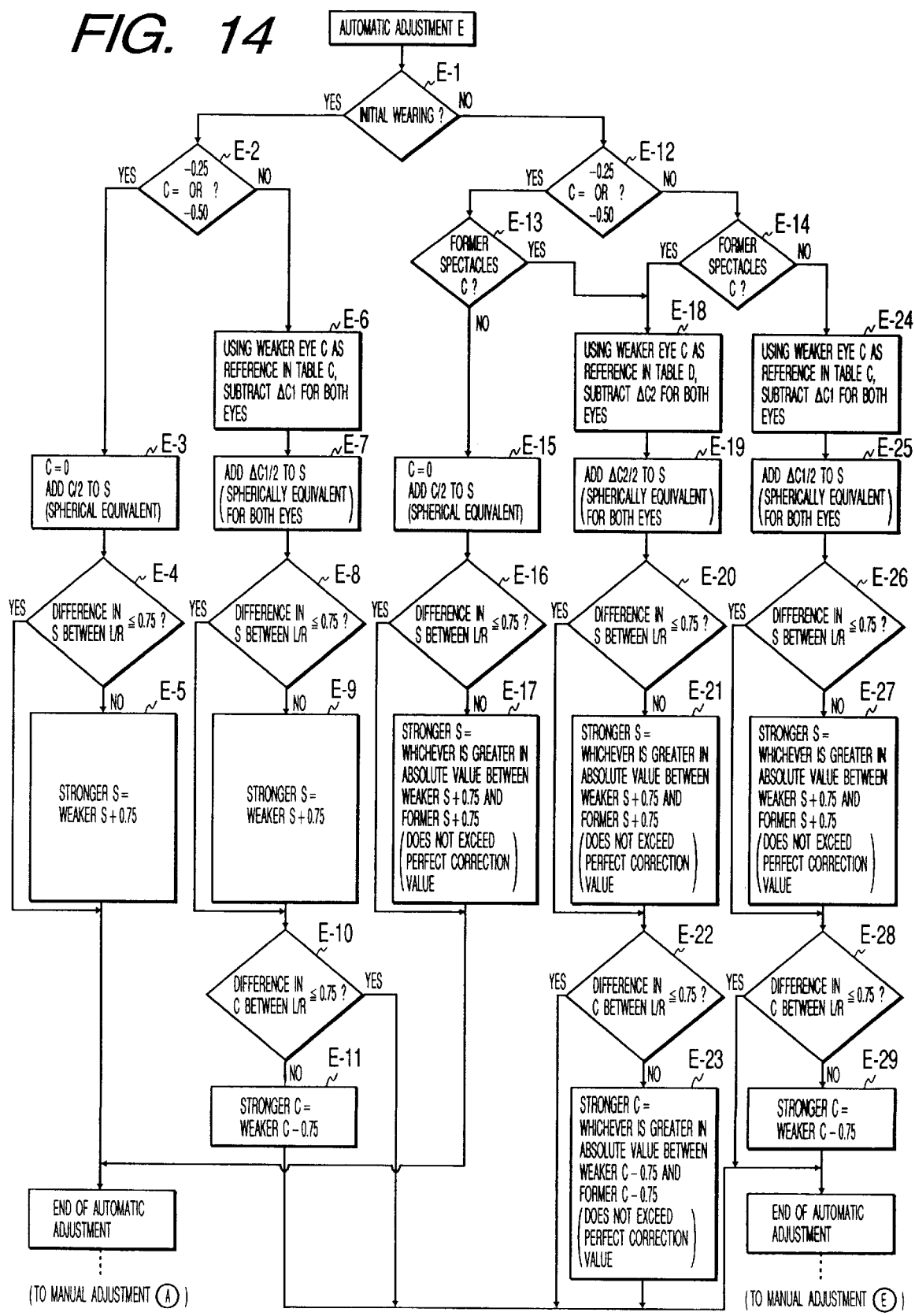
FIG. 14 is a flowchart illustrating the program for automatically adjusting correction power for far use.
Figure 15:
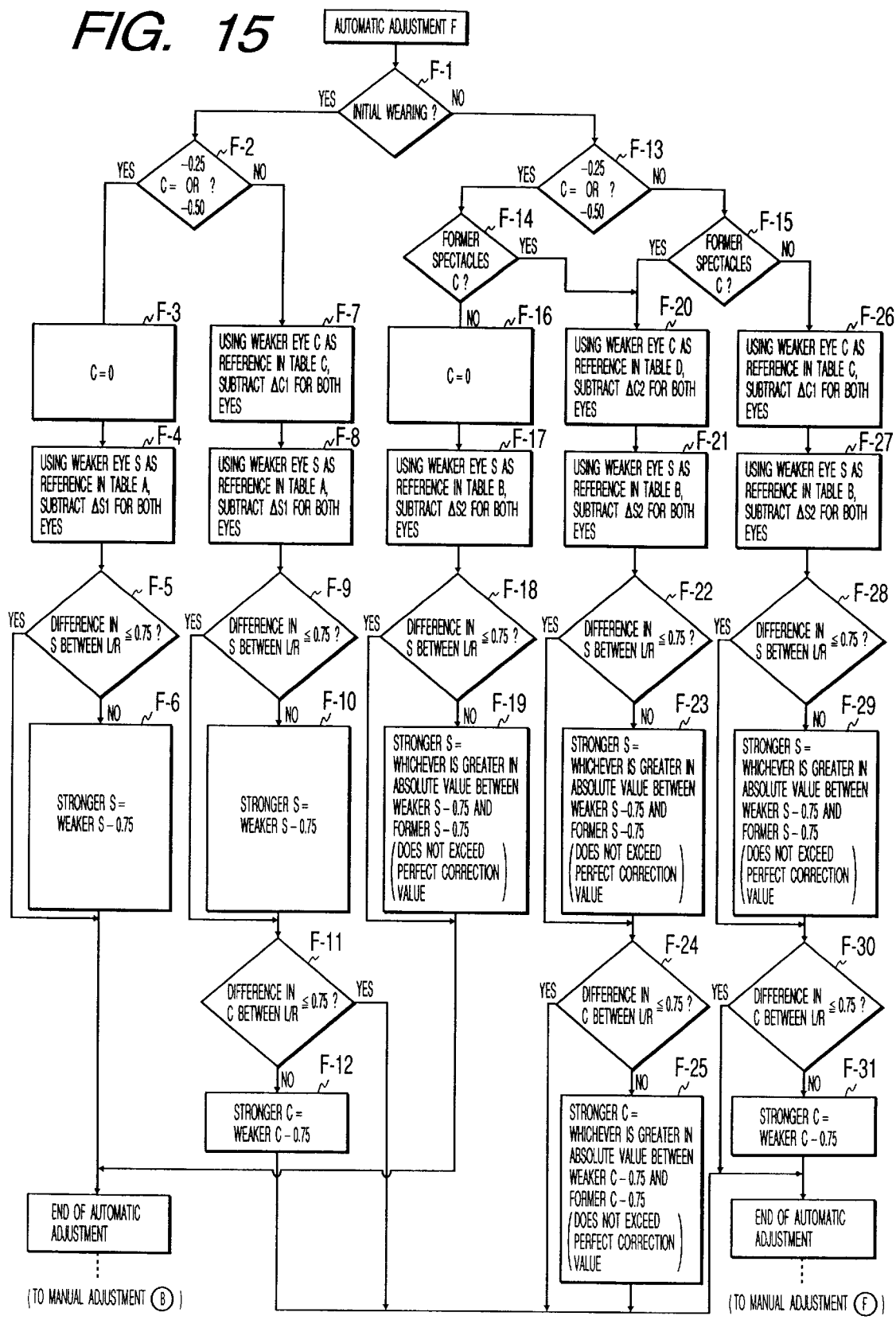
FIG. 15 is a flowchart illustrating the program for automatically adjusting correction power for far use.

If the presented target (chart) is legible in the test for confirmation of objective visual acuity, the advance switch 36 is pressed to proceed to the ensuing test for determining values of monocular complete correction. This test is effected in the order of a first R/G (red/green) test which is generally carried out before the testing of astigmatism, an astigmatic- (cylindrical-) axis adjustment test, an astigmatic- (cylindrical-) power adjustment test, a second R/G test for obtaining maximum visual acuity while preventing over correction, and optometry. However, this apparatus has a program for changing the test procedure on the basis of the C value of the inputted objective value data (or the C value of the spectacle power data may be used) (see FIG. 9). Depending on whether the C value of the objective value data is less than or equal to a first predetermined reference value (CYL=0), the test procedure proceeds as described below.

[A: When CYL=0]

A message is displayed on the screen of the display 30 to the effect that confirmation is to be made as to whether or not to effect confirmation of astigmatism, and an operational instruction, "YES" or "NO," for responding to it is displayed in a lower portion of the screen. The examiner makes entry by pressing a relevant function switch 45 which corresponds to the operational instruction.

[A-1] In a case where the confirmation of astigmatism is not to be carried out, if the "NO" switch is pressed, the first R/G test, the astigmatic- (cylindrical-) axis adjustment test, and the astigmatic- (cylindrical-) power adjustment test are omitted, and the test step proceeds to the second R/G test. If astigmatism does not appear in the objective value data, astigmatism is frequently not detected in the subjective tests as well. Therefore, it is possible to enhance the testing efficiency by omitting useless test items without conducting many troublesome switch operations.

[A-2] When the presence of astigmatism is suspected or accuracy is to be ensured, the confirmation of astigmatism is carried out. If the "YES" switch is pressed, the operation proceeds to the step of the first R/G test. In the test window of the subjective-type refractive-power measuring device 2, fogging is provided by imparting a spherical power of +0.50 D to the optical system set at an initial value so as to eliminate intervention by the accommodation of the eye being measured. The amount of fogging is displayed on the display screen. A predetermined red-green target (chart) is presented from the target (chart) presenting device 4, and Be the controller 5 is set in a mode in which the spherical power can be changed. The examiner adjusts the spherical power by operating the dial switch 42 on the basis of the subject's response on appearances, such that the letters in red and green in the red-green target (chart) can be viewed at the same power or the green side can be viewed slightly better, by way of an attempt to locate the circle of least confusion in the vicinity of the retina.

Upon completion of the adjustment of the spherical power in the first R/G test, if the advance switch 36 is pressed, the operation proceeds to a test for confirmation of the power by means of a cross-cylinder lens (hereafter, XC lens) at an astigmatic axis=0°. A spot-group target (chart) is presented as the test target (chart), and the controller 5 is set in a mode in which the power of astigmatism can be changed. The XC lens is set in the test window of the subjective-type refractive-power measuring device 2 with a minus axial angle set at 90°. The examiner inverts the XC lens by means of the changeover switches 43a (this switch sets the minus axis to 90°) and 43b (this switch sets the minus axis to 180°) so as to allow the subject to confirm the difference in the appearance. Then, the dial switch 42 is rotated toward the side for which a response that better vision is obtained has been given, so as to obtain a change in the C value. When the pressing of the switch 43a gives better vision, if the dial switch 42 is rotated counterclockwise by one click, the C value becomes −0.25 D, while the A value becomes 90°. Conversely, when the pressing of the switch 43b gives better vision, if the dial switch 42 is rotated clockwise by one click, the C value becomes −0.25 D, while the A value becomes 0°. Subsequently, the operation proceeds to the step for the case where CYL≠0.

Here, when there is no change in the C value, the advance switch 36 is pressed to proceed to a test for confirmation of the power with the astigmatic (cylindrical) axis set to 45°. The minus axial angle of the XC lens is set to 135°. This is effected to confirm the presence of astigmatism in an oblique direction. Similarly, the examiner inverts the XC lens to allow the subject to confirm the difference in the appearance. In this test as well, if there is no change in the C value, it can be determined that astigmatism is not present, and it is assumed that close examination of astigmatism is unnecessary, so that the operation proceeds to the second R/G test. If there is a change, the operation proceeds to the step for the case where CYL≠0.

[B: When CYL≠0]
As a result of determination by the apparatus, the operation proceeds to the step of the first R/G test. In the same way as described above, the examiner adjusts the spherical power and makes an attempt to locate the circle of least confusion in the vicinity of the retina.

Upon completion of the first R/G test, if the advance switch 36 is pressed, the test procedure is altered as described below as a result of determination by the apparatus as to whether or not the C value of the objective value data is greater than or equal to a second predetermined reference value (hereafter, this value will be set at −0.50 D). It should be noted that the C value which is "greater than or equal to" the second predetermined reference value is meant to include both a minus reading and a plus reading, and refers to one whose absolute value is greater.

[B-1] If the C value is greater than or equal to −0.50 D, the operation proceeds in the order of the astigmatic- (cylindrical-) axis adjustment test and the astigmatic- (cylindrical-) power adjustment test.

In the astigmatic- (cylindrical-) axis adjustment test, the controller 5 is set in a mode in which the astigmatic (cylindrical) axis can be changed, and the XC lens is set in the test window of the subjective-type refractive-power measuring device 2 in a state in which the axis of inversion is adjusted to the astigmatic (cylindrical) axis of the objective value data. A spot-group target (chart) is presented as the test target (chart). The examiner inverts the XC lens by means of the changeover switches 43a and 43b to allow the subject to confirm the difference in the appearance, and moves the axis of inversion until the test target (chart) is viewed substantially uniformly before and after the inversion. In the apparatus of this embodiment, the axis of inversion is moved in a predetermined angular step by rotating the dial switch 42 toward the switch 43a or 43b side for which a response that better vision is obtained has been given, thereby making it possible to obtain an angle of astigmatic (cylindrical) axis.

Concerning the movement of the axis of inversion of the XC lens at this time, the apparatus has a program for changing the step of the adjusting angle of the astigmatic (cylindrical) axis depending on whether or not the C value of the objective value data (or the C value of the spectacle power data) is greater than or equal to a third predetermined reference value. For example, when the C value of the objective value data is greater than or equal to −1.25 D, the axis of inversion is moved in steps of 1°, and when it is less than −1.25 D, the axis of inversion is moved in steps of 5°. In cases where the C value is relatively small, the axis is not detected stably even if the axis is detected in fine angular steps, so that it is of little significance to do so. On the other hand, if the C value is large, there are many cases where the axis can be detected accurately at fine angular steps of 1°. Therefore, since the apparatus automatically sets this change on the basis of the C value of the objective value data, the examiner is dispensed from altering the setting for each C value during the test, and even an unskilled examiner is able to proceed with the test readily and efficiently. Incidentally, the examiner is able to set in advance the criteria of determination by the apparatus. This is effected by operating the group of setting changeover switches 32 among the items of parameter setting in the menu screen. Further, depending on the examiner's policy of examination, 5° or 1° may be constantly fixed without making a change based on the C value, or may be changed over in the course of the examination.

Upon completion of the astigmatic- (cylindrical-) axis adjustment test, if the advance switch 36 is pressed, the operation proceeds to the astigmatic- (cylindrical-) power adjustment test. The plus axis of the XC lens is set in the test window of the subjective-type refractive-power measuring device 2 in conformity with the obtained astigmatic (cylindrical) axis. The examiner obtains the power of astigmatism (cylinder) by making an adjustment by increasing or decreasing the C value depending on the appearance before and after the inversion of the XC lens.

Upon completion of the astigmatic- (cylindrical-) power adjustment test, if the advance switch 36 is pressed, the apparatus makes a comparison between the obtained power of astigmatism (cylinder) and that of the objective value data. In cases where the variation of the power between them is less than or equal to 0.25 D, the obtained values are determined as the astigmatic (cylindrical) axis and the power of astigmatism (cylinder). However, in cases where the variation of the power is greater than or equal to 0.50 D, the operation returns to the astigmatic- (cylindrical-) power adjustment test. The reason for this is that such a large change in the power that causes the power of astigmatism (cylinder) to change by two steps or more has a large possibility of causing a variation in the axis. If there is no variation with respect to the value of the astigmatic (cylindrical) axis obtained in the previous astigmatic- (cylindrical-) axis adjustment test, the obtained values are determined as the power and the axis of astigmatism (cylinder), and the operation proceeds to the second R/G test. If there is a variation, the operation returns to the astigmatic- (cylindrical-) power adjustment test.

[B-2] If the C value is less than −0.50 D (i.e. it is −0.25 D), the astigmatic- (cylindrical-) power adjustment test is conducted prior to the astigmatic- (cylindrical-) axis adjustment test. The reason for this is because there is a possibility that the power of astigmatism (cylinder) is 0 in the test for detecting the power of astigmatism (cylinder), and because if the power of astigmatism (cylinder) is 0, the astigmatic- (cylindrical-) axis test is unnecessary. (If the test for detecting the axis is conducted first, and the power of astigmatism (cylinder) is 0, the test of the axis is wasted.)

If CYL=0 as a result of this test, the test for detecting the axis is unnecessary. Hence, the advance switch is pressed to proceed to the second R/G test by omitting the detection of the astigmatic (cylindrical) axis (by providing a setting such that AXIS=0). If the C value is greater than or equal to −0.25 D, the astigmatic- (cylindrical-) axis test is subsequently conducted, and the power and the axis of astigmatism (cylinder) are determined.

When the adjustment of the power and the axis of astigmatism (cylinder) is completed and their values are determined as described above, the operation proceeds to the second R/G test. A spherical power of +0.50 D is imparted to the test window of the subjective-type refractive-power measuring device 2 to provide fogging. The amount of fogging is displayed on the display screen. A predetermined red-green target (chart) is presented as the target (chart) from the target (chart) presenting device 4. Since the controller 5 is set in a mode in which the spherical power can be changed, the examiner adjusts the spherical power by operating the dial switch 42 on the basis of the subject's response on the appearance, such that the letters in red and green can be viewed at the same power or the red side can be viewed slightly better.

Upon completion of the second R/G test, if the advance switch 36 is pressed, the operation proceeds to optometry. Test targets (charts) provided in a set of targets (charts) having a visual acuity value of 1.0 are presented with horizontal masks applied thereto. When the highest visual acuity is determined, the examiner adjusts the spherical power, and sets a power which gives the highest visual acuity which is maximally on the plus side, so as to determine completely corrected values for one eye.

When the perfect correction values for one eye have been determined, the advance switch 36 is pressed to proceed to the test for obtaining perfect correction values for the other eye. If a maximum visual acuity value of the eye being examined which is inputted at this time is less than 0.7, a message is displayed on the screen to the effect that readjustment of S, C, and A is prompted by confirming the visual acuity by a pin-hole test. An operational instruction, "YES" or "NO," for responding to it is displayed in the lower portion of the screen. If the pin-hole test is required, a designation is given by means of the function switch 45 corresponding to the operational instruction (alternatively, the message to the effect that the pin-hole test is prompted may be simply displayed for a number of seconds, and the subsequent operation may be left to the discretion of the examiner). If "YES" is designated, a pin-hole plate is set in the test window of the subjective-type refractive-power measuring device 2. The-eye being measured is allowed to view the optometric target (chart) through the pin hole, and confirmation is made as to whether or not visual acuity has improved. Since an operational instruction, "YES" or "NO," for inquiring whether or not visual acuity has improved is displayed in the lower portion of the screen, so that the function switch 45 is pressed in compliance with the operational instruction.

If "NO" is pressed, a message is displayed to the effect that close examination of such as the cornea and the retina is required. In the pin-hole test as well, in a case where there is no change in visual acuity, not only a correction error but also other factors of abnormality in such as the cornea, the retina, and optic nerves are conceivable. As a result, the examiner adopts a necessary measure such as close examination.

If "YES" is inputted, the test item returns to the test for confirmation of visual acuity on the basis of objective value data, which is an initial stage of the subjective examination. When visual acuity improves in the pin-hole test, there is a possibility that perfect correction was insufficient, so that the perfect correction test is conducted again.

If 0.7 is obtained as a highest visual acuity value of one eye, the advance switch 36 is pressed to proceed to the test for obtaining perfect correction values for the other eye. The examiner obtains perfect correction values for the other eye in a similar manner.

<Binocular Balance Test>

When perfect correction values are obtained for each eye, the advance switch 36 is pressed to proceed to a binocular balance test. Polarizing plates are disposed in the test windows of the subjective-type refractive-power measuring device 2, and a spherical power in an amount of fogging for setting the value of perfect correction visual acuity to 0.8 or thereabouts is imparted to provide fogging. The amount of fogging is displayed on the display screen. In addition, values obtained in the monocular perfect correction are copied in the central display portion 80 on the screen, and the operation is set in a mode in which the spherical powers of both eyes can be inputted. Values obtained in the perfect correction, including visual acuity values, are transcribed to the left and right display portions 81. Binocular balance targets (charts) are presented as the test targets (charts).

The subject is allowed to confirm the difference in appearances in the left and the right eyes using the binocular balance targets (charts). If there is a difference, the eye which give better vision is designated by means of the R switch or the L switch of the measurement-eye designating switch 41, and balance correction for adding S+0.25 D is effected. At this time, unaided visual acuity values and visual acuity values based on the former spectacles are displayed in the lower portion of the central display portion 80. If vision by the eyes which have been corrected by the balance correction is less sharp, reference is made to this information, and priority is placed on the visual acuity values which are based on the former spectacles and give better vision (in the case of a subject wearing the spectacles for the first time, priority is placed on the unaided visual acuity values which give better vision). In addition, since there are cases where the determination of balance correction is made by the dominant eye, it is convenient to input and store dominant eye information in advance in the memory, and display the same on the screen.

Thus, values of binocular perfect correction are obtained (in this specification, those perfect correction values which are obtained after conducting the binocular balance test are referred to as the values of binocular perfect correction).

<Test for Confirming Stereoscopic Vision>

Upon completion of adjustment of the binocular balance, the advance switch 36 is pressed to proceed to the test for confirming stereoscopic vision. The fogging with the spherical powers applied during the binocular balance test is removed from the test windows of the subjective-type refractive-power measuring device 2, and a message informing the examiner of the effect that fogging has been removed is displayed in the lower portion of the central display portion 80. Thus, the apparatus automatically cancels the fogging by an input signal from the advance switch 36, and displays to that effect, so that the examiner is able to conduct an ensuing test with appropriate optical systems without needing to remember the cancellation of the fogging.

In the test of stereoscopic vision, stereoscopic targets (charts) are presented. Instructions for operation (1', 2', 4', 10', NG) for inputting stereoscopic parallax are displayed in the lower portion of the screen. Depending on to what extent the stereoscopic parallax can be confirmed by the subject, the examiner presses a function switch corresponding to the operational instruction, and enters the same. This result is printed during printout.

<Adjustment of Correction Powers for Far Use—(1) Automatic Adjustment>

Upon completion of the test for confirming stereoscopic vision, the operation proceeds to adjustment of correction powers for far use for determining rough powers serving as prescription values for far use. This apparatus has an automatic adjustment program whereby, if the values of binocular perfect correction obtained as described above and spectacle values are available, rough powers serving as prescription values which are estimated to be optimal for the subject are automatically calculated on the basis of that data. When the optometric program is in progress, an input signal from the advance switch 36 executes the automatic adjustment program, and rough powers serving as prescription values which are calculated are displayed on the central display portion 80.

Hereafter, referring to flowcharts shown in FIGS. 10 to 15, a description will be given of this automatic adjustment program. It should be noted that the term "a stronger eye" used in the description that follows refers to whichever has a greater absolute value in terms of the power of each of the S value and the C value between the perfect corrected both eyes. Meanwhile, the term "a weaker eye" refers to the opposite of the same. In addition, a minus reading is adopted for astigmatism (cylinder) (C value).

First, the apparatus determines the presence or absence of astigmatism (cylinder) on the basis of the values of binocular perfect correction (Step 1-1). If astigmatism (cylinder) is present, a determination is made as to whether or not astigmatism (cylinder) is oblique astigmatism (cylinder) (AXIS: 15° to 75° or 105° to 165°) (Step 1-2). Subsequently, on the basis of the S values of both eyes a determination is made as to hyperopia (both eyes are plus, or one eye is plus and the other eye is 0) or myopia (both eyes are minus, or one eye is minus and the other eye is 0) (Steps 1-3 to 1-5), so that adjusted powers can be calculated by effecting the processing of one of ensuing power adjustments A to F. When it is impossible to distinguish between hyperopia and myopia (the S value of one eye is plus, and the S value of the other eye is minus), the power adjustment is not effected, and a message is displayed to the effect that the examiner is to make an adjustment.

[Automatic Adjustment A: In the Case of Hyperopia Without Astigmatism (Cylinder)]

On the basis of the presence or absence of the input of spectacle power data (presence or absence of a history of spectacles), the apparatus determines whether or not the subject wears the spectacles for the first time (Step A-1).

[A-1] If the subject wears the spectacles for the first time, the difference between the S values of the left and right eyes is then compared with a reference value (Step A-2). If the difference between the S values of the left and right eyes is within a predetermined power difference (hereafter, a description will be given under the assumption that the difference in the S value or the C value between the left and right eyes is to be adjusted to within 0.75 D), the values of binocular perfect correction are used as they are as adjusted powers. If the difference in the S value between the left and right eyes exceeds 0.75 D, the S value of the stronger eye is set to a value in which +0.75 D is added to the S value of the weaker eye (Step A-3).

[A-2] If the subject does not wear the spectacles for the first time, the difference in the S value between the left and right eyes is compared with the reference value (Step A-4). If the difference between the left and right eyes exceeds 0.75 D, the S value of the stronger eye is set to whichever value having a greater absolute value between a value in which +0.75 D is added to the S value of the weaker eye and a value in which a predetermined power (in the case of a hyperopia, +0.75 D hereafter) is added to the S value of the same side of the former spectacles, such that the value does not exceed the relevant one of the values of binocular perfect correction (Step A-5).

[Automatic Adjustment B: In the Case of Myopia Without Astigmatism (Cylinder)]

A determination is made as to whether or not the subject wears the spectacles for the first time (Step B-1).

[B-1] If the subject wears the spectacles for the first time, correction processing is first carried out in which a correction amount ΔS1 is obtained by calculation in Table A in FIG. 16 by using as a reference the S value of the weaker eye obtained in binocular perfect correction, and the correction amount ΔS1 is subtracted from each of the S values of binocular perfect correction for both eyes (hereafter, this processing will be referred to as correction processing A1) (Step B-2). Next, the difference between the left and right eyes after correction processing is compared with the reference value (Step B-3), and if the difference exceeds 0.75 D, the S value of the stronger eye is set to a value in which −0.75 D is added to the S value of the weaker eye (Step B-4).

[B-2] If the subject does not wear the spectacles for the first time, correction processing is carried out in which a correction amount ΔS2 is obtained by calculation in Table B in FIG. 16 by using as a reference a smaller one of the differences between the former spectacle value and the value of binocular perfect correction in left and right S values, and the correction amount ΔS2 is subtracted from each of the S values of binocular perfect correction for both eyes (hereafter, this processing will be referred to as correction processing B1) (Step B-5). Next, the difference in the S value between the left and right eyes after correction processing is compared with the reference value (Step B-6), and if the difference exceeds 0.75 D, the S value of the stronger eye is set to whichever value having a greater absolute value between a value in which −0.75 D is added to the corrected S value of the weaker eye and a value in which a predetermined power (in the case of a hyperopia, −0.75 D hereafter) is added to the S value of the same side of the former spectacles, such that the value does not exceed the relevant one of the values of binocular perfect correction (Step B-7). [Automatic Adjustment C: In the Case of Hyperopia Having Astigmatism (Cylinder) Which is Not Oblique Astigmatism (Cylinder)]

A determination is made as to whether or not the subject wears the spectacles for the first time (Step C-1).

[C-1] If the subject wears the spectacles for the first time, correction processing is first carried out in which a correction amount ΔC1 is obtained by calculation in Table C in FIG. 16 by using as a reference the C value of the weaker eye, and the correction amount ΔC1 is subtracted from each of the C values of binocular perfect correction for both eyes (hereafter, this processing will be referred to as correction processing C1) (Step C-2). Then, the S values of both eyes are each set to a value in which half of the correction amount ΔC1 is added to the value of binocular perfect correction to obtain a spherical equivalent value (Step C-3). Subsequently, the difference between the obtained S values of the left and right eyes is compared with the reference value (Step C-4), and if the difference exceeds 0.75 D, the S value of the stronger eye is set to a value in which +0.75 D is added to the S value of the weaker eye (Step C-5). Next, the difference in the C value between the left and right eyes after the correction processing C1 is compared with the reference value (Step C-6), and if the difference exceeds 0.75 D, the C value of the stronger eye is set to a value in which −0.75 D is added to the C value of the weaker eye (Step C-7).

[C-2] In a case where the subject does not wear the spectacles for the first time, first, if astigmatism (cylinder) is not present on the basis of the determination of the presence or absence of astigmatism (cylinder) in the former spectacle values (Step C-8), the same power adjustment as in the case of the initial wearing is performed (Steps C-2 to C-7). If astigmatism (cylinder) is present, correction processing is carried out in which a correction amount ΔC2 is obtained by calculation in Table D in FIG. 16 by using as a reference a smaller one of the differences between the former spectacle value and the value of binocular perfect correction in left and right C values, and the correction amount ΔC2 is subtracted from each of the C values of binocular perfect correction for both eyes (hereafter, this processing will be referred to as correction processing D1) (Step C-9). Then, the S values of both eyes are each set to a value in which half of the correction amount ΔC2 is added to the value of binocular perfect correction to obtain a spherical equivalent value (Step C-10). Subsequently, the difference between the obtained S values of the left and right eyes is compared with the reference value (Step C-11), and if the difference exceeds 0.75 D, the S value of the stronger eye is set to whichever value having a greater absolute value between a value in which +0.75 D is added to the S value of the weaker eye made spherically equivalent and a value in which +0.75 D is added to the S value of the same side of the former spectacles, such that the value does not exceed the relevant one of the values of binocular perfect correction (Step C-12). Next, if the difference in the C value between the left and right eyes after the correction processing D1 exceeds 0.75 D (Step C-13), the C value of the stronger eye is set to whichever value having a greater absolute value between a value in which −0.75 D is added to the C value of the weaker eye and a value in which −0.75 D is added to the C value of the same side of the former spectacles, such that the value does not exceed the relevant one of the values of binocular perfect correction (Step C-14). [Automatic Adjustment D: In the Case of Myopia Having Astigmatism (Cylinder) Which is Not Oblique Astigmatism (Cylinder)]

A determination is made as to whether or not the subject wears the spectacles for the first time (Step D-1). [D-1] If the subject wears the spectacles for the first time, the correction processing C1 is carried out (Step D-2), and the correction processing A1 is carried out (Step D-3). Subsequently, the difference between the obtained S values of the left and right eyes is compared with the reference value (Step D-4), and if the difference exceeds 0.75 D, the S value of the stronger eye is set to a value in which −0.75 D is added to the S value of the weaker eye (Step D-5). Next, the difference in the C value between the left and right eyes after the correction processing C1 is compared with the reference value (Step D-6), and if the difference exceeds 0.75 D, the C value of the stronger eye is set to a value in which −0.75 D is added to the C value of the weaker eye (Step D-7).

[D-2] In a case where the subject does not wear the spectacles for the first time, first, a determination is made as to the presence or absence of astigmatism in the former spectacle values (Step D-8). If astigmatism (cylinder) is present, the correction processing D1 is effected (Step D-9). Then, the correction processing B1 is carried out (Step D-10). Subsequently, the difference between the obtained S values of the left and right eyes is compared with the reference value (Step D-11), and if the difference exceeds 0.75 D, the S value of the stronger eye is set to whichever value having a greater absolute value between a value in which −0.75 D is added to the S value of the weaker eye and a value in which −0.75 D is added to the S value of the same side of the former spectacles, such that the value does not exceed the relevant one of the values of binocular perfect correction (Step D-12). Next, the difference in the C value between the left and right eyes after the correction processing D1 is compared with the reference value (Step D-13), and if the difference exceeds 0.75 D (Step D-13), the C value of the stronger eye is set to whichever value having a greater absolute value between a value in which −0.75 D is added to the C value of the weaker eye and a value in which −0.75 D is added to the C value of the same side of the former spectacles, such that the value does not exceed the relevant one of the values of binocular perfect correction (Step D-14).

If astigmatism (cylinder) is not present in the determination on the presence or absence of astigmatism (cylinder) of the former spectacle values, the correction processing C1 and the correction processing B1 are carried out (Steps D-15 and D-16). Subsequently, the difference between the obtained S values of the left and right eyes is compared with the reference value (Step D-17), and if the difference exceeds 0.75 D, the S value of the stronger eye is set to whichever value having a greater absolute value between a value in which −0.75 D is added to the S value of the weaker eye and a value in which −0.75 D is added to the S value of the same side of the former spectacles, such that the value does not exceed the relevant one of the values of binocular perfect correction (Step D-18). Next, if the difference in the C value between the left and right eyes after the correction processing C1 exceeds 0.75 D, the C value of the stronger eye is set to a value in which −0.75 D is added to the C value of the weaker eye (Steps D-19 and D-20).

[Automatic Adjustment E: In the Case of Hyperopia Having Oblique Astigmatism]

The apparatus determines whether or not the subject wears the spectacles for the first time (Step E-1).

[E-1] If the subject wears the spectacles for the first time, a determination is made as to whether or not both C values of the left and right eyes are less than or equal to −0.50 D (hereafter, the C value being less than or equal to −0.50 D refers to a smaller power, i.e., −0.25 D or −0.50 D) (Step E-2). In the case of astigmatism, if the C value is small, it is in many cases more desirable not to effect the correction of astigmatism (cylinder) for the subject. Therefore, if both C values of the left and right eyes are less than or equal to −0.50 D, it is assumed that astigmatism (cylinder) is negligible, so that the C values=0, and the S values for left and right are each set to a value in which half of the C value is added to the S value to obtain a spherical equivalent value (Step E-3). Subsequently, the difference between the obtained S values of the left and right eyes is compared with the reference value (Step E-4), and if the difference exceeds 0.75 D, the S value of the stronger eye is set to a value in which +0.75 D is added to the S value of the weaker eye (Step E-5).

In the determination (Step E-2) as to whether or not the C values are less than or equal to −0.50 D, if at least one of the left and right C values exceeds −0.50 D, the correction processing C1 is carried out (Step E-6), and the S values for left and right are each set to a value in which half of the correction amount ΔC1 is added to the value of binocular perfect correction to obtain a spherical equivalent value (Step E-7). Subsequently, if the difference between the obtained S values of the left and right eyes exceeds 0.75 D, the S value of the stronger eye is set to a value in which +0.75 D is added to the S value of the weaker eye (Steps E-8 and E-9). Next, if the difference in the C value between the left and right eyes after the correction processing C1 exceeds 0.75 D, the C value of the stronger eye is set to a value in which −0.75 D is added to the C value of the weaker eye (Steps E-10 and E-11).

[E-2] If the subject does not wear the spectacles for the first time, a determination is made as to whether or not both C values of the left and right eyes are less than or equal to −0.50 D (Step E-12). Then, a determination is made as to whether or not the respective former spectacles have astigmatism (cylinder), respectively (Steps E-13 and E-14).

If both C values of binocular perfect correction are within −0.50 D, and the former spectacles do not have astigmatism (cylinder), a setting is provided such that the C values=0, and the S values for left and right are each set to a value in which half of the C value is added to the S value to obtain a spherical equivalent value (Step E-15). Subsequently, the difference between the obtained S values of the left and right eyes is compared with the reference value (Step E-16), and if the difference exceeds 0.75 D, the S value of the stronger eye is set to whichever value having a greater absolute value between a value in which +0.75 D is added to the S value of the weaker eye made spherically equivalent and a value in which +0.75 D is added to the S value of the same side of the former spectacles, such that the value does not exceed the relevant one of the values of binocular perfect correction (Step E-17).

If the former spectacles have astigmatism (cylinder) in spite of the C values of binocular perfect correction, processing similar to that in Steps C-9 to C-14 is carried out (Step E-18 to E-23).

If at least one of the left and right C values exceeds −0.50 D, and the former spectacles do not have astigmatism (cylinder), the correction processing C1 is carried out (Step E-24), and the S values of both eyes are each set to a value in which half of the correction amount ΔC1 is added to the value of binocular perfect correction to obtain a spherical equivalent value (Step E-25). Subsequently, the difference between the obtained S values of the left and right eyes is compared with the reference value (Step E-26), and if the difference exceeds 0.75 D, processing similar to that in Step C-12 is carried out (Step E-27). Next, the difference in the C value between the left and right eyes after the correction processing C1 is compared with the reference value (Step E-28), and if the difference exceeds 0.75 D, the C value of the stronger eye is set to a value in which −0.75 D is added to the C value of the weaker eye (Step E-29).

[Automatic Adjustment F: In the Case of Myopia Having Oblique Astigmatism (Cylinder)]

The apparatus determines whether or not the subject wears the spectacles for the first time (Step F-1).

[F-1] If the subject wears the spectacles for the first time, a determination is made as to whether or not both C values of the left and right eyes are less than or equal to −0.50 D (Step F-2). If both C values are within −0.50 D, both C values are set such that C values=0 (Step F-3). Then, the correction processing A1 is carried out for the S values (Step F-4). Subsequently, the difference between the obtained S values of the left and right eyes is compared with the reference value (Step F-5), and if the difference between the left and right eyes exceeds 0.75 D, the S value of the stronger eye is set to a value in which −0.75 D is added to the S value of the weaker eye (Step F-6).

In the determination (Step F-2) as to whether or not the C values are less than or equal to −0.50 D, if at least one of the left and right C values exceeds −0.50 D, the correction processing C1 is carried out (Step F-7). Then, the correction processing A1 is carried out for the S values (Step F-8). Subsequently, the difference between the obtained S values of the left and right eyes is compared with the reference value (Step F-9), and if the difference between the left and right eyes exceeds 0.75 D, the S value of the stronger eye is set to a value in which −0.75 D is added to the S value of the weaker eye (Step F-10). Next, the difference in the C value between the left and right eyes after the correction processing C1 is compared with the reference value (Step F-11), and if the difference exceeds 0.75 D, the C value of the stronger eye is set to a value in which −0.75 D is added to the C value of the weaker eye (Steps F-12).

[F-2] If the subject does not wear the spectacles for the first time, a determination is made as to whether or not both C values of the left and right eyes are less than or equal to −0.50 D (Step F-13). Then, a determination is made as to whether or not the respective former spectacles have astigmatism (cylinder) (C value), respectively (Steps F-14 and F-15).

If both C values of binocular perfect correction are within −0.50 D, and the former spectacles do not have astigmatism (cylinder), a setting is provided such that the C values=0 (F-16). Subsequently, the correction processing B1 is carried out (Step F-17). Then, the difference between the obtained S values of the left and right eyes is compared with the reference value (Step F-18), and if the difference between the left and right eyes exceeds 0.75 D, processing similar to that in Step B7 is carried out for the S value of the stronger eye (Step F-19).

If the former spectacles have astigmatism (cylinder) in spite of the C values of binocular perfect correction, processing similar to that in Steps D-9 to D-14 is carried out (Step F-20 to F-25).

If at least one of the left and right C values exceeds –0.50 D, and the former spectacles do not have astigmatism (cylinder), the correction processing C1 is carried out for the C values (Step F-26), and the correction processing B1 is carried out for the S values (Step F-27). Subsequently, the difference between the obtained S values of the left and right eyes is compared with the reference value (Step F-28), and if the difference between the left and right eyes exceeds 0.75 D, processing similar to that in Step B-7 is carried out for the S value of the stronger eye (Step F-29). Next, the difference in the C value between the left and right eyes after the correction processing C1 is compared with the reference value (Step F-30), and if the difference between the left and right eyes exceeds 0.75 D, the C value of the stronger eye is set to a value in which –0.75 D is added to the C value of the weaker eye (Step F-31).

In the above-described manner, when it is possible to distinguish between hyperopia and myopia, the apparatus effects the processing of one of automatic adjustment A to F, and automatically calculates rough powers serving as prescription values.

It should be noted that although, in the above-described automatic adjustment program, as for the adjustment amount for adjusting the S value or the C value of the stronger eye, in a case where a change from the former spectacle of the same side is adopted, adjustment of ±0.75 D (three steps) is made with respect to the S value or the C value (Steps A-5, B-7, C-14, etc.), an arrangement may be provided such that an adjustment amount of ±0.50 D (two steps) is varied depending on the age of the subject. The reason for this is that there are differences in the adaptive capability with respect to the change in the powers of the former spectacles depending on the age. A young person is capable of adapting himself or herself even if there is a change of three steps (0.75 D) with respect to the powers of former spectacles, but as the age becomes higher, a change of two steps (0.50 D) generally becomes a limit in adaptation. Accordingly, if an attempt is made to change the adjustment amount of the prescription powers depending on the adaptive capability of the eye being examined, it is possible to provide a prescription which is more suitable for the wearer. In the case where the adjustment amount of the power is changed depending on the age, the following procedure is taken. In the automatic adjustment program, for example, two kinds of power adjustment amounts are prepared, including three steps (0.75 D) and two steps (0.50 D) depending on whether the age is greater than or equal to a certain age (38 years of age) (or more kinds may be provided). When the optometric program is in progress, if the advance switch 36 is pressed after completion of testing for confirming the stereoscopic vision, an operational instruction for entering "less than 38 years of age" or "38 years of age or more" as the age of the subject is displayed in a lower portion of the screen. If the examiner presses a function switch corresponding to either one of the operational instructions, the apparatus calculates rough powers by using the aforementioned preset adjustment amount in correspondence with an input signal.

In addition, although the arrangement adopted in the embodiment is such that the automatic adjustment program is executed upon obtaining an input signal by the advance switch 36, this automatic adjustment program can be executed in the manual optometry as well if necessary data has been inputted thereto. In the manual optometry, if the "prescription" switch in the group of input-data designating switches 38 is pressed while the shift switch 44 is pressed, the automatic adjustment program is executed. In this case as well, the power adjustment amount may be changed depending on the age of the subject.

Furthermore, although, in the above-described embodiment, the correction amounts ΔS1, ΔS2, ΔC1, and ΔC2 in the correction processing A1 to D1 are obtained by calculation, tables may be prepared in advance respectively, and the correction amounts ΔS1, ΔS2, ΔC1, and ΔC2 in the correction processing A1 to D1 may be obtained on the basis of the tables.

<Adjustment of Correction Power for Far Use—(2) Adjustment by Examiner>

Figures 17, 21, 22:
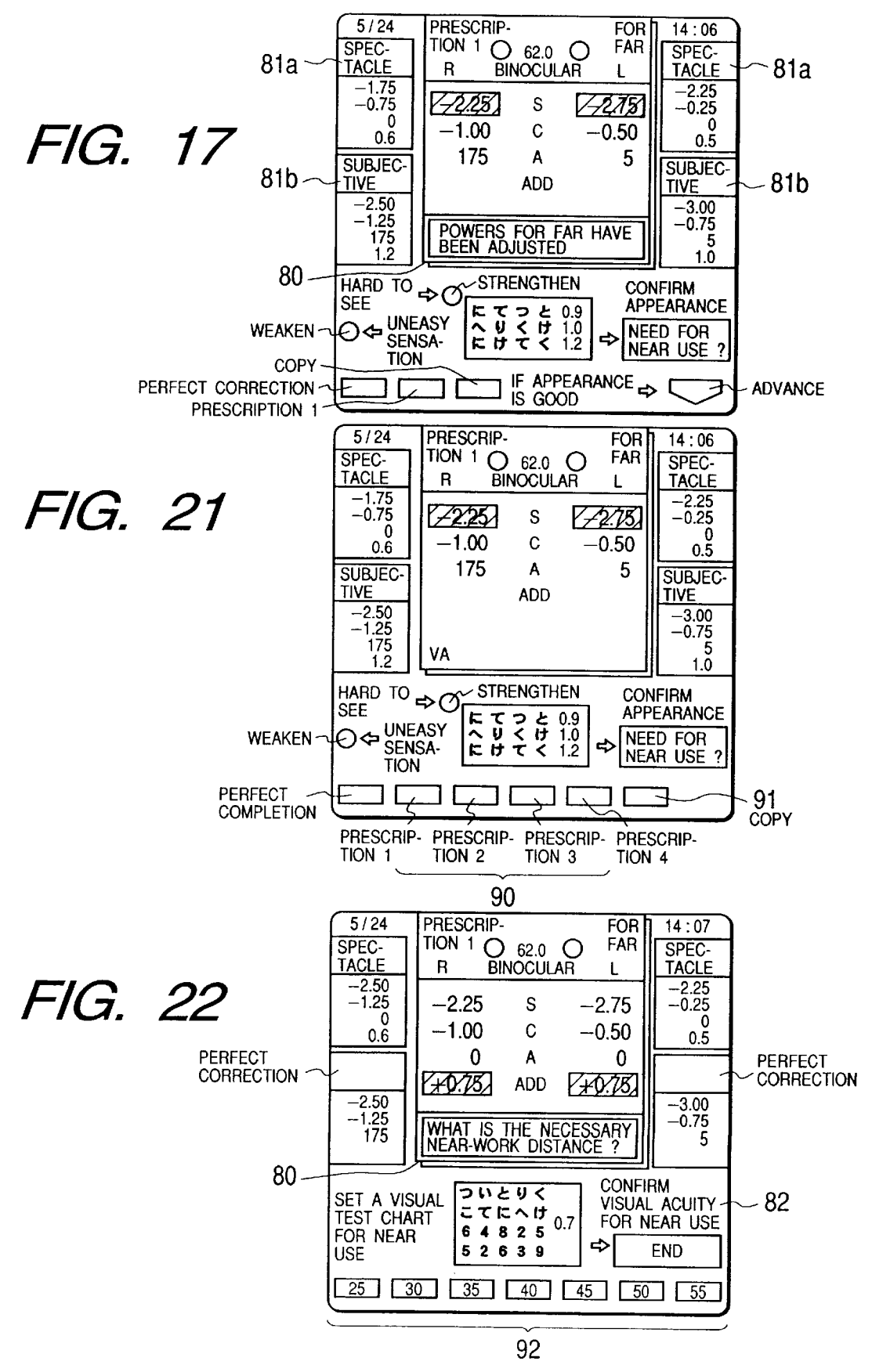

If rough powers of prescription values are prepared by the automatic adjustment program, the results are displayed on the display 30. FIG. 17 is a diagram illustrating an example of the screen of the display 30 after the automatic adjustment. The central display portion 80 is changed to a prescription mode, the rough powers which have been automatically adjusted by the apparatus as the S values and the C values in the display, and a message to the effect that the powers for far use have been corrected is displayed in the lower portion of the central display 80. Optical systems corresponding to the automatically adjusted powers are set in the test windows of the subjective-type refractive-power measuring device 2, and test targets (charts) provided in a set of targets (charts) with visual acuity values ranging from 0.9 to 1.2 are presented from the target (chart) presenting device. While confirming the appearance of the adjusted power, the examiner makes fine adjustment of the correction power for far use by means of the switch operation.

The apparatus has a control program for manual adjustment whereby the power of the item to be adjusted is changed if a switch input is made on the basis of the hyperopia or myopia, the presence or absence of astigmatism (cylinder), and the presence or absence of oblique astigmatism (cylinder) which are provided by the rough powers of the prescription values calculated by the automatic adjustment program. When the automatic adjustment program has been executed, if the changeover switch 43a or 43b is operated after obtaining a response from the subject on the appearance, the power of the item to be adjusted changes.

Figure 18:
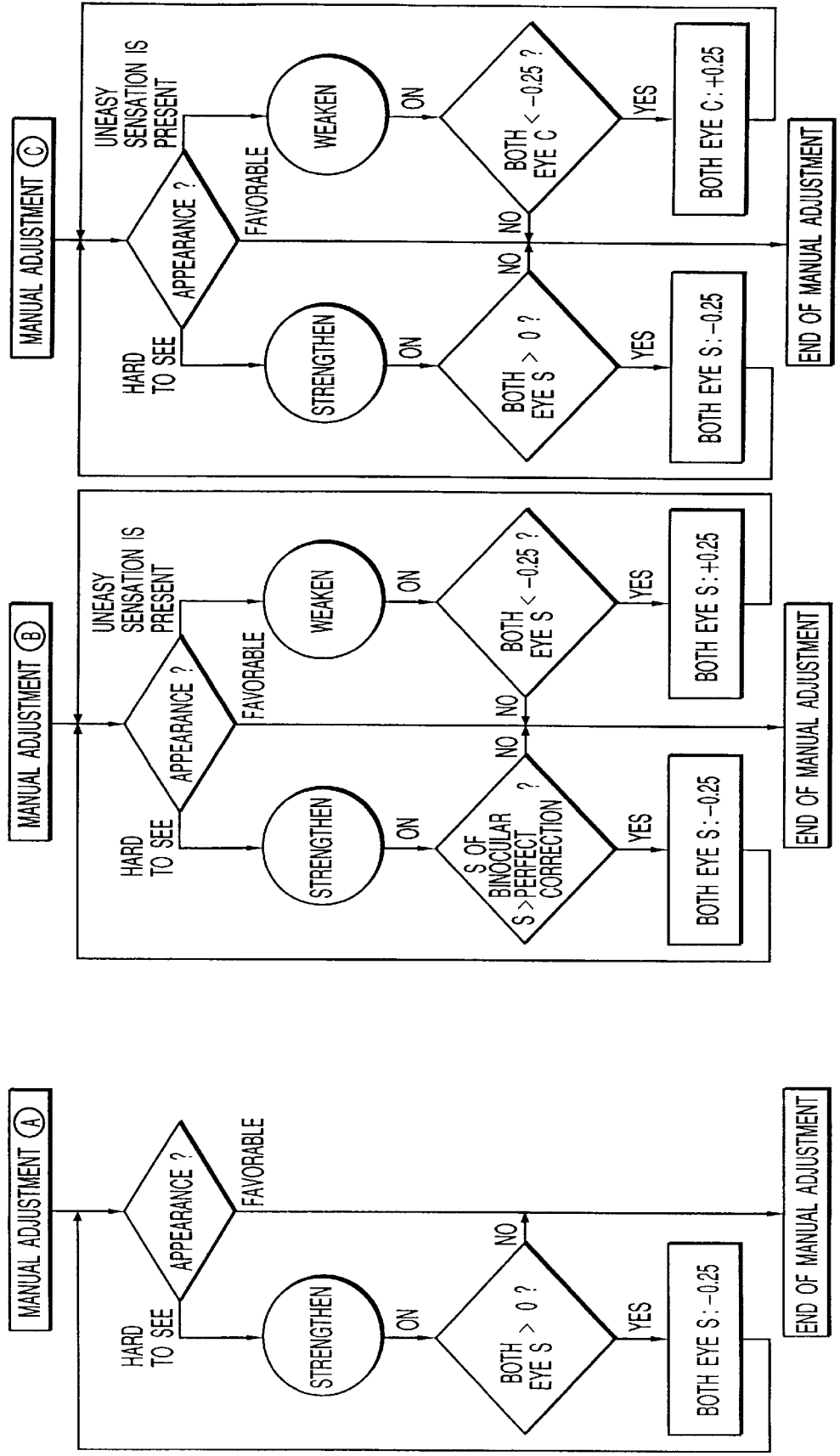
FIG. 18 is a flowchart illustrating an adjustment program for manual adjustment.
Figure 19:
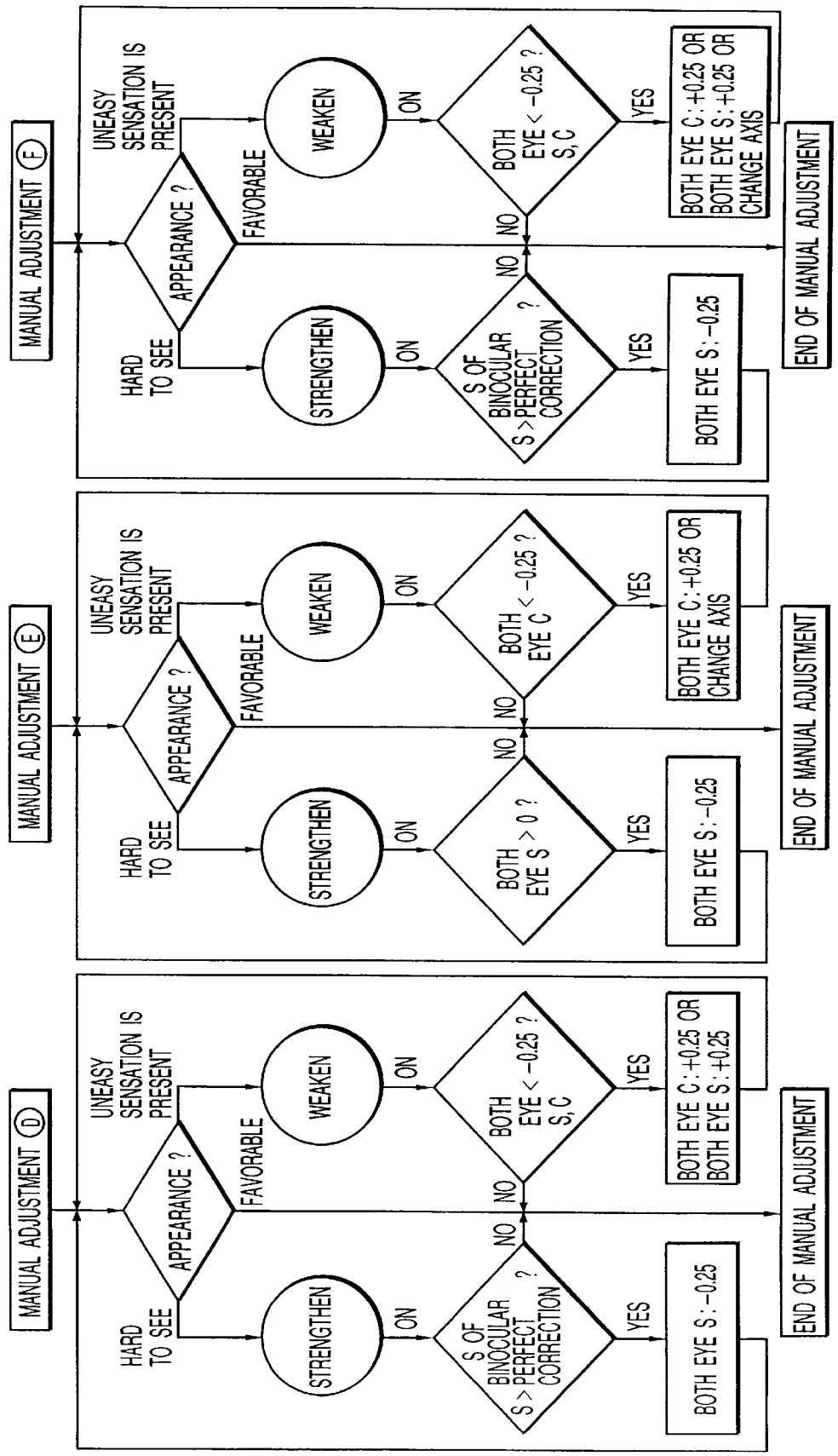
FIG. 19 is a flowchart illustrating the adjustment program for manual adjustment.

Hereafter, a description will be given of the manual adjustment based on the control program of the apparatus (see FIGS. 18 and 19).

[Manual Adjustment A: In the Case of Adjustment of Powers of Hyperopia Without Astigmatism (Cylinder)]

The subject is allowed to visually confirm the presented targets (charts) through the optical systems set in the test windows of the subjective-type refractive-power measuring device 2, and an appearance at the automatically adjusted powers is confirmed. If the subject is satisfied with the appearance, the adjustment ends. If the target (chart) is difficult to view, the "STRENGTHEN" switch 43b is pressed. As a result of this input signal, a determination is made as to whether or not the S value of the adjusted power of each eye is greater than 0, and if it is determined that it is greater than 0, –0.25 D is added to the S value of each eye. This operation is repeated until the subject is satisfied with the appearance, or the S value of each eye becomes 0. After the S value of one eye has become 0, adjustment is made until the S value of the other eye becomes 0. In the correction of hyperopia, adjustment to the myopic side in which case the S value becomes minus is undesirable, so that when the S value has become 0, a warning is issued by the buzzer 54, informing the examiner that the input is impossible. Incidentally, in this flow, the input by the "WEAKEN" switch 43a is not accepted, and when this switch is pressed, a buzzer sound is issued in a similar manner.

[Manual Adjustment B: In the Case of Adjustment of Powers of Myopia Without Astigmatism (Cylinder)]

The examiner confirms the appearance at the automatically adjusted powers. If the target (chart) is difficult to view, the "STRENGTHEN" switch 43b is pressed. As a result of this input signal, a determination is made as to whether or not the S value of the adjusted power is greater (smaller in the absolute value) than the S value of binocular perfect correction, and if it is greater, –0.25 D is added to the S value of each eye. The input by the "STRENGTHEN" switch 43b is accepted until both the adjusted S values of both eyes reach the limits of the values of binocular perfect correction. When the limits are reached, a buzzer sound is issued (in the following description as well, a buzzer sound is issued when a limit is reached).

When an uneasy sensation (the power is strong) is present in the confirmation of the appearance, the "WEAKEN" switch 43a is pressed. A determination is made as to whether or not the S value of each eye is lower than –0.25 D (whether it is 0), and if the S value is not lower than –0.25 D (it is not 0), +0.25 D is added to the S value of each eye. After the S value of one eye has become –0.25 D, adjustment is made until the S value of the other eye becomes –0.25 D.

[Manual Adjustment C: In the Case of Adjustment of Powers of Hyperopia and Astigmatism (Cylinder) Which is Not Oblique Astigmatism (Cylinder)]

The examiner confirms the appearance at the automatically adjusted powers. If the target (chart) is difficult to view, the power adjustment is made in the same way as with the manual adjustment A by pressing the "STRENGTHEN" switch 43b.

If the subject has expressed an uneasy sensation, the "WEAKEN" switch 43a is pressed. A determination is made as to whether or not the C value of each eye is lower than –0.25 D (whether it is 0), and if the C value is not lower than –0.25 D (it is not 0), +0.25 D is added to the C value of each eye. If the C value is lower than –0.25 D, a buzzer sound is issued.

[Manual Adjustment D: In the Case of Adjustment of Powers of Myopia and Astigmatism (Cylinder) Which is Not Oblique Astigmatism (Cylinder)]

The examiner confirms the appearance at the automatically adjusted powers. If the target (chart) is difficult to view, the power adjustment is made in the same way as with the manual adjustment B by pressing the "STRENGTHEN" switch 43b.

If the subject has expressed an uneasy sensation, the "WEAKEN" switch 43a is pressed. A determination is made as to whether or not both the S value and the C value of each eye are lower than –0.25 D (whether they are 0), and if both the S value and the C value of each eye are not lower than –0.25 D (they are not 0), the power of the C value or the S value is adjusted consecutively by the number of inputs by the switch 43a through a combination of the S value and the C value as described below. Through a first input signal, +0.25 D is added to the C value of each eye. Through a second input signal, the +0.25 D added to the C value in the first input is returned, and +0.25 D is added to the S value. Through a third input signal, +0.25 D is added to the C value with respect to the power of the second adjustment. Thereafter, by the number of inputs by the switch 43a, the operation is repeated until both the S value and the C value reach their limits (when either one of the S value and the C value reaches a limit first, the power of the other value is dropped).

[Manual Adjustment E: In the Case of Adjustment of Powers of Oblique Astigmatism (Cylinder) and Hyperopia]

The examiner confirms the appearance at the automatically adjusted powers. If the target (chart) is difficult to view, the power adjustment is made in the same way as with the manual adjustment A by pressing the "STRENGTHEN" switch 43b.

If the subject has expressed an uneasy sensation, the "WEAKEN" switch 43a is pressed. A determination is made as to whether or not the C value of each eye is lower than –0.25 D (whether it is 0), and if the C value is not lower than –0.25 D (it is not 0), the C value or the A value of each eye is adjusted by the number of inputs by the switch 43a on the basis of a combination of the C Values and the A values.

A description will be given of the power adjustment in the combination of the C values and the A values in oblique astigmatism (cylinder). When an uneasy sensation in spatial vision in oblique astigmatism (cylinder) is alleviated, adjustment is made for causing the axis to approach a horizontal direction or vertical direction. At this time, if the axis determined in perfect correction is rotated, new astigmatism (cylinder) is produced. If it is assumed that the C value of perfect correction is $C_1$, and the A value is $\theta_1$, and that the C value for prescription is $C_2$, and the A value is $\theta_2$, the newly produced astigmatic (cylindrical) power $C_0$ and its axial angle $\theta_0$ can be expressed as follows:

(a) $\tan 2\theta_0 = (C_1 \sin 2\theta_1 - C_2 \sin 2\theta_2)/(C_1 \cos 2\theta_1 - C_2 \cos 2\theta_2)$ (b) $C_0 = (C_1 \sin 2\theta_1 - C_2 \sin 2\theta_2)/\sin 2\theta_0$ When an uneasy sensation is present, the astigmatic (cylindrical) power is decreased by inputs by the "WEAKEN" switch 43a, which results in an increase in newly produced astigmatism (cylinder), i.e., residual astigmatism (cylinder). Since the step of change in the astigmatic (cylindrical) power in the embodiment is set at 0.25 D, the power is adjusted in such a manner that the power changes by portions of approximately 0.12 D in terms of the C-value equivalent by the number of inputs by the switch 43a on the basis of the above-described formulae, so that the residual astigmatic (cylindrical) power due to the rotation of the axis is brought to an intermediate level (about 0.12 D) of the step of change 0.25 D. In the first input by the switch 43a, the axial angle for each eye is first adjusted so that the power changes by an approximately 0.12 D portion in terms of the C-value equivalent. In the second input, the axial angle is returned to cause a change by another approximately 0.12 D portion, and the C value of each eye is dropped by the 0.25 D portion. In the third input, the axial angle is adjusted to cause a change by the approximately 0.12 D portion with respect to the second input. Thus, astigmatism (cylinder) is adjusted on the basis of the relationship between the number of inputs by the switch 43a and the combination of the C value and the A value (refer to a specific example shown in FIG. 20). After the C value of one eye has become –0.25 D, adjustment can be made until the C value of the other eye becomes –0.25 D.

It should be noted that the adjustment of astigmatism (cylinder) can be made not on the basis of the above-described calculation but on the basis of a table prepared in advance.

[Manual Adjustment F: In the Case of Adjustment of Powers of Oblique Astigmatism (Cylinder) and Myopia]

The examiner confirms the appearance at the automatically adjusted powers. If the target (chart) is difficult to view, the power adjustment is made in the same way as with the manual adjustment B by pressing the "STRENGTHEN" switch 43b.

If the subject has expressed an uneasy sensation, the "WEAKEN" switch 43a is pressed. A determination is made as to whether or not both the S value and the C value of each eye are lower than −0.25 D (whether they are 0), and if both the S value and the C value of each eye are not lower than −0.25 D (they are not 0), S, C, and A of each eye are adjusted by the number of inputs by the switch 43a through a combination of S, C, and A. This adjustment is also made by processing which is similar to that in the case of the above-described manual adjustment E. In the first input, the axial angle is first adjusted so that the power is decreased by an approximately 0.12 D portion in terms of the C-value equivalent. In the second input, the axial angle is returned, and the C value is decreased by an approximately 0.25 D portion. In the third input, the portion of change in the C value in the previous input is returned, and the S value is decreased by a 0.25 D portion. In the fourth input, the S value in the previous input is kept as it is, and the power is decreased by an approximately 0.12 D portion in terms of the C value equivalent by adjustment of the axial angle. Thereafter, this procedure is repeated in order. After the C value of one eye has become −0.25 D, adjustment can be made until the C value of the other eye becomes −0.25 D. After the S value of one eye has become −0.25 D, adjustment can be made until the S value of the other eye becomes −0.25 D.

Through the above-described manual adjustments A to F, the state of the subject's vision is confirmed, a response for it is obtained, and inputs are made by either the switch 43a or the switch 43b, whereby the powers of appropriate items can be automatically adjusted. For this reason, even an inexperienced examiner is able to easily adjust the powers for far use without being confused about the items to be adjusted, their directions, and switch operations.

It should be noted that, in the prescription mode in manual adjustment, each time the switch 43a or 43b is pressed, the immediately preceding prescription power data are consecutively stored in the memory of the apparatus, and, as shown in FIG. 21, a display 90 is given in a lower portion of the operation explanation area 82 to the effect that adjusted powers, which have been consecutively stored, such as prescription values 2, prescription values 3, . . . , are provided for prescription values 1 of the automatically adjusted powers calculated by the apparatus. If a relevant function switch 45 corresponding to each prescription value in the display 90 is pressed, the optical system disposed in the test window of the subjective-type refractive-power measuring device 2 and the display in the central display portion 80 are instantly changed over, and a comparison of the adjusted powers can be made instantly. It goes without saying that the item to be adjusted and its powers can be manually changed by designating the mode by the switch S, C, or A of the group of mode-change designating switches 37, and by rotating the dial switch 42 clockwise or counterclockwise. If a relevant function switch 45 corresponding to a "COPY" display 91 which is a display of an operational instruction is pressed, that data can be copied, changed manually, and stored in the memory.

In addition, if the mode is set in the prescription mode, a plurality of items of reference data, which are the results in the previous test modes, are displayed on the left- and right-hand sides of the central display portion 80. The example of the screen shown in FIG. 17 shows first left and right displays 81a for displaying spectacle values, which are the results of the test mode before last, and their confirmed visual acuity values, as well as second left and right displays 81b for displaying subjective values of monocular perfect correction, which are the results of the test mode before last, and their confirmed visual acuity values (when the former spectacle data is not available, unaided visual acuity values are displayed). As a result, the examiner is able to readily confirm the data obtained in advance with respect to the present measurement mode. In particular, this arrangement is convenient since, in the stage for adjusting the prescription powers, adjustment can be made while making a comparison by simultaneously viewing the spectacle values and the subjective values of monocular perfect correction or the like. Further, since the visual acuity values of the former spectacles and visual acuity values in the subjective test of monocular perfect correction are displayed, it is possible to ascertain to what power the visual acuity of the subject can be ensured in the adjustment of the prescription powers and to what power an increase in visual acuity can be expected, so that this is useful in the adjustment for prescription.

It should be noted that although in the example of the screen shown in FIG. 17 two kinds of data on the first and second left and right displays are used in the display of the reference data, three or more kinds of data may be displayed. How many kinds of data are to be displayed is designated in advance in the setting of parameters in the menu screen prior to the examination.

In addition, although an optometric program is used in the embodiment, it is, of course, possible to display a plurality of items of reference data in the manual examination as well. At what stage the reference data is to be displayed may be set in advance, or the reference data may be displayed when a plurality of items of test data have been inputted.

When the display of the reference data is changed to other data, the following procedure is taken. For example, when it is desirable to view objective value data in the example of the screen shown in FIG. 17, the objective switch of the group of input-data designating switches 38 is pressed while the shift switch 44 is pressed. The subjective value data of monocular perfect correction shifts to the first left and right displays 81a, while the objective value data invoked from the memory is displayed in the second left and right displays 81b. Thus, it is possible to freely invoke and display only the data which the examiner wishes to view, without changing the present measurement mode.

<Examination for Near Use>

After adjustment of the correction powers for far use has been made, the advance switch 36 is pressed to proceed to an ensuing test. Since a message is displayed on the screen of the display 30, inquiring whether an examination for near use is required, when the examination for near use is to be effected, a relevant function switch 45 is pressed in compliance with the operational instruction. Subsequently, an operational instruction for entering the age of the subject is displayed on the screen (when the age has already been entered at the time of inquiry, this step may be omitted). If a relevant function switch 45 corresponding to that operational instruction is pressed, the apparatus issues an operating signal to the subjective-type refractive-power measuring device 2. Optical systems of values of binocular perfect correction are set in the test windows of the subjective-type refractive-power measuring device 2, and addition powers estimated to be required on the basis of the inputted age (as the addition powers, the setting of halves of the estimated values or a setting which is three stages (0.75 D) weaker or the like are also possible) as well as XC lenses for near use are set therein. In addition, if a signal for conducting the examination for near use is entered, the flapping mechanism of the subjective-type refractive-power measuring device 2 is driven, so that the lens units 10 are made to converge at an angle of convergence which corresponds to a near-use distance 35 cm. The controller 5 is set in the addition mode, and the spherical powers can be added by means of the dial switch 42 and the like. The examiner presents a near-use target (chart) of a cross grid at a distance of 35 cm in front of the subject's eyes. The addition powers for both eyes are measured, and the addition powers are entered.

After the addition powers have been entered, the advance switch 36 is pressed. The apparatus, upon receipt of the input signal, shifts the screen to one for confirming whether or not the subject wears the spectacles for near use for the first time. If the subject wears them for the first time, a relevant function switch 45 is pressed and adjustment is made for adding –0.25 D as the addition power. If the subject does not wear the spectacles for near use for the first time, a relevant function switch 45 for leaving the addition powers as they are is pressed. The apparatus converts into differential addition powers the difference in the S value and the difference in the equivalent spherical C value, which were adjusted for far use, from the values of binocular perfect correction, and values in which these differential addition powers are subtracted from the measured addition powers are calculated as adjusted addition powers. However, if these values have become minus, the addition powers are set at 0. The adjusted values are displayed on the screen of the display 30, and a message to the effect that the addition powers have been adjusted is displayed thereon.

Subsequently, the examiner sets a visual test chart for near use for confirming visual acuity, and confirms that the visual acuity value is not lower than 0.7. If it is lower, visual acuity is confirmed. A check is made as to whether the visual acuity improves by adding +0.25 D to the ADD value of each eye. If the visual acuity improves, another +0.25 D is added to the ADD value of each eye. If the visual acuity remains unchanged or drops, –0.25 D is added to the ADD value of each eye to return to lower values. The addition powers are thus determined.

[Confirmation of the Appearance of Powers for Far Use in Converged State]

After determination of the addition powers, the following procedure is taken when allowing the subject to confirm to what extent it is difficult to view a target (chart) for near use if it is viewed with the adjusted powers for far use. The examiner presses the ADD switch in the group of switches 37. If this switch signal is inputted, the apparatus sets the subjective-type refractive-power measuring device 2 as it is in the converged state, and disposes in the test windows optical systems with powers for far use in which the addition powers have been canceled and which have been finally adjusted. The subject is allowed to view the target (chart) for near use in this state. Next, if the ADD switch is pressed again, the apparatus returns the canceled addition powers. The subject is allowed to view again the target (chart) for near use in the state of the prescribed addition powers. Thus, since the state of the powers for near use and the state of the powers for far use can be instantly changed over with the subjective-type refractive-power measuring device 2 set in the converged state, the subject is allowed to actually feel the difference in the appearance clearly.

[Conversion of Powers to Different Near-Work Distance]

In addition, in the examination for near use, addition powers at a predetermined distance (in this embodiment, 35 cm) are obtained, but there are cases where a necessary near-work distance is different from the distance in the examination for near use depending on subjects. In this case, it is necessary to adjust the addition powers at the near-work distance desired by the subject. If the required near-work distance is inputted, this apparatus is capable of changing the measured powers for near use to the powers for near use at the inputted distance.

A description will be given of a method of conversion of the powers for near use to a different near-work distance which is effected by the apparatus.

If it is assumed that the addition power measured at a near-use test distance f(m) is ADD(f), the accommodative power necessary for the near-use test distance f can be considered to be 1/f, so that the accommodative power which the eye being examined was able to use is 1/f–ADD (f). In contrast, if accommodative power necessary for a different near-work distance f'(m) is assumed to be 1/f', the addition power ADD(f') necessary for this distance can be set as $$ADD(f')=\{1/f'-(1/f-ADD(f))\}$$

However, in the calculation of the power, the power is rounded off to a closer measuring step (in the embodiment, 0.25 D step).

The operation of conversion to a different near-work distance is effected as follows. After completion of the examination for near use, if the advance switch 36 is pressed, an operational instruction 92 indicating a necessary near-work distance is displayed on the display screen, as shown in FIG. 22. The examiner presses a relevant function switch 45 corresponding to the necessary distance. On the basis of the above-described calculation, the apparatus calculates the addition power by converting the addition power obtained in the measurement into an addition power of the inputted distance. The converted addition powers which are calculated are displayed in ADD columns of the central display portion 80. As a result, the examiner is able to readily ascertain addition powers at the near-work distance desired by the subject.

Incidentally, a plurality of different near-work distances may be entered. Each time a relevant function switch 45 corresponding to the necessary near-work distance is pressed, the converted powers are displayed. When the conversion of powers into those for a different near-work distance, or when unnecessary, the advance switch 36 is pressed.

In addition, the converted addition power portions may be imparted to the optical systems disposed in the test windows of the subjective-type refractive-power measuring device 2, so as to confirm the appearance with addition power for a different near-work distance. Further, the subjective-type refractive-power measuring device 2 may be arranged to converge in correspondence with the near-work distance, so as to confirm the appearance by presenting a visual test chart for near use at a necessary near-work distance.

If all the tests are completed and prescription values have been determined in the above-described manner, the print switch 40 is pressed to print out the results of measurement. FIG. 23 shows an example of the print. Prescription values for far use in the S value, the C value, and the A value are printed in a print portion 101 of a FINAL column which shows prescription values. Addition powers at the near-use test distance of 35 cm are printed in a print portion 102 therebelow. In a case where a different near-work distance has been inputted, the converted addition powers, together with the inputted distance, are printed in a print portion 103 of the print portion 102. In a case where a plurality of near-work distances have been inputted, the addition powers, together with the inputted distance, are further printed therebelow.

In a FAR+ADDITION column 104, prescription values for near use in the S value, the C value, and the A value are printed after processing is effected by the apparatus for adding an addition power portion to the S value of prescription for far use. Thus, during printout, since the prescription values for near use are printed separately from the prescription values for far use, in cases where monofocal lenses for near use, for example, are prepared, the examiner is able to readily and accurately ascertain their values.

In the above-described embodiment, the display of a warning prompting the exercise of caution to the examiner with respect to the possibility of intervention by accommodation may not be based not on the objective value data, and a message prompting the exercise of caution such as "Has accommodation been sufficiently removed?" may be displayed at a stage where perfect correction values for one eye have been obtained and if the measured value in terms of the SE value is on the plus side (may be the plus side or a minus of a weak power, in the same way as described above). Further, a message prompting the exercise of caution may be displayed in cases where the effect of accommodation is unnegligible, such as when, after making a comparison with the inputted objective value data and former spectacle data, the plus power of a perfect correction value has dropped below the plus power of the inputted data (+1.50 D→+0.50 D, etc.), or when the minus data has changed to the plus side. This gives a clue to the examiner in determining whether close examination is required, before proceeding to an adjustment stage. These messages may be displayed only when, in particular, the age of a young person (e.g., 15 years of age or younger) has been inputted.

In addition, a message to the effect that caution should be exercised to the intervention by accommodation may be displayed not on the basis of the inputted power data or measured powers but at a start of examination if the age less than or equal to a certain age (which may be set freely in the setting of parameters) has been inputted. Alternatively, a message prompting the exercise of caution may be displayed after perfect correction values have been obtained.

In addition, with this apparatus, it is possible to conduct visual function tests including near and far horizontal/vertical phoria tests and convergence and divergence tests. Methods of these tests will be described with reference to the flowcharts shown in FIGS. 24 to 35.

In the apparatus of this embodiment, a plurality of optometric programs in which test items and test procedures are set in advance are stored in the memory 51, so that the examiner is able to select a mode of the optometric program conforming to the examination policy. As the modes of the optometric programs, a program A for a standard test and a program B for a simplified test have been prepared, and a program C, a program D, and a program E in which the examiner has written and inputted can be prepared. When conducting visual function tests including near and far horizontal/vertical phoria tests and convergence and divergence tests, programs for the visual function tests are inputted in advance in the program C, the program D, or the program E (the program C may be used for the standard test, and the programs D and E for simplified tests). In addition, the procedures of programs for the visual function tests are set in advance, and if one test item is finished, the examiner is able to proceed to an ensuing test item by pressing the advance switch 36. Incidentally, the procedure of this program is given as one example, and can be rearranged according to the examiner's preference.

Figure 5:
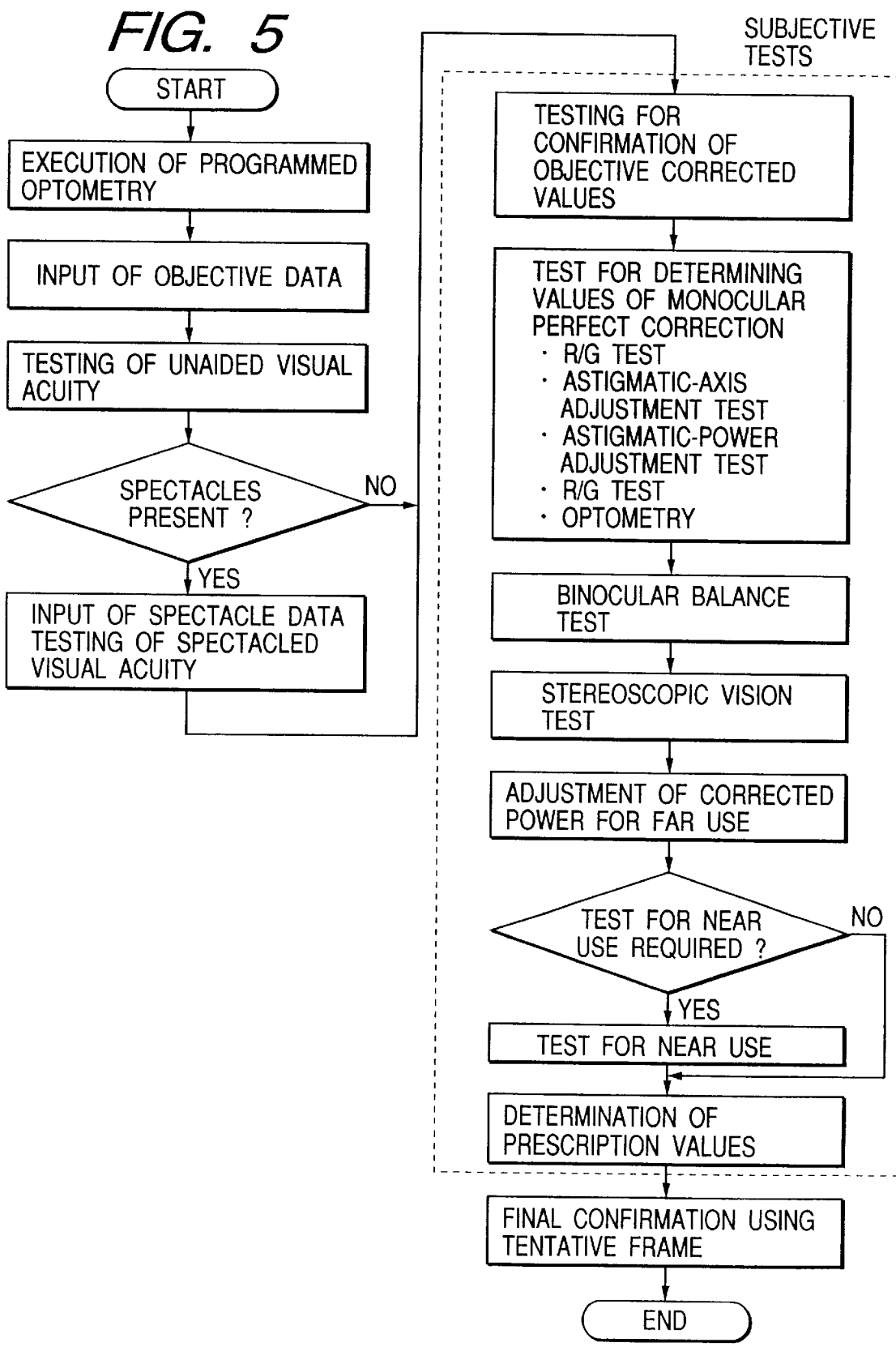
FIG. 5 is a diagram illustrating a flowchart of an optometric program in accordance with the embodiment.

With respect to a subject for whom it has been judged that a visual function test is required due to an eye complaint such as the difficulty in obtaining stereoscopic vision, or an eye complaint such as diplopia or asthenopia (visual fatigue), after the optometric program shown in FIG. 5 is finished, the optometric program modes (A, B, C, D and E) are consecutively changed over by pressing the program start key 35 while pressing the shift switch 44, so as to select and start the visual function testing program inputted in the program C, program D or the program E. Incidentally, since such visual function tests can be effected if perfect correction values are determined in the refractive power test, the visual function tests may be implemented prior to effecting the adjustment of correction powers for far use.

It should be noted that, in this examination, a pair of rotary prisms are disposed in the test windows 11 of the subjective-type refractive-power measuring device 2. As for the rotary prisms disposed on the disks, the pair of prisms having the same powers are coupled to each other by means of a gear and the like, and the pair of prisms are rotated in opposite directions by the same angles by turning the dial switch 42, so as to change the powers.

Figure 24:
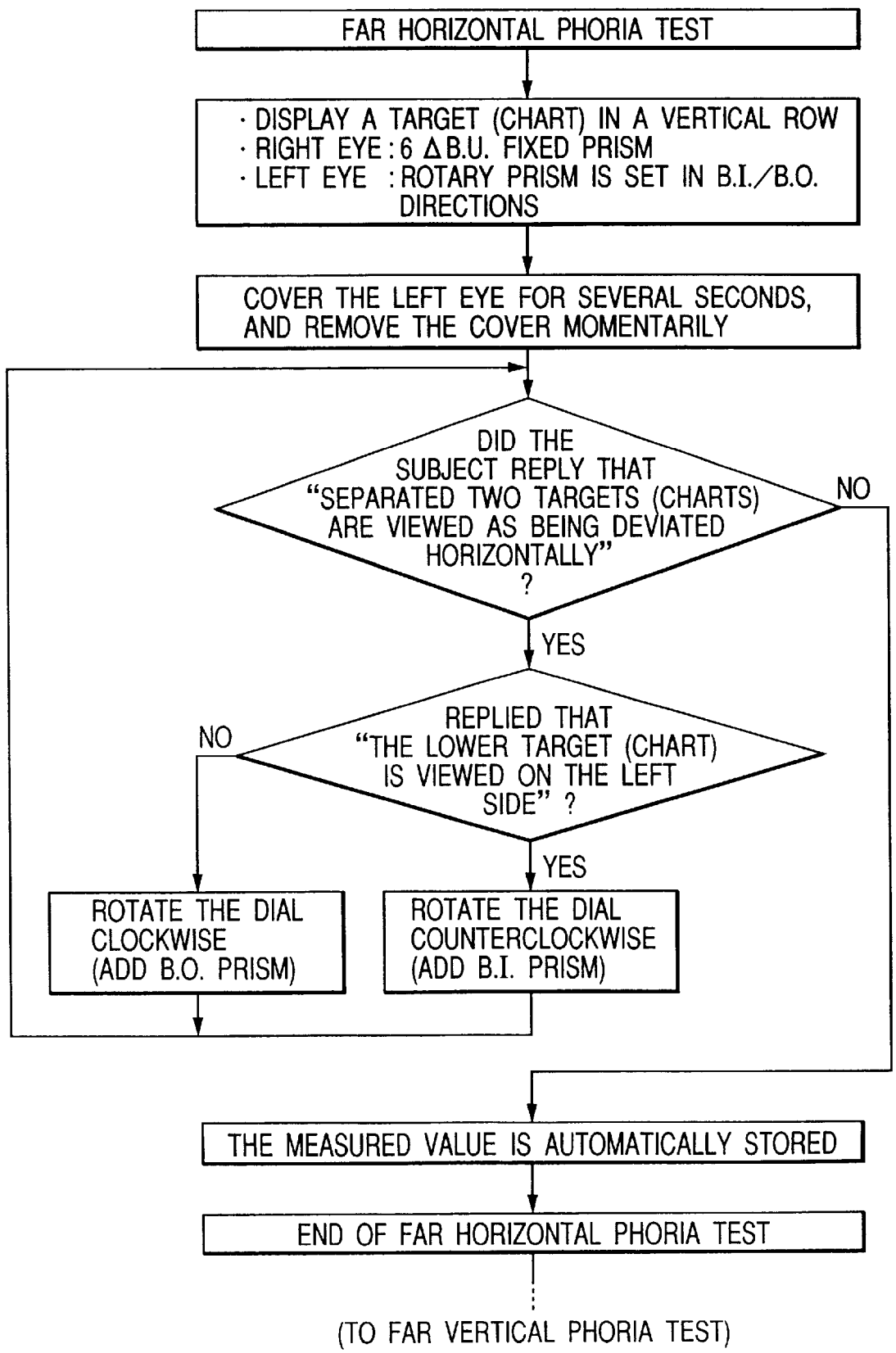
FIG. 24 is a diagram illustrating a flowchart of a visual function testing program in accordance with the embodiment.

<Far Horizontal Phoria Test—FIG. 24>

A prism separation method is adopted for the far horizontal phoria test. In the test windows of the subjective-type refractive-power measuring device 2, a 6 ΔB.U. (base up) fixed prism is placed on the right eye side, and a rotary prism is placed on the left eye side in the B.I. (base in)/B.O. (base out) directions. The smallest letters which the subject can read correctly or letters slightly larger than the same are presented as the target (chart) in a vertical row. The examiner confirms the subject that the target (chart) is divided into two upper and lower sections. Then, after the left eye of the subject is covered, and the cover is removed, the examiner confirms the subject whether the target (chart) is deviated in the horizontal direction. If deviation is not present, the examiner presses the advance switch 36 to proceed to an ensuing test item, and the determination that far horizontal phoria is not present is automatically stored (The measured value is automatically stored as 0.).

Figure 36:
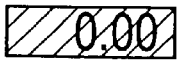
FIG. 36 is a diagram illustrating an example of the screen of the display in a far horizontal phoria test.

If the deviation is present, a check is made as to on which of the left and right sides the lower section of the target (chart) was viewed. If it was viewed on the right side, then it is the case of esophoria, so that the examiner rotates the dial switch 42 clockwise in accordance with advice 110 shown in FIG. 36 to effect correction by adding the B.O. prism, and adjustment is made until the upper and lower sections of the target (chart) are aligned (until deviation disappears). If the lower section of the target (chart) was viewed on the left side, then it is the case of exophoria, so that the examiner rotates the dial switch 42 counterclockwise to effect correction by adding the B.I. prism, and adjustment is made until the upper and lower sections of the target (chart) are aligned (until deviation disappears). After confirmation is made from the subject that there is no longer the deviation in the target (chart), the advance switch 36 is pressed to proceed to an ensuing test item. The measurement values upon completion of the adjustment are automatically stored.

Figure 25:
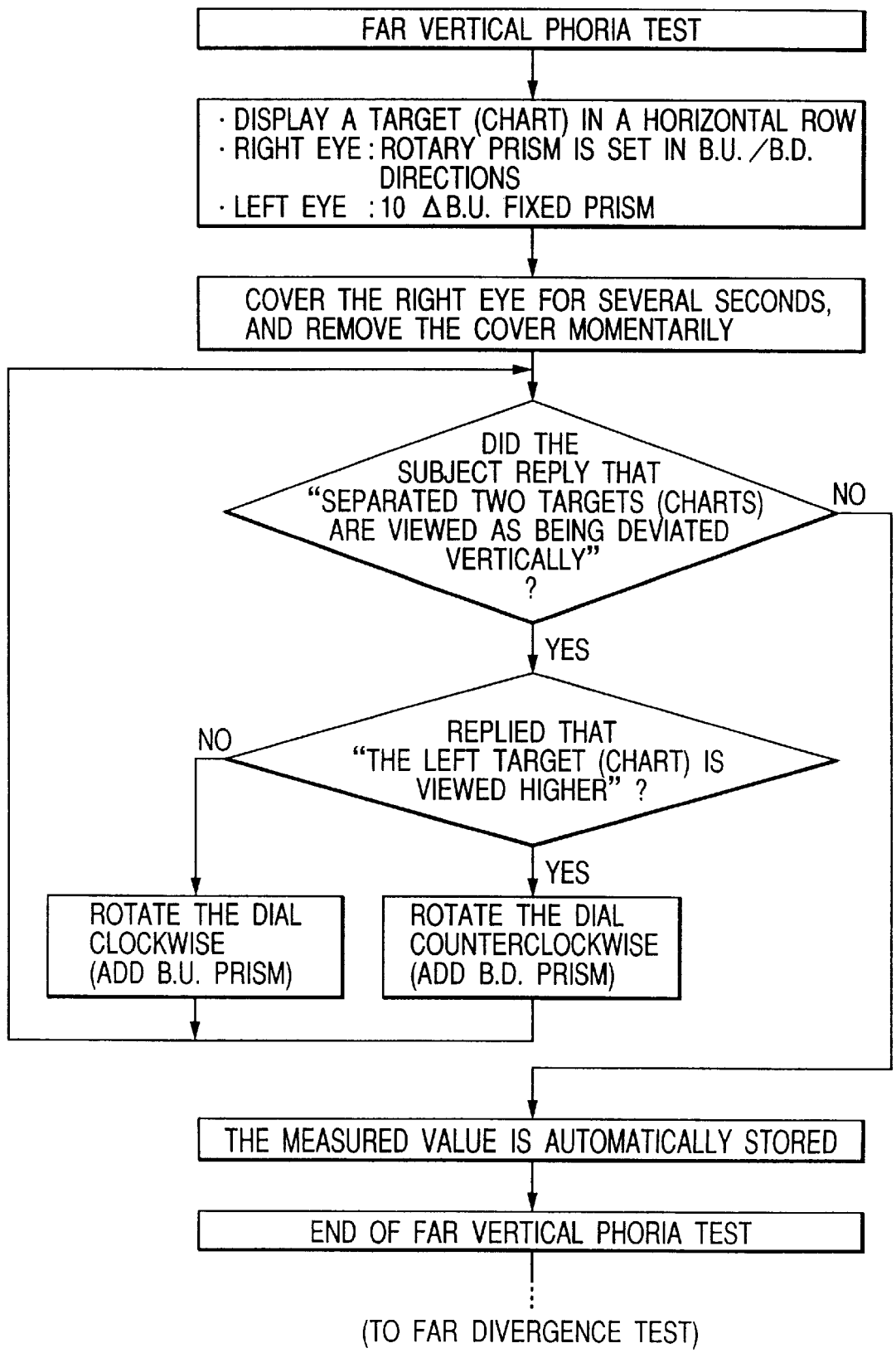
FIG. 25 is a diagram illustrating a flowchart of a visual function testing program in accordance with the embodiment.

<Far Vertical Phoria Test—FIG. 25>

The prism separation method is adopted for the far vertical phoria test as well. In the two test windows of the subjective-type refractive-power measuring device 2, a 10 ΔB.I. fixed prism is placed on the left eye side, and a rotary prism is placed on the right eye side in the B.U./B.D. (base down) directions. The smallest letters which the subject can read correctly or letters slightly larger than the same are presented as the target (chart) in a horizontal row. The examiner confirms the subject that the target (target) is divided into two left and right sections. Then, after the right eye of the subject is covered, and the cover is removed, the examiner confirms the subject whether the target (chart) is deviated in the vertical direction. If deviation is not present, the examiner presses the advance switch 36 to proceed to an ensuing test item, and the determination that far vertical phoria is not present is automatically stored (The measured value is automatically stored as 0.).

Figure 37:
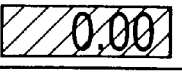
FIG. 37 is a diagram illustrating an example of the a screen of the display in a far vertical phoria test.

If the deviation is present, a check is made as to which of the left and right sections of the target (chart) was viewed on the upper side (higher). If the left side is viewed on the upper side (higher), then it is the case of right eye hyperphoria, so that the examiner rotates the dial switch 42 clockwise in accordance with advice 111 shown in FIG. 37 to effect correction by adding the B.D. prism, and adjustment is made until the left and right sections of the target (chart) are aligned (until deviation disappears). If the right section of the target (chart) was viewed on the upper side (higher), then it is the case of left eye hyperphoria, so that the examiner rotates the dial switch 42 counterclockwise to effect correction by adding the B.U. prism, and adjustment is made until the left and right sections of the target (chart) are aligned (until deviation disappears). After confirmation is made from the subject that there is no longer the deviation in the target (chart), the advance switch 36 is pressed to proceed to an ensuing test item. The measurement values upon completion of the adjustment are automatically stored.

Figure 26:
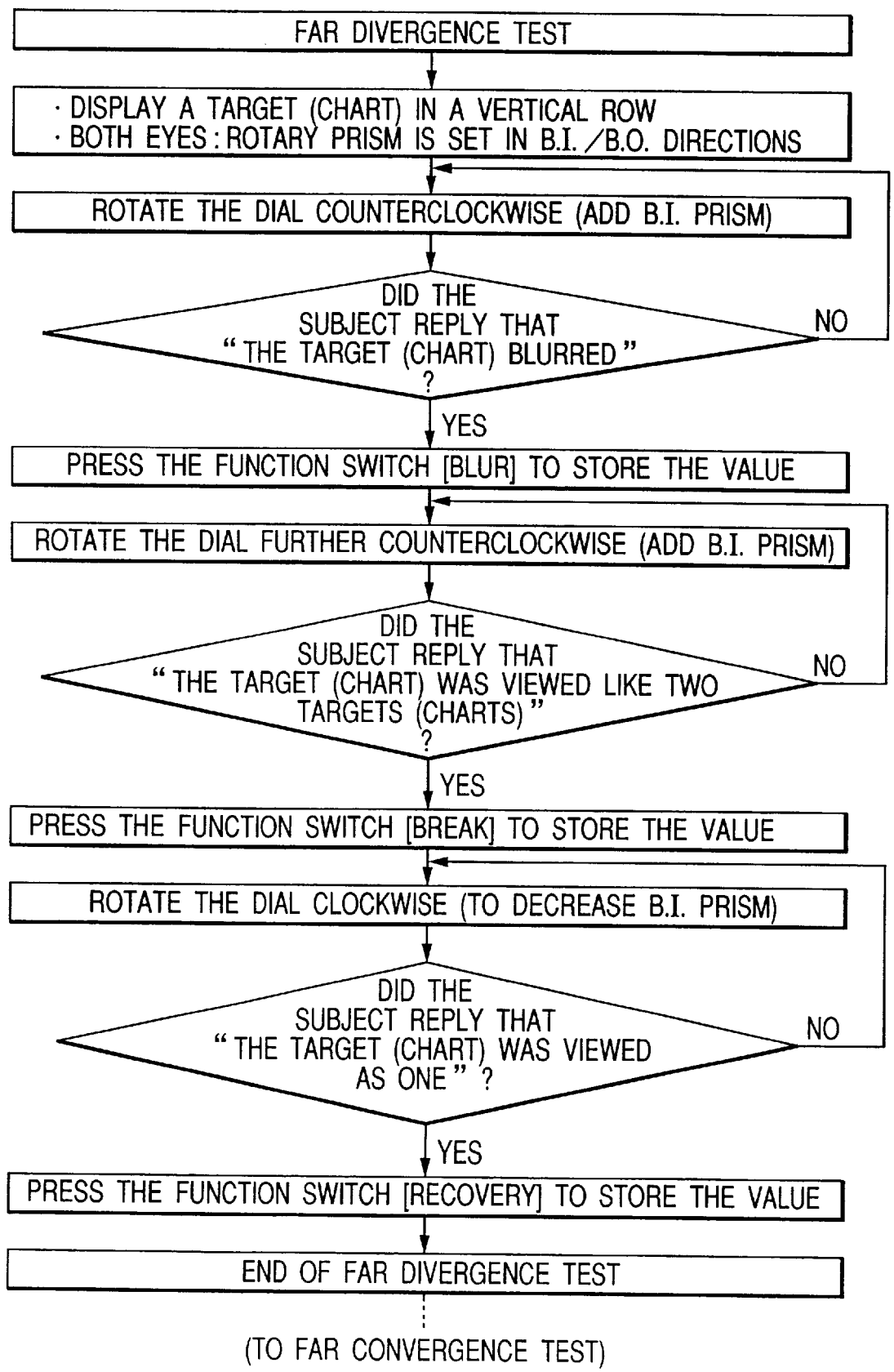
FIG. 26 is a diagram illustrating a flowchart of a visual function testing program in accordance with the embodiment.

<Far Divergence Test—FIG. 26>

Figure 38:
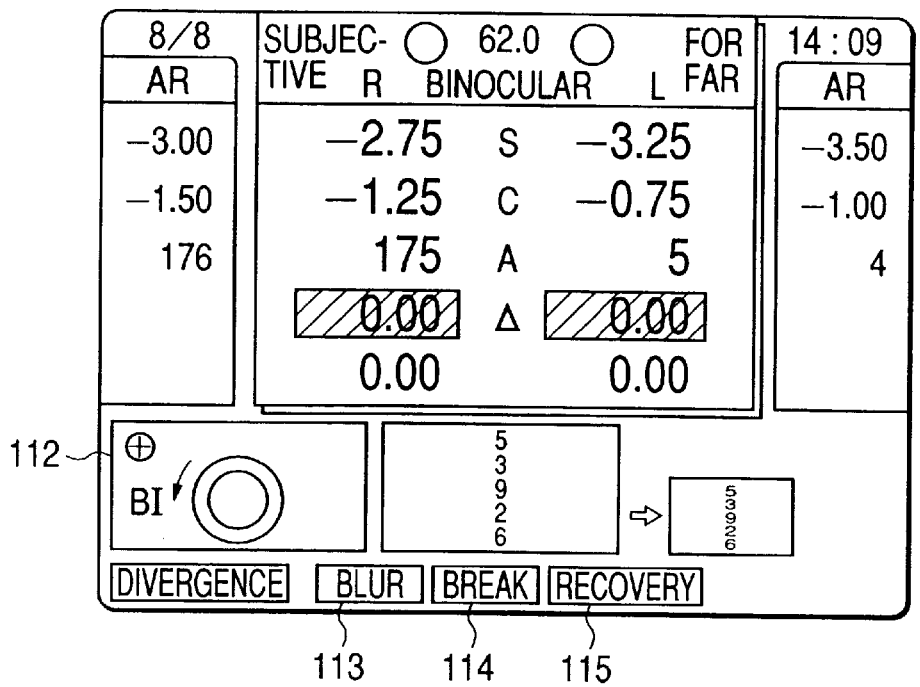
FIG. 38 is a diagram illustrating an example of the screen of the display in a far divergence test.

In the test windows of the subjective-type refractive-power measuring device 2, the pair of rotary prisms are disposed on both eye sides in the B.I./B.O. directions. The smallest letters which the subject can read correctly or letters slightly larger than the same are presented as the target (chart) in a vertical row. By rotating the dial switch 42 counterclockwise in accordance with advice 112 shown in FIG. 38 to add the B.I. prism, the examiner confirms the subject whether the target (chart) blurred. If blur is not present, the dial switch 42 is rotated further counterclockwise to add the B.I. prism. Incidentally, at this time, even if the dial switch 42 is rotated clockwise, the B.O. prism is not added. If blur is present, a "BLUR" button 113 in the group of function switches 45 is pressed, and the value of the amount of prism at the blurred point is stored.

Then, the dial switch 42 is rotated further counterclockwise to add the B.I. prism, and the subject is confirmed whether the target (chart) was viewed as if there were two targets (charts). If it was not viewed as if there were two targets (charts), the B.I. prism is further added in the same way as described above. If the target (chart) was viewed as if there were two targets (charts), a "BREAK" button 114 in the group of function switches 45 is pressed, and the value of the amount of prism at the broken (separated) point is stored.

This time, the dial switch 42 is rotated clockwise to decrease the B.I. prism, and the subject is confirmed whether the target (chart) was viewed as one (returned). If it was not viewed as one, the dial switch 42 is rotated further clockwise to decrease the B.I. prism. If the target (chart) was viewed as one, a "RECOVERY" button 115 in the group of function switches 45 is pressed, and the value of the amount of prism at the recovered point is stored.

Figure 27:
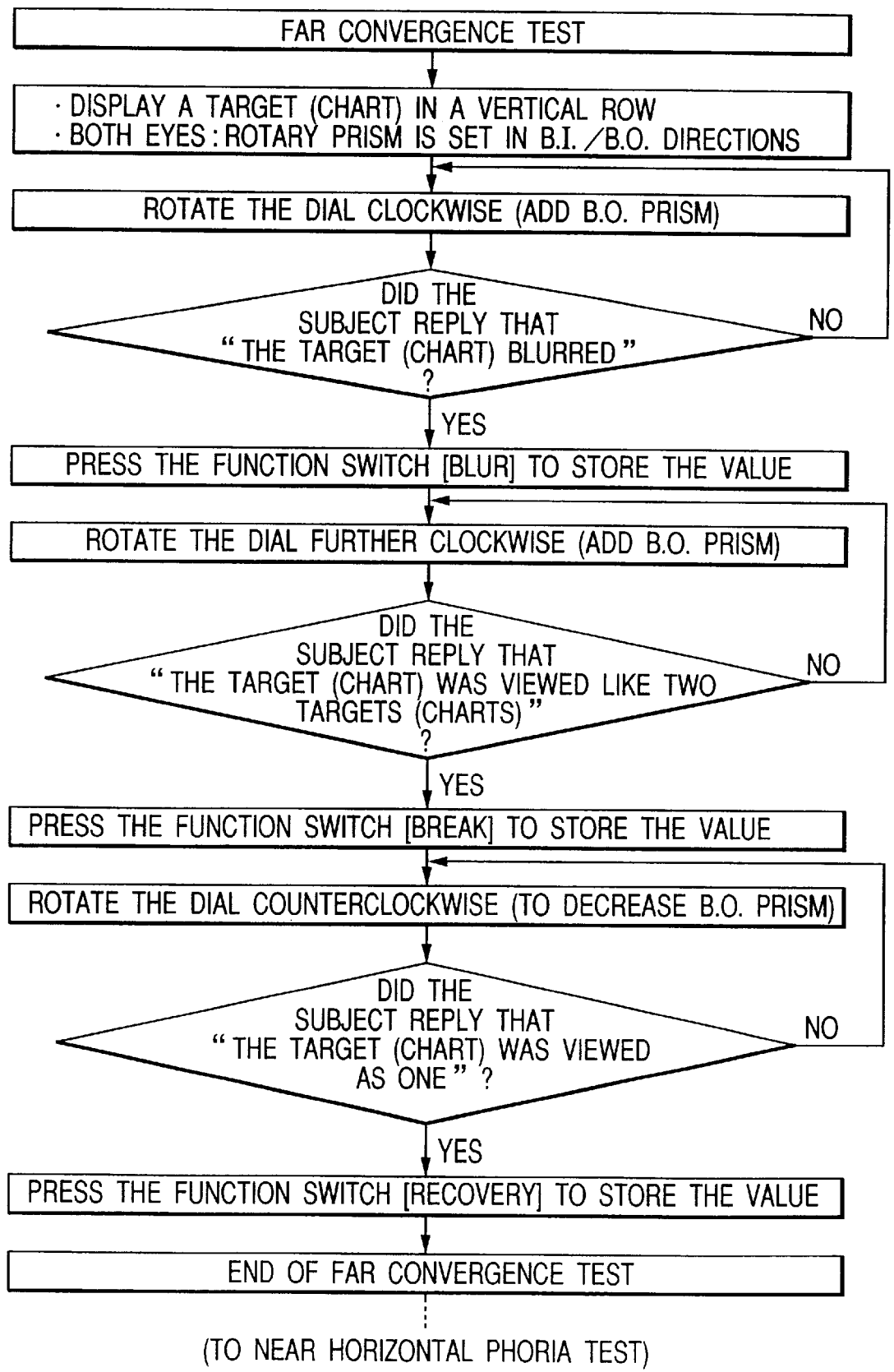
FIG. 27 is a diagram illustrating a flowchart of a visual function testing program in accordance with the embodiment.

<Far Convergence Test—FIG. 27>

Figure 39:
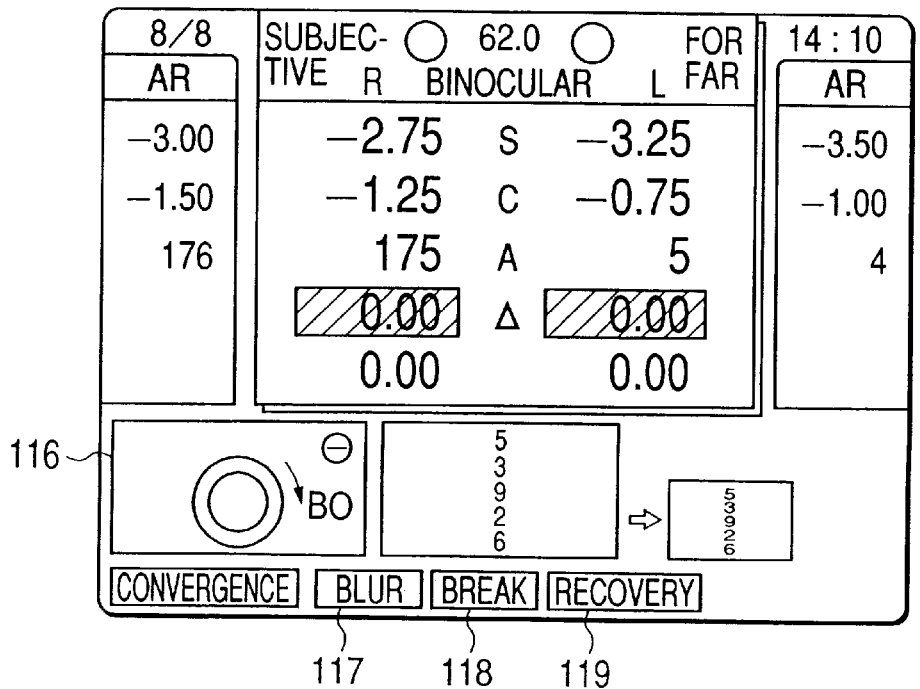
FIG. 39 is a diagram illustrating an example of the screen of the display in a far convergence test.

In the test windows of the subjective-type refractive-power measuring device 2, the pair of rotary prisms are disposed on both eye sides in the B.I./B.O. directions. The smallest letters which the subject can read correctly or letters slightly larger than the same are presented as the target (chart) in a vertical row. By rotating the dial switch 42 clockwise in accordance with advice 116 shown in FIG. 39 to add the B.O. prism, the examiner confirms the subject whether the target (chart) blurred. If blur is not present, the dial switch 42 is rotated further clockwise to add the B.O. prism. Incidentally, at this time, even if the dial switch 42 is rotated counterclockwise, the B.I. prism is not added. If blur is present, a "BLUR" button 117 in the group of function switches 45 is pressed, and the value of the amount of prism at the blurred point is stored.

Then, the dial switch 42 is rotated further clockwise to add the B.O. prism, and the subject is confirmed whether the target (chart) was viewed as if there were two targets (charts). If it was not viewed as if there were two targets (charts), the B.O. prism is further added in the same way as described above. If the target (chart) was viewed as if there were two targets, a "BREAK" button 118 in the group of function switches 45 is pressed, and the value of the amount of prism at the broken (separated) point is stored.

This time, the dial switch 42 is rotated counterclockwise to decrease the B.O. prism, and the subject is confirmed whether the target (chart) was viewed as one (returned). If it was not viewed as one, the dial switch 42 is rotated further counterclockwise to decrease the B.O. prism. If the target (chart) was viewed as one, a "RECOVERY" button 119 in the group of function switches 45 is pressed, and the value of the amount of prism at the recovered point is stored.

Figure 28:
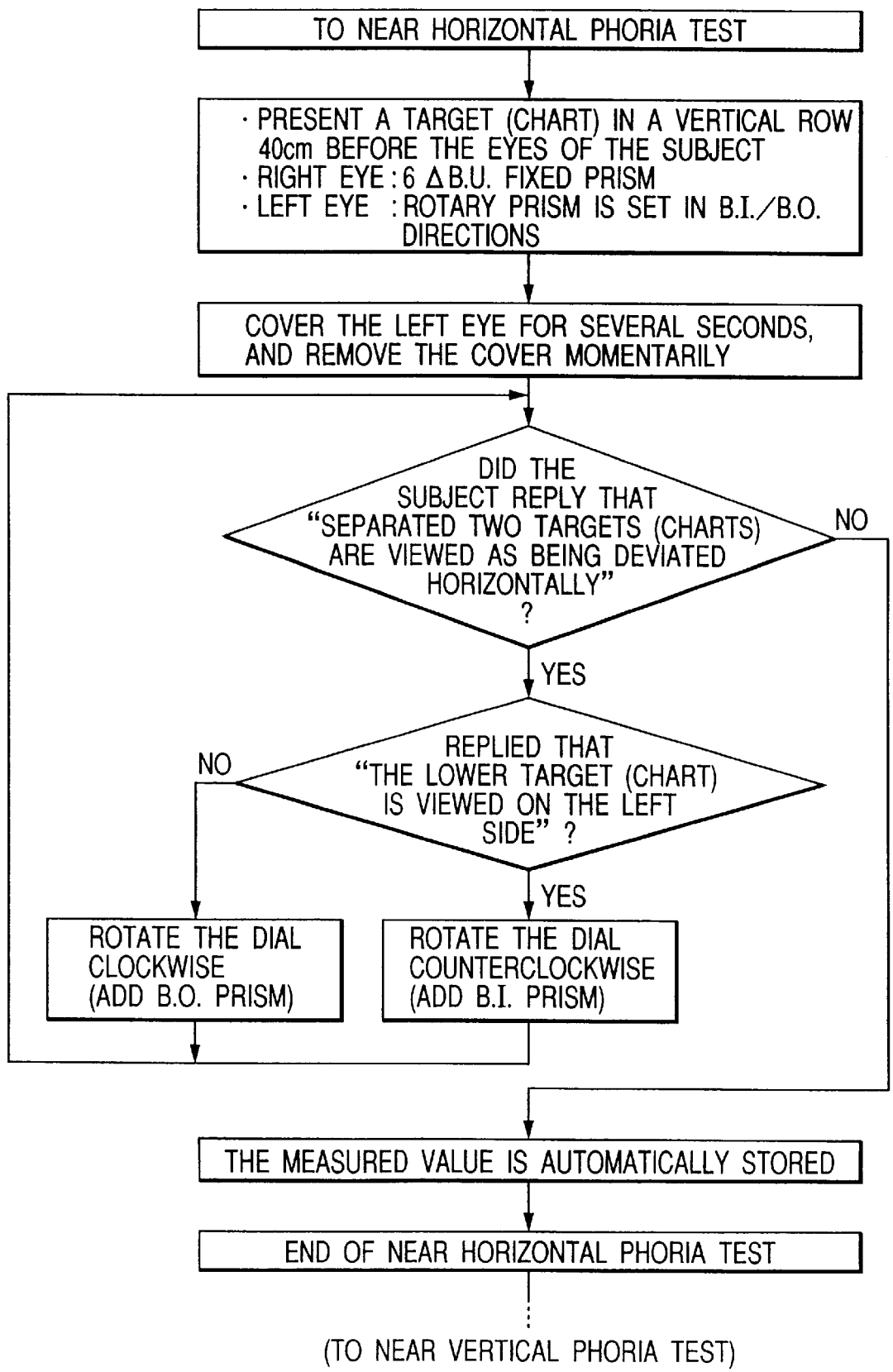
FIG. 28 is a diagram illustrating a flowchart of a visual function testing program in accordance with the embodiment.

<Near Horizontal Phoria Test—FIG. 28>

The prism separation method is adopted for the near horizontal phoria test. The same prisms as those of the far horizontal phoria test are disposed in the test windows of the subjective-type refractive-power measuring device 2. As for the target (chart), one for near use, in which the smallest letters which the subject can read correctly or letters slightly larger than the same are presented in a vertical row, is set 40 cm in front of the eyes of the subject by the examiner. The screen of the display 30 is set in the near use mode, and the display of "FAR USE" at the upper right end of the central display portion 80 changes to "NEAR USE," and the flapping mechanism of the subjective-type refractive-power measuring device 2 is driven, thereby causing the lens units 10 to converge at an angle of convergence corresponding to the near-use distance of 40 cm. The examiner conducts the near horizontal phoria test in the same way as at the time of the far horizontal phoria test.

Figure 29:
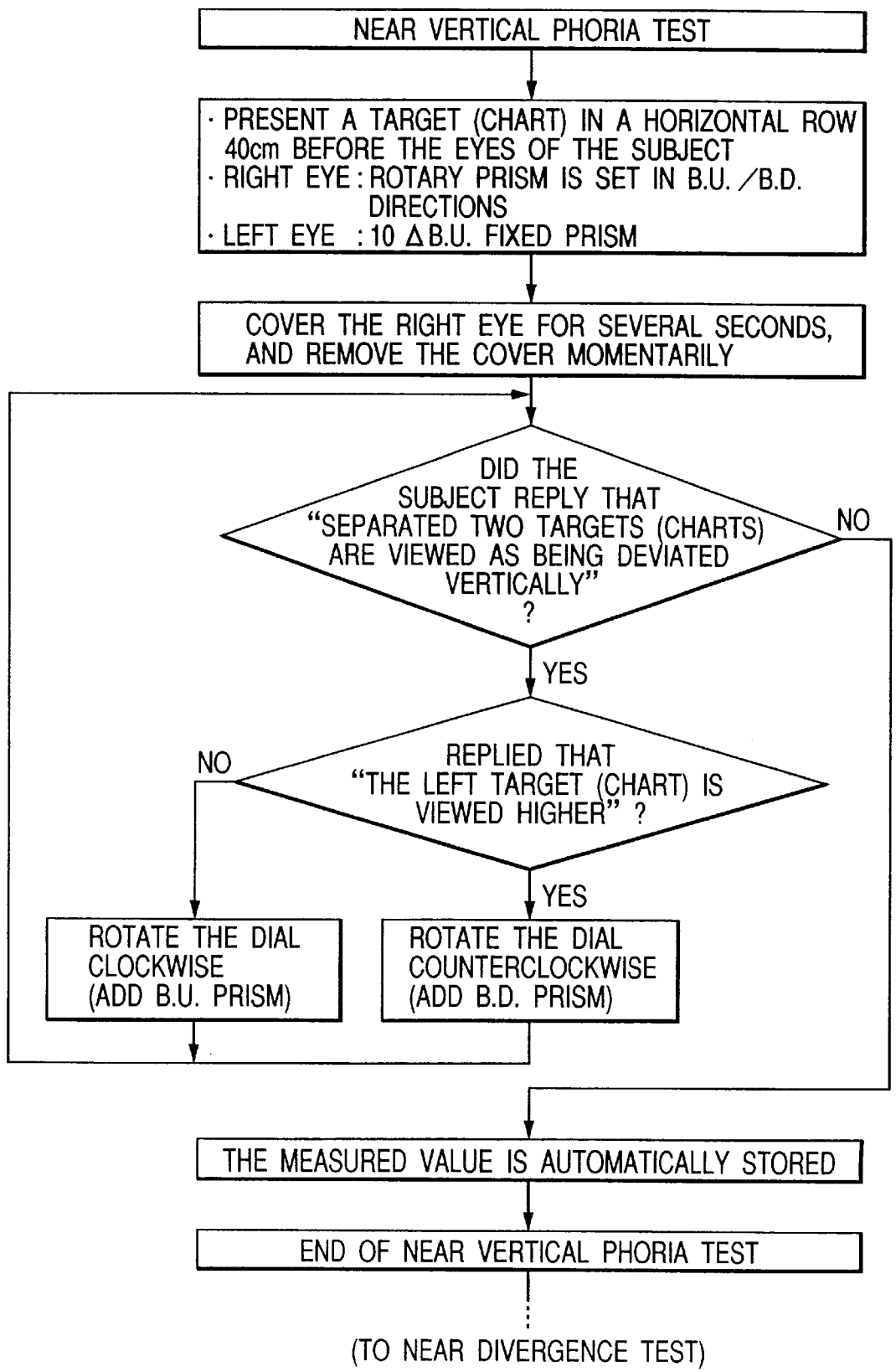
FIG. 29 is a diagram illustrating a flowchart of a visual function testing program in accordance with the embodiment.

<Near Vertical Phoria Test—FIG. 29>

The prism separation method is adopted for the near vertical phoria test as well. The same prisms as those of the far vertical phoria test are disposed in the test windows of the subjective-type refractive-power measuring device 2. As for the target (chart), one for near use, in which the smallest letters which the subject can read correctly or letters slightly larger than the same are presented in a horizontal row, is set 40 cm in front of the eyes of the subject by the examiner. The examiner conducts the near vertical phoria test in the same way as at the time of the far vertical phoria test.

Figure 30:
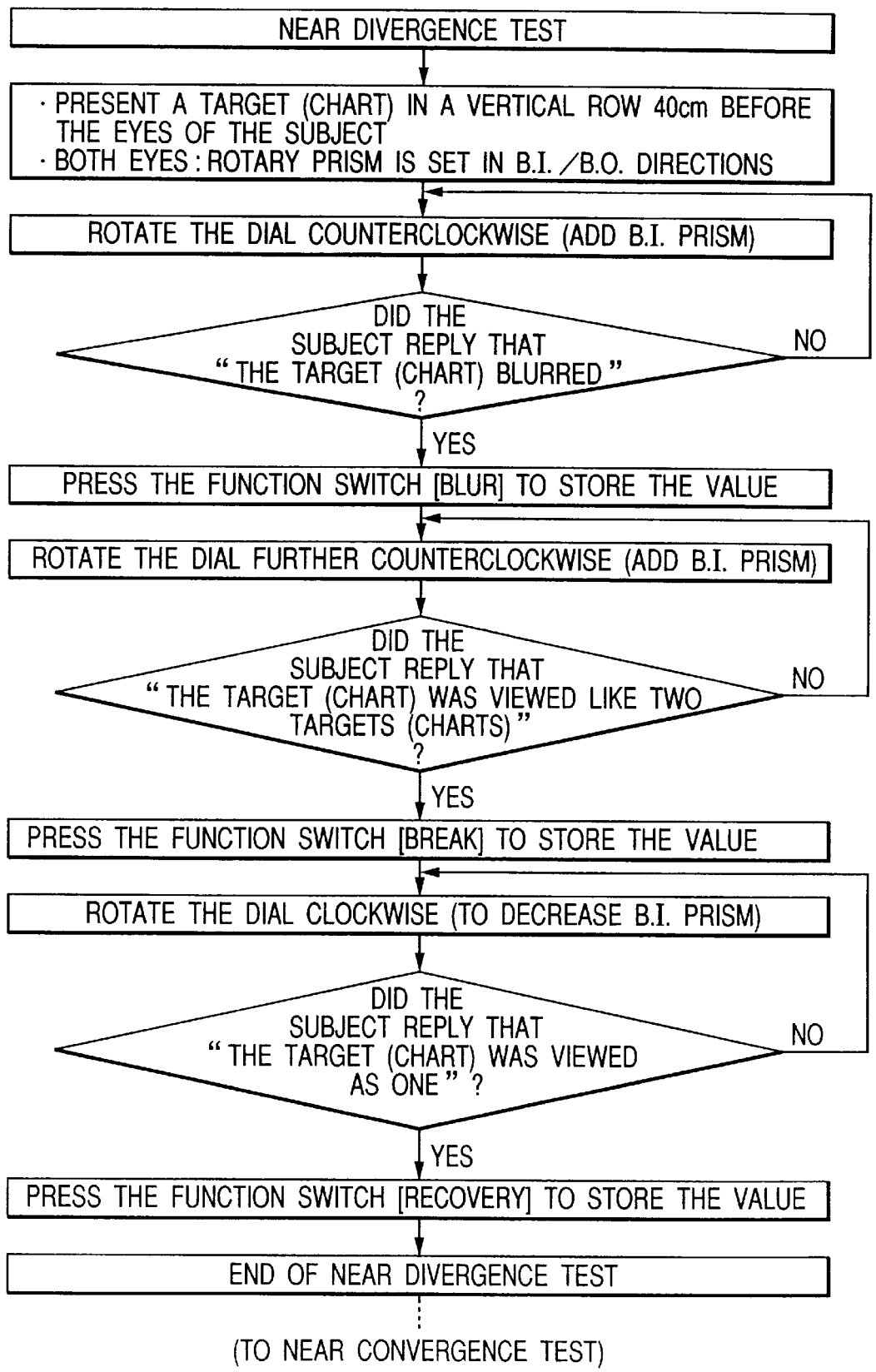
FIG. 30 is a diagram illustrating a flowchart of a visual function testing program in accordance with the embodiment.

<Near Divergence Test—FIG. 30>

The same prisms as those of the far divergence test are disposed in the test windows of the subjective-type refractive-power measuring device 2. As for the target (chart), one for near use, in which the smallest letters which the subject can read correctly or letters slightly larger than the same are presented in a vertical row, is set 40 cm in front of the eyes of the subject by the examiner. The examiner conducts the near divergence test in the same way as at the time of the far divergence test.

Figure 31:
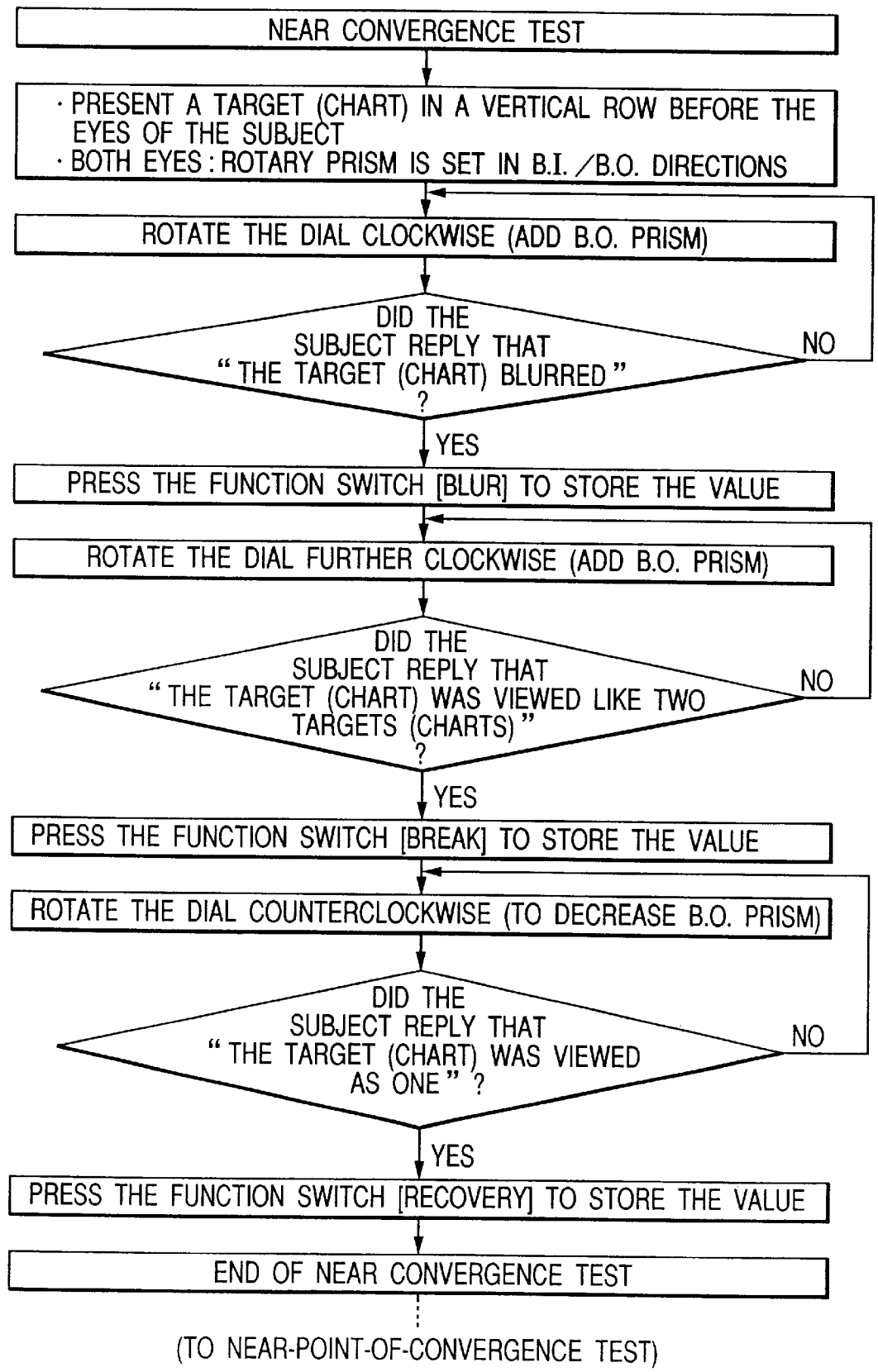
FIG. 31 is a diagram illustrating a flowchart of a visual function testing program in accordance with the embodiment.

<Near Convergence Test—FIG. 31>

The same prisms as those of the far convergence test are disposed in the test windows of the subjective-type refractive-power measuring device 2. As for the target (chart), one for near use, in which the smallest letters which the subject can read correctly or letters slightly larger than the same are presented in a vertical row, is set 40 cm in front of the eyes of the subject by the examiner. The examiner conducts the near convergence test in the same way as at the time of the far convergence test.

Figure 32:
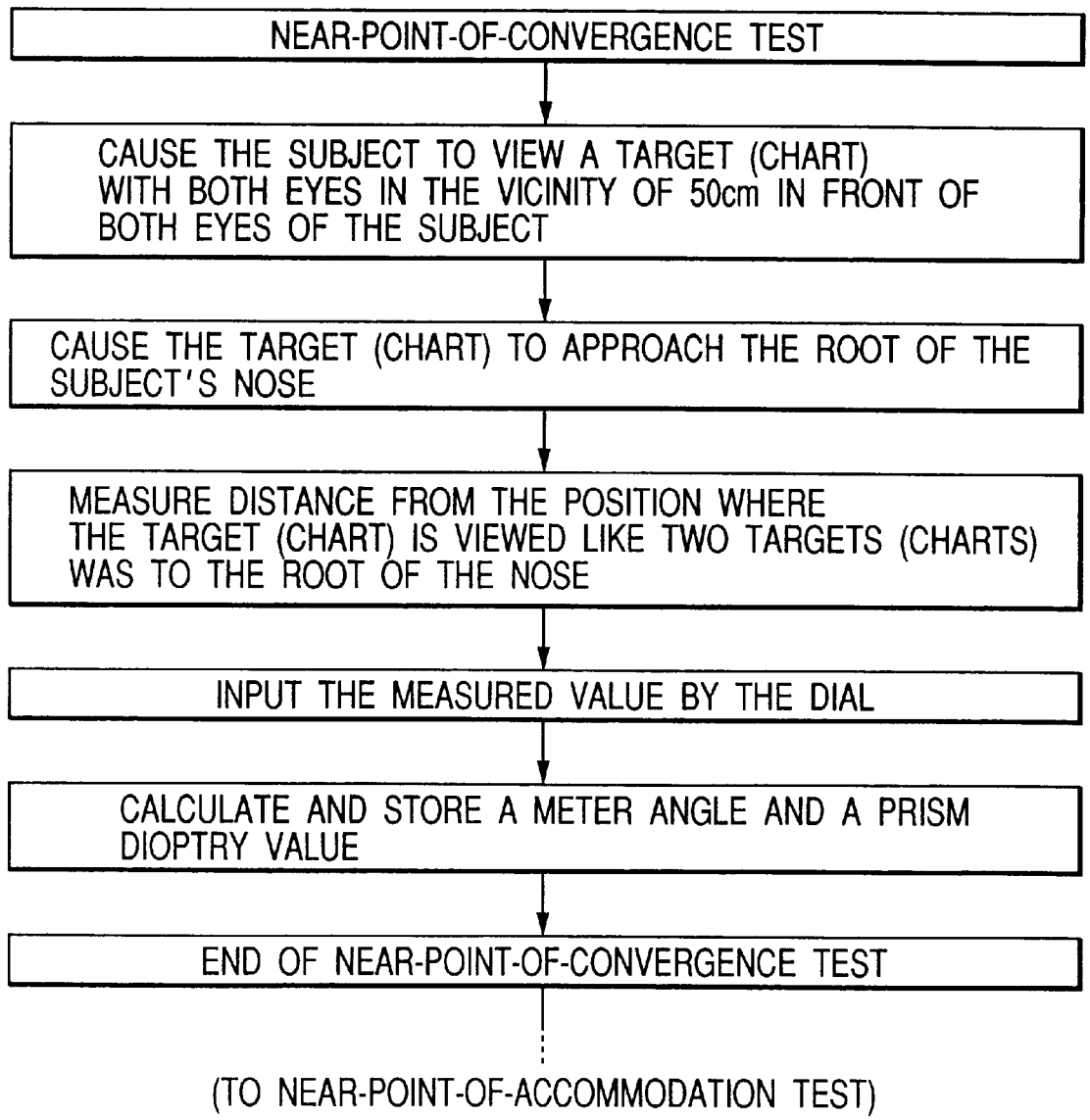
FIG. 32 is a diagram illustrating a flowchart of a visual function testing program in accordance with the embodiment.

<Near Point of Convergence (NPC) Test—FIG. 32>

Figure 40:
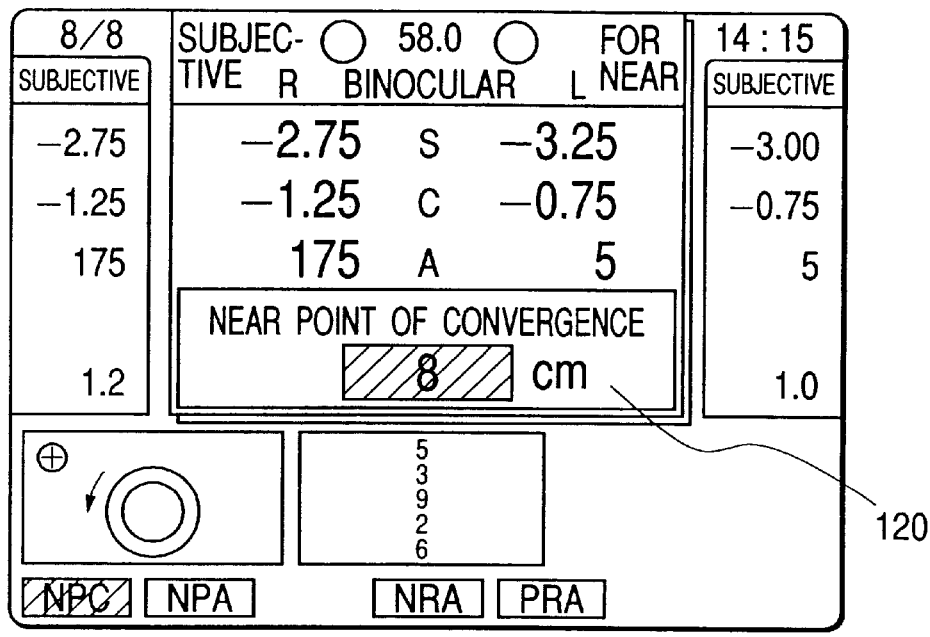
FIG. 40 is a diagram illustrating an example of the screen of the display in a near-point-of-convergence test.

The examiner removes the lens units 10 of the subjective-type refractive-power measuring device 2 from before the eyes of the subject, and causes the subject to view with both eyes a small target such as a penlight in the vicinity of 50 cm in front of both eyes of the subject. The examiner carefully observes both eyes of the subject while causing the target to approach the root of the subject's nose. By using a measure or the like, the examiner measures the position at which the subject said the target began to be seen as if there were two targets (charts), or the position where the line of one eye or the lines of both eyes of the subject failed to move inward or divergence occurred, from the root of the nose, and that distance is inputted to a screen 120 in FIG. 40 by means of the dial switch 42. On the basis of the measured and inputted value of the distance, the apparatus automatically calculates angles of convergence due to a meter angle and prism dioptry in accordance with the following formulae, and stores the respective values.

[Angle of Convergence Due to Meter Angle]

If it is assumed that the measured distance to the root of the nose is d cm, since the distance from the root of the nose to the center of rotation of the eye is approximately 2.5 cm, $$1/(d \times 0.01 + 2.5 \times 0.01) = M.A. \text{ (angle of convergence due to meter angle)}$$

[Angle of Convergence Due to Prism Dioptry]

If the value of the angle of convergence due to a meter angle determined above is multiplied by the pupillary distance at far vision pd cm, $$M.A. \times pd = \Delta \text{ (angle of convergence due to prism dioptry)}$$

Figure 33:
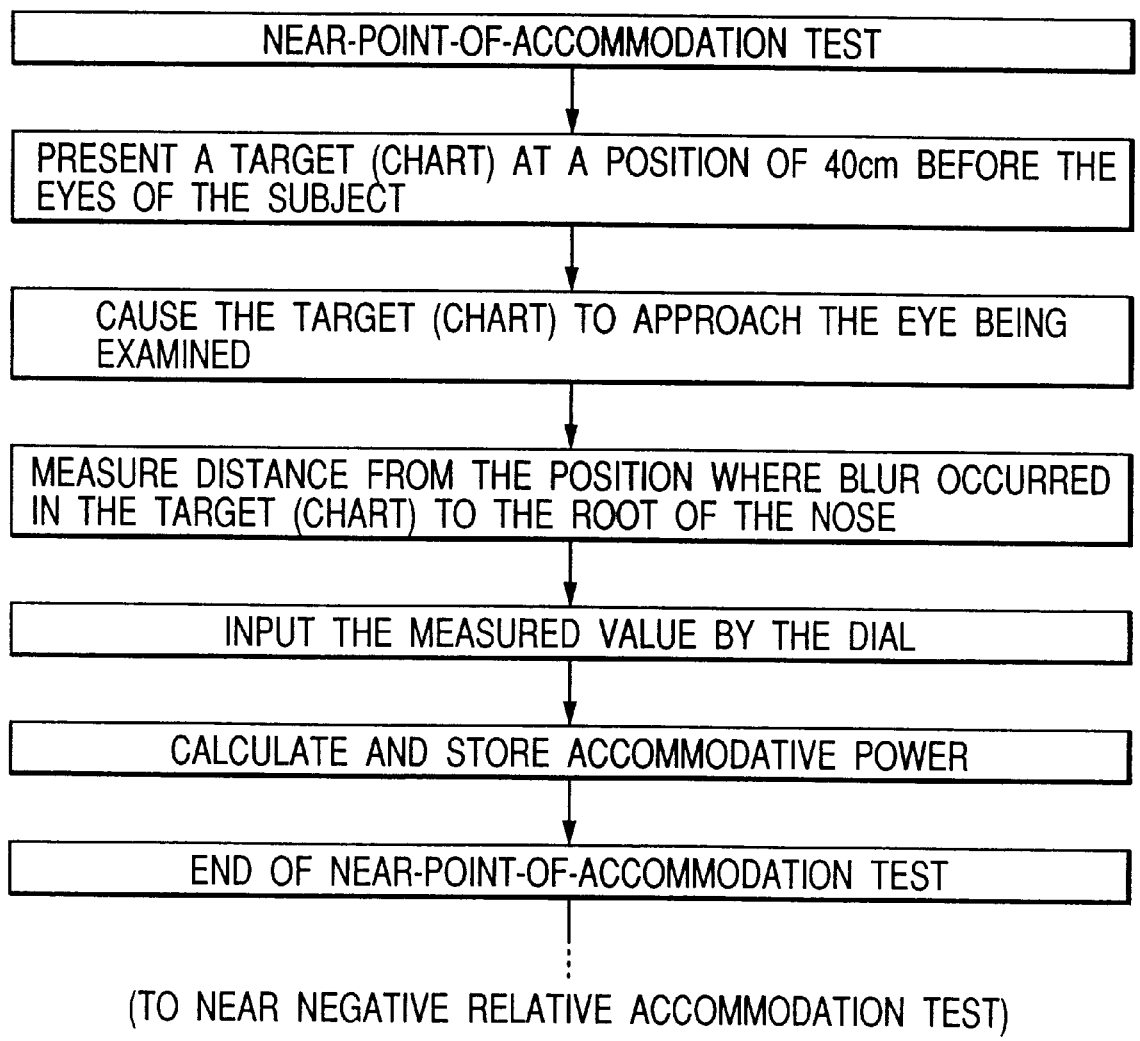
FIG. 33 is a diagram illustrating a flowchart of a visual function testing program in accordance with the embodiment.

<Near Point of Accommodation (NPA) Test—FIG. 33>

Figure 41:
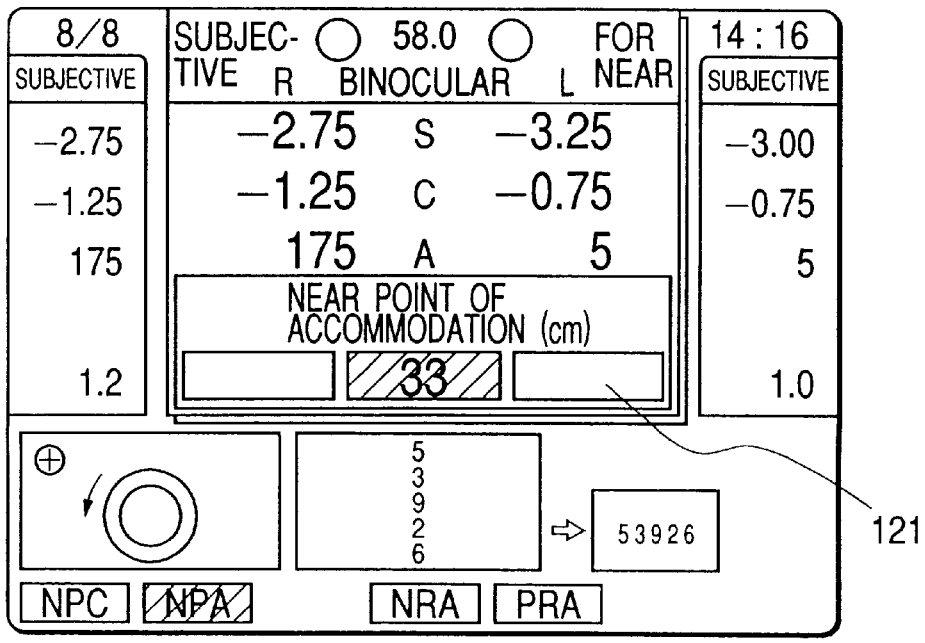
FIG. 41 is a diagram illustrating an example of the screen of the display in a near point of accommodation test.

A pushup method is adopted for the near point of accommodation test. The examiner removes the lens units 10 of the subjective-type refractive-power measuring device 2 from before the eyes of the subject (the lens units 10 may be used), and presents a near-use target (chart) with the smallest letters which the subject can read correctly at a position of 40 cm before the eyes of the subject. While causing the target (chart) to approach the eye being examined, the examiner confirms the subject whether the target (chart) blurred. After confirming the position where the blurring of the target (chart) occurred, the examiner measures the distance from the position of occurrence of the blur to the root of the nose of the subject, and inputs the measured value to a screen 121 in FIG. 41 by means of the dial switch 42. On the basis of the measured and inputted value of the distance, the apparatus automatically calculates the accommodative power in accordance with the following formulae, and stores that value. Incidentally, the test may be effected for one eye at a time or both eyes.

[Accommodative Power]

If the measured distance to the root of the nose=s cm, the accommodative power=A, the accommodative power at near point=P, and the accommodative power at far point=R, then $P=1/(s \times 0.01)$, and $A=P-R$ (R is 0 in perfect correction).

Figure 34:
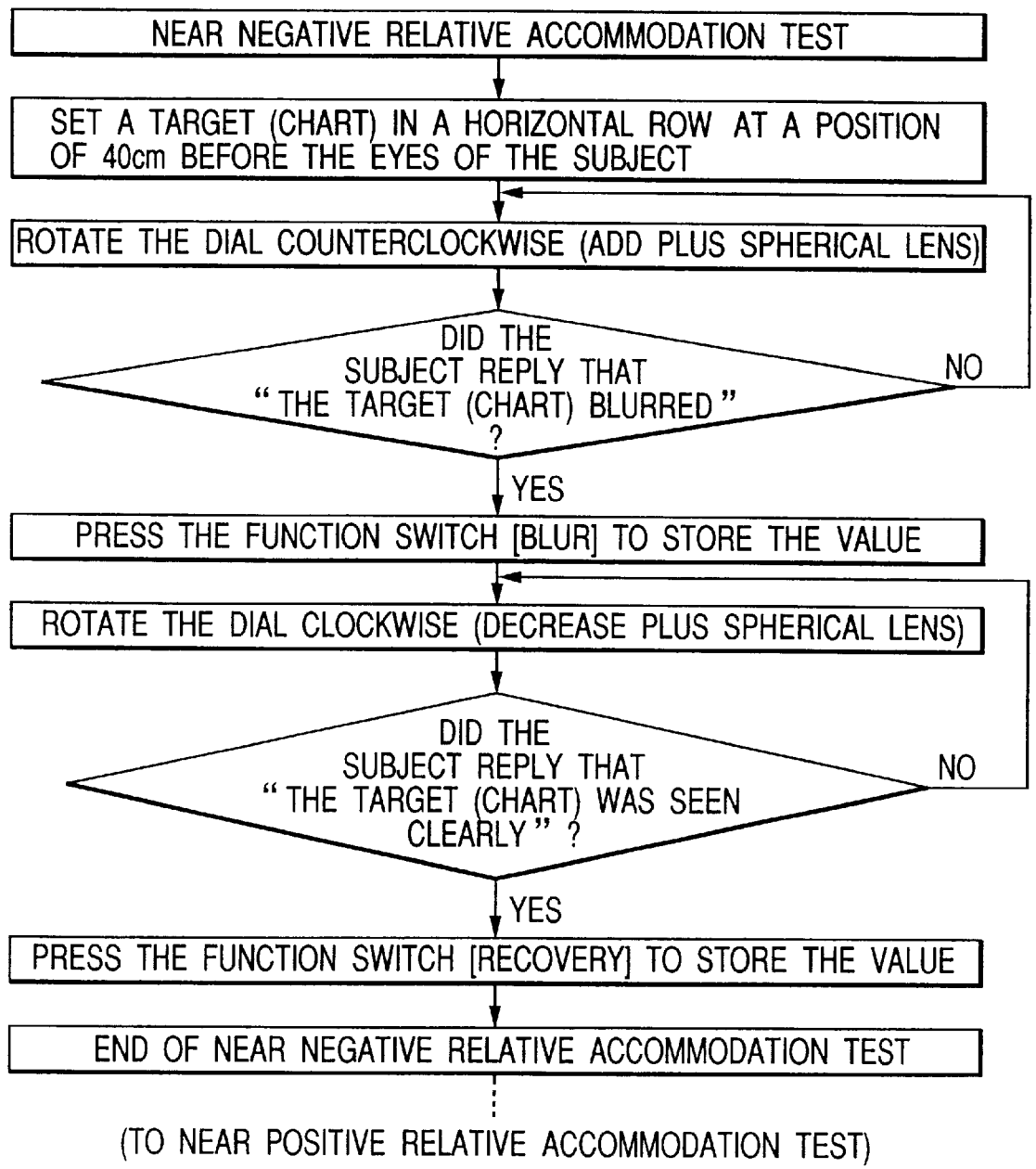
FIG. 34 is a diagram illustrating a flowchart of a visual function testing program in accordance with the embodiment.

<Near Negative Relative Accommodation (NRA) Test—FIG. 34>

Figure 42:
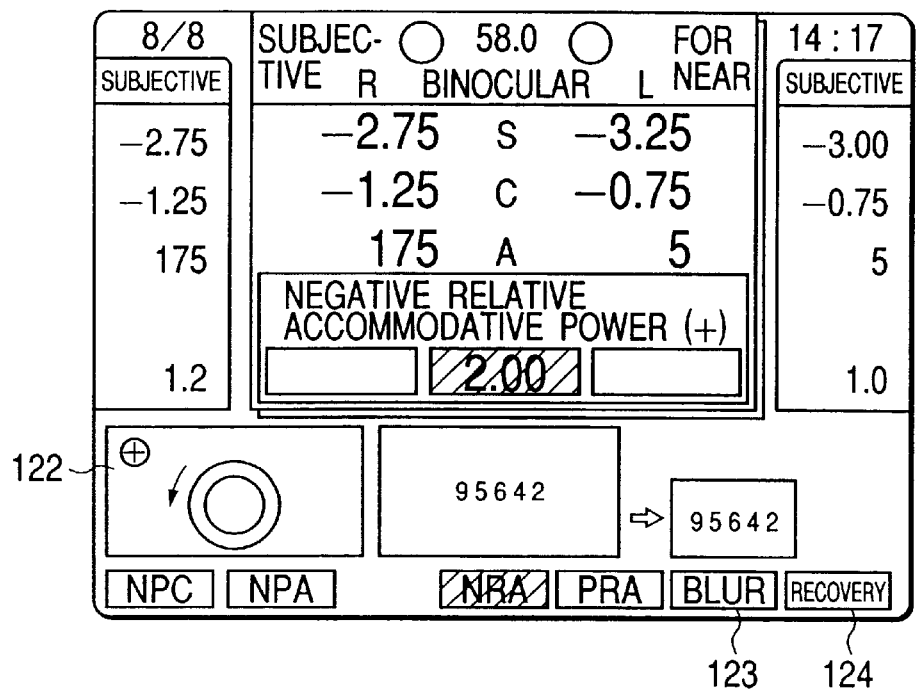
FIG. 42 is a diagram illustrating an example of the screen of the display in a near negative relative accommodation test.

The examiner disposed the lens units 10 of the subjective-type refractive-power measuring device 2 in front of the eyes of the subject, and presents a near-use target (chart) with the smallest letters which the subject can read correctly at a position of 40 cm before the eyes of the subject. The examiner rotates the dial switch 42 counterclockwise in accordance with advice 122 in FIG. 42 to add the plus spherical lens, and confirms the subject whether the target (chart) blurred. If the blur is not present, the examiner rotates the dial switch 42 further counterclockwise to add the plus spherical lens. Incidentally, at this time, even if the dial switch 42 is rotated clockwise, the minus spherical lens is not added. If the blur is present, the examiner presses a "BLUR" button 123 in the group of function switches 45, and the power of the plus spherical lens at the blurred point is stored.

This time, the examiner rotates the dial switch 42 clockwise to decrease the plus spherical lens, and confirms the subject whether the target (chart) was seen clearly (returned). If the target (chart) was not seen clearly, the dial switch 42 is rotated further clockwise to decrease the plus spherical lens. If the target (chart) was seen clearly, a "RECOVERY" button 124 in the group of function switches 45 is pressed, and the power of the plus spherical lens at the recovered point is stored.

Figure 35:
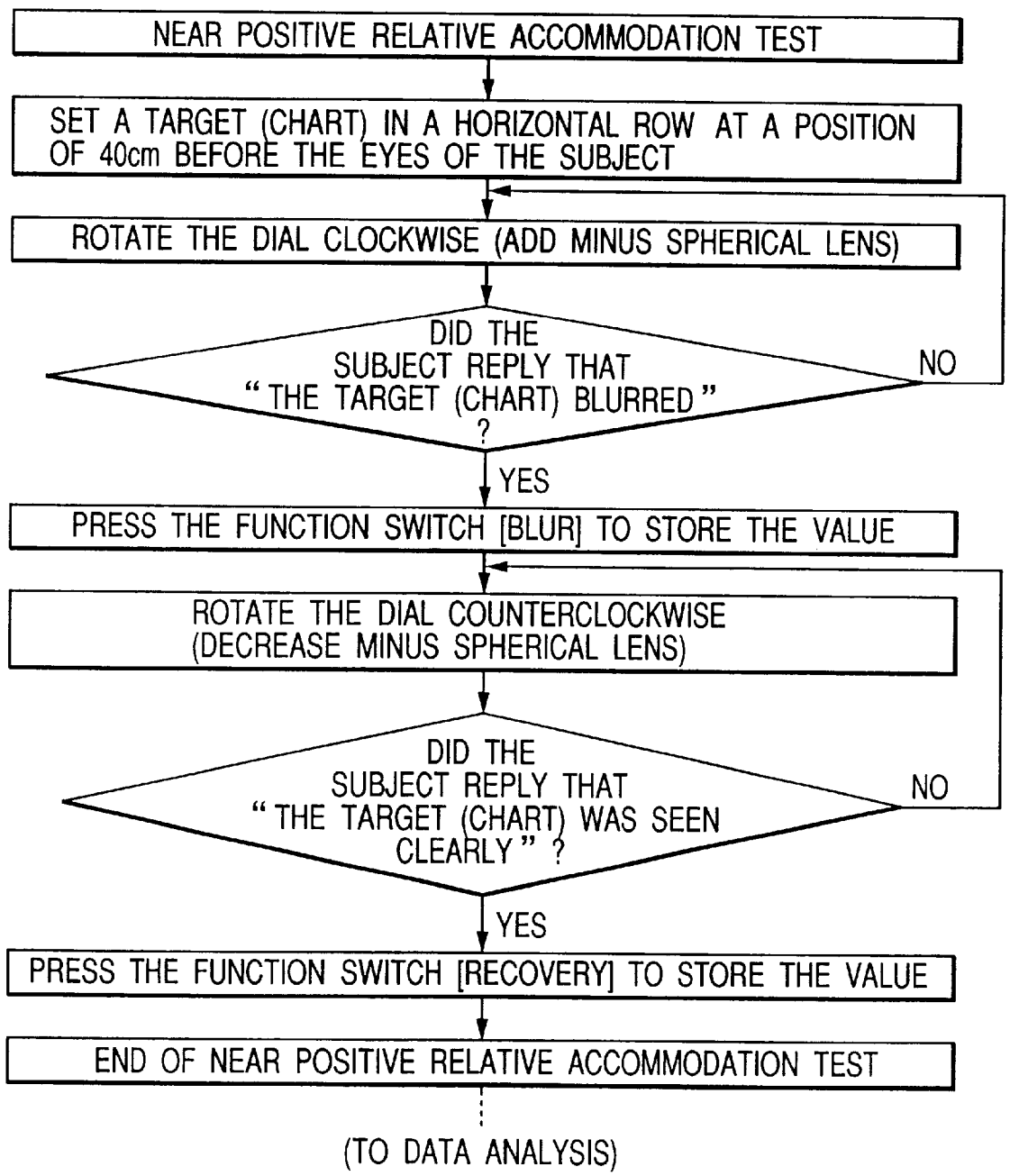
FIG. 35 is a diagram illustrating a flowchart of a visual function testing program in accordance with the embodiment.

<Near Positive Relative Accommodation (PRA) Test—FIG. 35>

Figure 43:
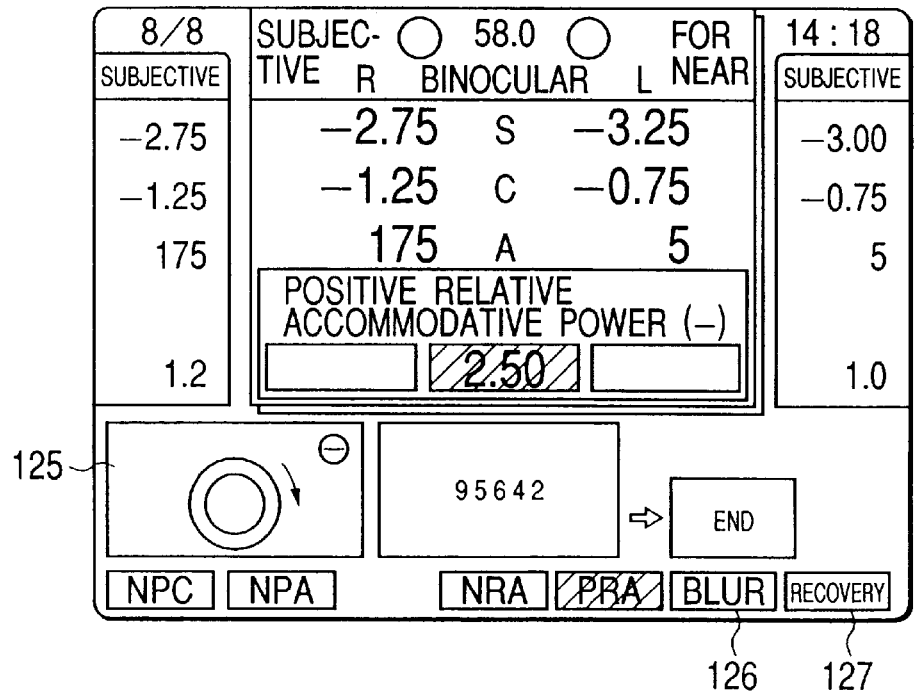
FIG. 43 is a diagram illustrating an example of the screen of the display in a near positive relative accommodation test.

The examiner disposed the lens units 10 of the subjective-type refractive-power measuring device 2 in front of the eyes of the subject, and presents a near-use target (chart) with the smallest letters which the subject can read correctly at a position of 40 cm before the eyes of the subject. The examiner rotates the dial switch 42 clockwise in accordance with advice 125 in FIG. 43 to add the minus spherical lens, and confirms the subject whether the target (chart) blurred. If the blur is not present, the examiner rotates the dial switch 42 further clockwise to add the minus spherical lens. Incidentally, at this time, even if the dial switch 42 is rotated counterclockwise, the plus spherical lens is not added. If the blur is present, the examiner presses a "BLUR" button 126 in the group of function switches 45, and the power of the minus spherical lens at the blurred point is stored.

This time, the examiner rotates the dial switch 42 counterclockwise to decrease the minus spherical lens, and confirms the subject whether the target (chart) was seen clearly (returned). If the target (chart) was not seen clearly, the dial switch 42 is rotated further counterclockwise to decrease the minus spherical lens. If the target (chart) was seen clearly, a "RECOVERY" button 127 in the group of function switches 45 is pressed, and the power of the minus spherical lens at the recovered point is stored.

After the foregoing visual function tests are finished, if the menu switch 32a is pressed to select the list of data, the table on S, C, A, ADD (addition power), and VA (visual acuity value) for far use shown in FIG. 44 is displayed. The examiner is able to see the following data by pressing the function key 45.

When invoking [data on S, C, A, ADD, and VA for far use—FIG. 44], a "FAR USE" button 128 and an "SCA" button 130 in the group of function switches 45 are pressed.

When invoking [data on S, C, A, ADD, and VA for near use—FIG. 45], a "NEAR USE" button 129 and the "SCA" button 130 in the group of function switches 45 are pressed.

When invoking [data on prism for far use (horizontal phoria, vertical phoria, convergence, and divergence)—FIG. 46], the "FAR USE" button 128 and a "PRISM" button 131 in the group of function switches 45 are pressed.

When invoking [data on prism for near use (horizontal phoria, vertical phoria, convergence, and divergence)—FIG. 47], the "NEAR USE" button 129 and the "PRISM" button 131 in the group of function switches 45 are pressed.

Figures 48, 49:
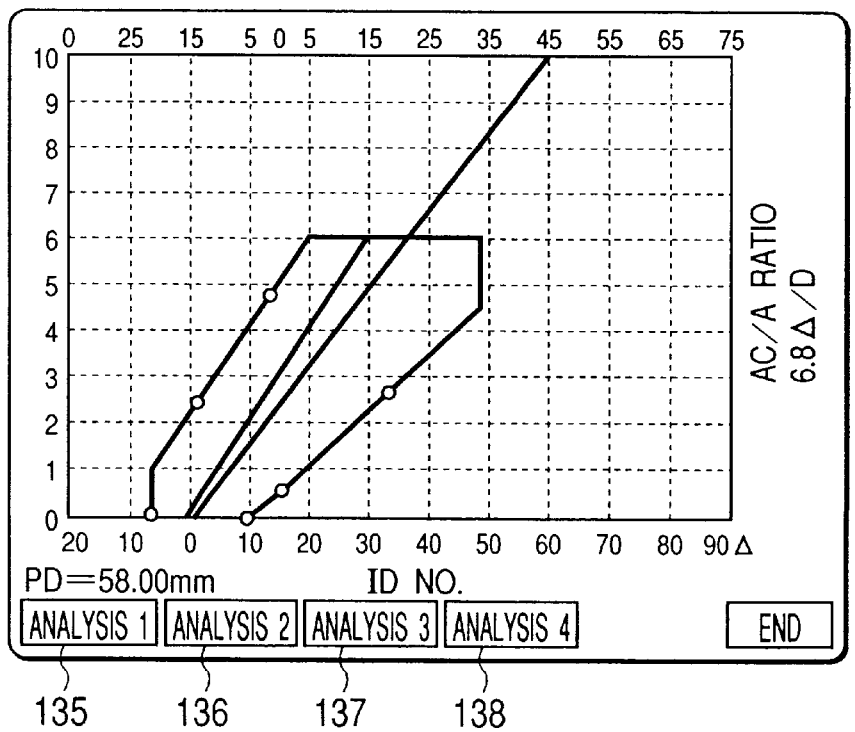
FIG. 48 is a diagram illustrating an example of the screen of the display of a table of data in a visual function test.
FIG. 49 is a diagram illustrating an example of the screen of the display of graph data and AC/A (Accommodative Convergence/Accommodation) ratio in a visual function test.

When invoking [data on NPC, NPA, NRA, and PRA for near use—FIG. 48], the "NEAR USE" button 129 and a "NPC" button 132 in the group of function switches 45 are pressed.

When invoking [display of graph data and AC/A ratio (ratio between accommodative convergence and accommodation)—FIG. 49], a "graph" button 133 in the group of function switches 45 is pressed.

Further, by pressing "ANALYSIS 1–4" in the group of function switches 45 shown in FIG. 49, the results of analysis and a method of prescription based on the measurement values obtained from the foregoing visual function tests can be displayed on the screen. If an "ANALYSIS 1" button 135 is pressed, the results of analysis and a method of prescription based on the AC/A ratio and the eye position are displayed (see FIG. 50). If an "ANALYSIS 2" button 136 is pressed, the results of analysis and a method of prescription based on the Sheard's criteria are displayed (see FIG. 51). If an "ANALYSIS 3" button 137 is pressed, the results of analysis and a method of prescription based on the Percival's criteria are displayed (see FIG. 52). If an "ANALYSIS 4" button 138 is pressed, the results of analysis and a method of prescription based on the Morgan's system are displayed (see FIG. 53). The examiner is able to correct an error in the visual function of the subject in line with the results of analysis and the method of prescription.

In accordance with the present invention, even a person who is inexperienced and unfamiliar with optometry is able to easily obtain appropriate prescription values, and is able to conduct analysis of the visual function.

What is claimed is:

1. An optometric apparatus for correcting refraction of an eye to be examined, comprising:

a rotary prism for imparting a prism power to the eye to be examined;

program storing means for storing a program for conducting examination by using said rotary prism;

program advancing means for advancing said program;

prism-power storing means for storing a prism power of an expected state; and display means for displaying a result of examination.

2. An optometric apparatus according to claim 1, wherein said program stored in said program storing means includes a program in which an operating method in an examination process is displayed by said display means.

3. An optometric apparatus according to claim 1, wherein said program stored in said program storing means includes at least one of a horizontal phoria test, a vertical phoria test, a divergence test, and a convergence test.

4. An optometric apparatus according to claim 3, wherein tests for far use and near use are included in each of said tests.

5. An optometric apparatus according to claim 1, wherein said program stored in said program storing means includes at least one of a near-point-of-convergence test, a near-point-of-accommodation test, and a near accommodation test.

6. An optometric apparatus according to claim 5, further comprising:

input means for inputting a distance from a root of a nose at the time of said near-point-of-convergence test or said near-point-of-accommodation test; and calculating means for effecting a predetermined calculation on the basis of the inputted distance.

7. An optometric apparatus according to claim 1, wherein the result of examination displayed by said display means includes a result of analysis in which the result of examination is analyzed.

8. A controller for operating a subjective-type refractive-power measuring device and a target presenting device in an optometric apparatus, said controller comprising:

a memory which stores therein a program for a visual function test to be executed after perfect correction values for both eyes are obtained;

a microcomputer circuit connected to said memory to control said subjective-type refractive-power measuring device and said target presenting device in accordance with said program;

a switch section through which an examiner can control said subjective-type target presenting device and can instruct whether a current test item of the visual function test should be continued depending on a reply from a subject; and a display on which an advice regarding how to control the subjective-type target presenting device is displayed if the examiner instructs, through said switch section, that said current test item should be continued.

9. A controller according to claim 8, wherein said memory automatically stores therein a result of the current test item if the examiner instructs that said current test item should not be continued.

10. A controller designed for an optometric apparatus, comprising:

a memory which stores therein a program for a visual function test including at least one of horizontal phoria test, a vertical phoria test, a divergence test, a convergence test, a near-point-of-convergence test, a near-point-of-accommodation test, and a near accommodation test;

a microcomputer circuit connected to said memory;

a switch section connected to said microcomputer circuit; and a display connected to said microcomputer circuit.

* * * * *